(12) United States Patent
Verhoest et al.

(10) Patent No.: US 7,964,607 B2
(45) Date of Patent: Jun. 21, 2011

(54) PYRAZOLO[3,4-D]PYRIMIDINE COMPOUNDS

(75) Inventors: Patrick Robert Verhoest, Old Lyme, CT (US); Caroline Proulx-Lafrance, Ledyard, CT (US)

(73) Assignee: Pfizer Inc., New York, NY (US)

( * ) Notice: Subject to any disclaimer, the term of this patent is extended or adjusted under 35 U.S.C. 154(b) by 562 days.

(21) Appl. No.: 12/118,062

(22) Filed: May 9, 2008

(65) Prior Publication Data
US 2009/0030003 A1    Jan. 29, 2009

Related U.S. Application Data

(60) Provisional application No. 60/917,333, filed on May 11, 2007.

(51) Int. Cl.
C07D 487/04 (2006.01)
A61K 31/519 (2006.01)
A61P 25/28 (2006.01)

(52) U.S. Cl. ..................... 514/262.1; 544/262
(58) Field of Classification Search .................. 544/262; 514/262.1
See application file for complete search history.

(56) References Cited

U.S. PATENT DOCUMENTS

| | | | |
|---|---|---|---|
| 2003/0139427 A1 | 7/2003 | Castelhano et al. | 514/261.1 |
| 2004/0176361 A1 | 9/2004 | Fujio et al. | 514/224.2 |
| 2004/0259870 A1 | 12/2004 | Feng et al. | 514/229.2 |

FOREIGN PATENT DOCUMENTS

| | | |
|---|---|---|
| EP | 1460077 | 9/2004 |
| WO | 02085904 | 10/2002 |
| WO | 2004037176 | 5/2004 |

OTHER PUBLICATIONS

Wunder et al., Mol. Pharmacol., vol. 28, No. 6, (2005), pp. 1776-1781.
van der Staay et al., Neuropharmacology, vol. 55 (2008), pp. 908-918.

*Primary Examiner* — Susanna Moore
(74) *Attorney, Agent, or Firm* — Jennifer A. Kispert; Michael Herman

(57) ABSTRACT

The invention provides PDE9-inhibiting compounds of Formula (I),

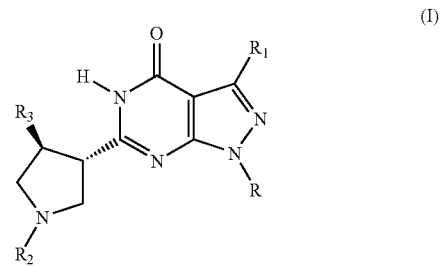

(I)

and pharmaceutically acceptable salts thereof, wherein R, $R_1$, $R_2$ and $R_3$ are as defined herein. Pharmaceutical compositions containing the compounds of Formula I, and uses thereof in treating neurodegenerative and cognitive disorders, such as Alzheimer's disease and schizophrenia, are also provided.

13 Claims, No Drawings

PYRAZOLO[3,4-D]PYRIMIDINE COMPOUNDS

RELATED APPLICATION

This application claims the benefit under 35 U.S.C. §119(e) of U.S. provisional application Ser. No. 60/917,333, filed May 11, 2007.

FIELD OF THE INVENTION

This invention relates to a series of novel compounds that are selective inhibitors of phosphodiesterase type 9 ("PDE9"). More particularly, the invention relates to pyrazolo[3,4-d]pyrimidinone compounds for use in the treatment and prevention of neurodegenerative diseases and other diseases and disorders influenced by modulation of PDE9.

BACKGROUND OF THE INVENTION

Cyclic nucleotides cyclic guanosine monophosphate (cGMP) and cyclic adenosine monophosphate (cAMP) are important second messengers and thus are central to the control and regulation of a multitude of cellular events, both physiological and pathophysiological, in a wide variety of organs.

Cyclic GMP is formed from GTP by the catalytic reaction of guanylyl cyclase (GC), which is activated by nitric oxide (NO). Cyclic GMP in turn activates cGMP-dependent protein kinases (cGK), which mediate localized and global signaling. A variety of physiological processes in the cardiovascular, nervous and immune systems are controlled by the NO/cGMP pathway, including ion channel conductance, glycogenolysis, cellular apoptosis, and smooth muscle relaxation. In blood vessels, relaxation of vascular smooth muscles leads to vasodilation and increased blood flow.

The phosphodiesterase (PDE) enzyme family hydrolyses cGMP and cAMP. The PDE9 enzyme has been identified as a novel member of the PDE enzyme family that selectively hydrolyses cGMP over cAMP. See Fisher et al., *J. Biol. Chem.*, 273(25), 15559-15564 (1998). PDE9 has been found to be present in a variety of human tissues, namely the testes, brain, small intestine, skeletal muscle, heart, lung, thymus and spleen, as well as in smooth muscle cells within the human vasculature of a variety of tissues.

Recent studies have directly implicated dysfunction of NO/cGMP/cGK signaling in Alzheimer's disease. For example, disruption of Long Term Potentiation (LTP), a physiological correlate of learning and memory, by amyloid-β peptide was shown to result from a malfunction of NO/cGMP signaling. Puzzo et al., *J. Neurosci.*, 25(29):6887-6897 (2005). Moreover, in rats showing deficits in memory tasks due to depletion in forebrain acetylcholinesterase (which is associated with Alzheimer's disease), administration of a nitric oxide mimetic increased GC activity and reversed the cognitive deficits in memory tasks. Bennett et al., *Neuropsychopharmacology*, 32:505-513 (2007). It is therefore believed that therapeutic agents capable of enhancing the GC/NO/cGMP/cGK signaling cascade may be useful as a new approach to the treatment of Alzheimer's disease and other neurodegenerative disorders.

By reducing or preventing the hydrolysis of cGMP by PDE9, PDE9 inhibitors elevate the intracellular level of cGMP, thus enhancing or prolonging its effects. It has been found that an increase in cGMP concentration in rats leads to improvement in learning and memory in social and object recognition tests. See, e.g., Boess et al., *Neuropharmacology*, 47:1081-1092 (2004). Inhibition of PDE9 has been shown to increase LTP. Hendrix, *BMC Pharmacol.*, 5(Supp 1):55 (2005).

Accordingly, there is a need for PDE9 inhibitors that are effective in treating conditions that may be regulated or normalized by inhibition of PDE9.

SUMMARY OF THE INVENTION

The present invention is directed to compounds of Formula (I),

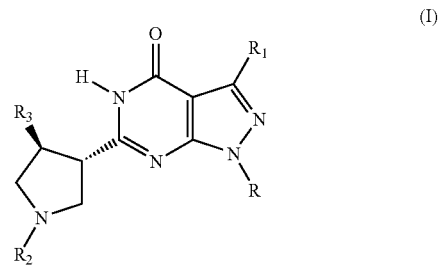

and pharmaceutically acceptable salts thereof, wherein R, $R_1$, $R_2$, and $R_3$ are as defined herein.

The present invention is also directed to compositions containing a compound of Formula (I), or a pharmaceutically acceptable salt thereof, and a pharmaceutically acceptable vehicle, carrier or diluent, and optionally further comprising a second pharmaceutical agent.

The present invention is further directed to a method of inhibiting PDE9 in a mammal in need of such inhibition, comprising the step of administering to the mammal a PDE9-inhibiting amount of a) a compound of Formula I, or a pharmaceutically acceptable salt thereof; or b) a pharmaceutical composition comprising a compound of Formula I, or a pharmaceutically acceptable salt thereof, and a pharmaceutically acceptable vehicle, carrier or diluent.

The present invention is further directed to a method of treating a neurodegenerative disease in a mammal in need of such treatment, comprising the step of administering to the mammal a therapeutically effective amount of a compound of Formula I, or a pharmaceutically acceptable salt thereof.

The present invention is further directed to a method of promoting neurorestoration in a mammal in need of such neurorestoration, comprising the step of administering to the mammal a therapeutically effective amount of a compound of Formula I, or a pharmaceutically acceptable salt thereof.

The present invention is still further directed to a method of improving cognitive deficits and treating cognitive impairment in a mammal in need of such improvement or treatment, comprising the step of administering to the mammal a therapeutically effective amount of a compound of Formula I, or a pharmaceutically acceptable salt thereof.

With the foregoing and other advantages and features of the invention that will become hereinafter apparent, the nature of the invention may be more clearly understood by reference to the following detailed description of the invention and the appended claims.

DETAILED DESCRIPTION OF THE INVENTION

The present invention comprises novel selective PDE9 inhibitors of Formula (I),

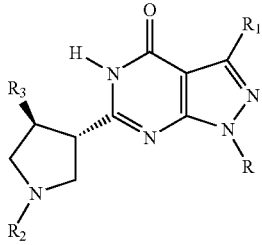

(I)

and pharmaceutically acceptable salts thereof, wherein:

R is selected from the group consisting of $(C_1-C_6)$alkyl, $(C_2-C_6)$alkenyl, $(C_2-C_6)$alkynyl, $(C_3-C_8)$cycloalkyl, heterocycloalkyl, aryl, and heteroaryl, each of which optionally may be substituted with one to three substituents, the substituents being independently selected from the group consisting of $(C_1-C_4)$alkyl, $(C_1-C_4)$alkoxy, halo, and $(C_1-C_4)$ haloalkyl.

$R_1$ is selected from the group consisting of hydrogen, $(C_1-C_4)$alkyl, $(C_2-C_4)$alkenyl, $(C_2-C_4)$alkynyl, $(C_1-C_4)$haloalkyl, and cyclopropyl;

$R_2$ is selected from the group consisting of $(C_1-C_6)$alkyl, $(C_2-C_6)$alkenyl, $(C_2-C_6)$alkynyl, $(C_1-C_6)$haloalkyl, heteroaryl selected from the group consisting of pyridinyl, pyridazinyl, pyrimidinyl, and pyrazinyl, and $ER_5$, wherein the heteroaryl optionally may be substituted with one to three substituents independently selected from the group consisting of $(C_1-C_4)$alkyl and $(C_1-C_4)$haloalkyl;

$R_3$ is selected from the group consisting of hydrogen, $(C_1-C_4)$alkyl, $(C_1-C_4)$alkenyl, $(C_2-C_4)$alkynyl, $(C_3-C_6)$cycloalkyl, and $(C_1-C_4)$haloalkyl;

E is selected from the group consisting of —CH$_2$—, —CH$_2$CH$_2$—, —CH$_2$CH$_2$CH$_2$—, and —C(O)—;

$R_5$ is selected from the group consisting of $(C_3-C_8)$cycloalkyl, heterocycloalkyl, aryl, aryloxy, and heteroaryl, any of which optionally may be substituted with one to three substituents, such substituents being independently selected from the group consisting of $(C_1-C_4)$alkyl, $(C_2-C_4)$alkenyl, $(C_2-C_4)$alkynyl, $(C_1-C_4)$hydroxyalkyl, $(C_1-C_4)$haloalkyl, $(C_1-C_4)$alkoxy, $(C_1-C_4)$haloalkoxy, $(C_3-C_8)$cycloalkyl, halo, cyano, phenyl, morpholinyl, $(C_1-C_4)$alkylamino, pyrazolyl, triazolyl, and imidazolyl.

Preferably, R is selected from the group consisting of ethyl, isopropyl, trifluoroethyl, cyclobutyl, cyclopentyl, difluorocyclohexyl, methoxyphenyl, and tetrahydro-2H-pyran-4-yl; $R_1$ is hydrogen or methyl; $R_2$ is methyl, trifluoroethyl, trifluorobutyl, pyrimidinyl, trifluoromethylpyrimidinyl, or $ER_5$; $R_3$ is methyl, ethyl, isopropyl, trifluoromethyl, trifluoroethyl, or cyclopropyl; E is —CH$_2$— or —C(O)—; and $R_5$ is selected from the group consisting of substituted or unsubstituted cyclopentyl, morpholinyl, phenyl, naphthyl, benzyloxy, pyrimidinyl, pyridinyl, quinolinyl, quinoxalinyl, pyrazinyl, pyrazolyl, benzimidazolyl, cinnolinyl, naphthydrinyl, pyrido[2,3-b]pyrazinyl, imidazo[4,5-c]pyridinyl, benzothiadiazolyl, tetrahydropyrazolo[1,5-a]pyridinyl, dihydrobenzodioxinyl, imidazolyl, dihydrobenzofuranyl, triazolyl, oxazolyl, isoxazolyl, benzodioxinyl, thiazolyl, imidazo[1,2-a]pyridinyl, tetrahydrobenzothiazolyl, dihydrobenzoxazinyl, tetrahydropyranyl, tetrahydropyrazolo[1,5-a]azepinyl, and dihydropyrrolo[1,2-b]pyrazolyl.

More preferably, R is selected from the group consisting of isopropyl, cyclobutyl, cyclopentyl, and tetrahydro-2H-pyranyl; $R_1$ is hydrogen; $R_2$ is $ER_5$; $R_3$ is methyl or ethyl; E is —CH$_2$—; and $R_5$ is selected from the group consisting of phenyl, pyrimidin-2-yl, pyridin-2-yl, pyrazin-2-yl, and 5-methylpyrazin-2-yl.

In other preferred embodiments, the compound is:
6-[(3,4-trans)-1-benzyl-4-methylpyrrolidin-3-yl]-1-(2-methoxyphenyl)-1,5-dihydro-4H-pyrazolo [3,4-d]pyrimidin-4-one
6-[(3,4-trans)-1-benzyl-4-methylpyrrolidin-3-yl]-1-cyclopentyl-1,5-dihydro-4H-pyrazolo [3,4-d]pyrimidin-4-one;
6-[(3S,4S)-1-benzyl-4-methylpyrrolidin-3-yl]-1-cyclopentyl-1,5-dihydro-4H-pyrazolo [3,4-d]pyrimidin-4-one;
1-cyclopentyl-6-[(3,4-trans)-4-methyl-1-pyrimidin-2-ylpyrrolidin-3-yl]-1,5-dihydro-4H-pyrazolo [3,4-d]pyrimidin-4-one;
1-cyclopentyl-6-{(3,4-trans)-4-methyl-1-[4-(trifluoromethyl)pyrimidin-2-yl]pyrrolidin-3-yl}-1,5-dihydro-4H-pyrazolo[3,4-d]pyrimidin-4-one;
6-[(3,4-trans)-1-benzoyl-4-methylpyrrolidin-3-yl]-1-cyclopentyl-1,5-dihydro-4H-pyrazolo [3,4-d]pyrimidin-4-one;
1-cyclopentyl-6-[(3,4-trans)-4-methyl-1-(pyridin-3-ylmethyl)pyrrolidin-3-yl]-1,5-dihydro-4H-4H-pyrazolo [3,4-d]pyrimidin-4-one;
1-cyclopentyl-6-{(3,4-trans)-4-methyl-1-[3-(trifluoromethyl)benzyl]pyrrolidin-3-yl}1,5-dihydro-4H -pyrazolo [3,4-d]pyrimidin-4-one;
1-cyclopentyl-6-[(3,4-trans)-4-methyl-1-(quinolin-2-ylmethyl)pyrrolidin-3-yl]-1,5-dihydro-4H-pyrazolo [3,4-d]pyrimidin-4-one;
1-cyclopentyl-6-[(3,4-trans)-4-methyl-1-(quinolin-4-ylmethyl)pyrrolidin-3-yl]-1,5-dihydro-4H-pyrazolo [3,4-d]pyrimidin-4-one;
1-cyclopentyl-6-[(3,4-trans)-4-methyl-1-{[6-(trifluoromethyl)pyridin-3-yl]methyl}pyrrolidin-3-yl]-1,5-dihydro-4H-pyrazolo[3,4-d]pyrimidin-4-one;
1-cyclopentyl-6-[(3,4-trans)-4-methyl-1-(quinoxalin-2-ylmethyl)pyrrolidin-3-yl]-1,5-dihydro-4H-pyrazolo[3,4-d]pyrimidin-4-one;
1-cyclopentyl-6-[(3,4-trans)-4-methyl-1-(quinoxalin-6-ylmethyl)pyrrolidin-3-yl]-1,5-dihydro-4H-pyrazolo[3,4-d]pyrimidin-4-one;
1-cyclopentyl-6-[(3,4-trans)-4-methyl-1-(pyrimidin-5-ylmethyl)pyrrolidin-3-yl]-1,5-dihydro-4H-pyrazolo[3,4-d]pyrimidin-4-one;
1-cyclopentyl-6-[(3,4-trans)-1,4-dimethylpyrrolidin-3-yl]-1,5-dihydro-4H-pyrazolo[3,4-d]pyrimidin-4-one;
1-cyclopentyl-6-[(3,4-trans)-4-methyl-1-(2,2,2-trifluoroethyl)pyrrolidin-3-yl]-1,5-dihydro-4H-pyrazolo[3,4-d]pyrimidin-4-one;
1-cyclopentyl-6-(3,4-trans)-4-methyl-1-[(2-methylpyridin-3-yl)methyl]pyrrolidin-3-yl)-1,5-dihydro-4H-pyrazolo [3,4-d]pyrimidin-4-one;
1-cyclopentyl-6-[(3,4-trans)-4-methyl-1-(quinolin-8-ylmethyl)pyrrolidin-3-yl]-1,5-dihydro-4H-pyrazolo[3,4-d]pyrimidin-4-one;
1-cyclopentyl-6-[(3,4-trans)-4-methyl-1-(quinolin-3-ylmethyl)pyrrolidin-3-yl]-1,5-dihydro-4H-pyrazolo[3,4-d]pyrimidin-4-one;
1-cyclopentyl-6-{(3,4-trans)-4-methyl-1-[(6-methylpyridin-3-yl)methyl]pyrrolidin-3-yl}-1,5-dihydro-4H-pyrazolo [3,4-d]pyrimidin-4-one;
6-[(3,4-trans)-1-benzyl-4-isopropylpyrrolidin-3-yl]-1-cyclopentyl-1,5-dihydro-4H-pyrazolo[3,4-d]pyrimidin-4-one;
6-[(3,4-trans)-1-benzyl-4-methylpyrrolidin-3-yl]-1-cyclopentyl-3-methyl-1,5-dihydro-4H-pyrazolo[3,4-d]pyrimidin-4-one;

1-cyclopentyl-6-[(3S,4S)-4-methyl-1-(quinoxalin-6-ylmethyl)pyrrolidin-3-yl]-1,5-dihydro-4H-pyrazolo[3,4-d]pyrimidin-4-one;

1-cyclopentyl-6-[(3,4-trans)-4-methyl-1-(2-phenylethyl)pyrrolidin-3-yl]-1,5-dihydro-4H-pyrazolo[3,4-d]pyrimidin-4-one;

1-cyclopentyl-6-{(3,4-trans)-1-[(6-methoxypyridin-3-yl)methyl]-4-methylpyrrolidin-3-yl}-1,5-dihydro-4H-pyrazolo[3,4-d]pyrimidin-4-one;

1-cyclopentyl-6-[(3,4-trans)-4-methyl-1-(pyridin-2-ylmethyl)pyrrolidin-3-yl]-1,5-dihydro-4H-pyrazolo[3,4-d]pyrimidin-4-one;

1-cyclopentyl-6-{(3,4-trans)-4-methyl-1-[(3-methylpyridin-2-yl)methyl]pyrrolidin-3-yl}-1,5-dihydro-4H-pyrazolo[3,4-d]pyrimidin-4-one;

6-[(3,4-trans)-1-benzyl-4-ethylpyrrolidin-3-yl]-1-cyclopentyl-1,5-dihydro-4H-pyrazolo[3,4-d]pyrimidin-4-one;

6-[(3,4-trans)-1-benzyl-4-cyclopropylpyrrolidin-3-yl]-1-cyclopentyl-1,5-dihydro-4H-pyrazolo[3,4-d]pyrimidin-4-one;

6-[(3,4-trans)-1-benzyl-4-methylpyrrolidin-3-yl]-1-isopropyl-1,5-dihydro-4H-pyrazolo[3,4-d]pyrimidin-4-one;

6-[(3S,4S)-1-benzyl-4-methylpyrrolidin-3-yl]-1-isopropyl-1,5-dihydro-4H-pyrazolo[3,4-d]pyrimidin-4-one;

1-isopropyl-6-[(3,4-trans)-4-methyl-1-(quinolin-2-ylmethyl)pyrrolidin-3-yl]-1,5-dihydro-4H-pyrazolo[3,4-d]pyrimidin-4-one;

1-isopropyl-6-[(3,4-trans)-4-methyl-1-(quinoxalin-6-ylmethyl)pyrrolidin-3-yl]-1,5-dihydro-4H-pyrazolo[3,4-d]pyrimidin-4-one;

1-isopropyl-6-[(3,4-trans)-4-methyl-1-(quinolin-3-ylmethyl)pyrrolidin-3-yl]-1,5-dihydro-4H-pyrazolo[3,4-d]pyrimidin-4-one;

6-[(3,4-trans)-1-benzyl-4-(trifluoromethyl)pyrrolidin-3-yl]-1-cyclopentyl-1,5-dihydro-4H-pyrazolo [3,4-d]pyrimidin-4-one;

1-isopropyl-6-[(3S,4S)-4-methyl-1-(quinoxalin-6-ylmethyl)pyrrolidin-3-yl]-1,5-dihydro-4H-pyrazolo[3,4-d]pyrimidin-4-one;

1-isopropyl-6-[(3S,4S)-4-methyl-1-(quinolin-3-ylmethyl)pyrrolidin-3-yl]-1,5-dihydro-4H-pyrazolo[3,4-d]pyrimidin-4-one;

1-cyclopentyl-6-{(3S,4S)-4-methyl-1-[(5-methylpyrazin-2-yl)methyl]pyrrolidin-3-yl}-1,5-dihydro-4H-pyrazolo[3,4-d]pyrimidin-4-one;

6-[(3,4-trans)-1-benzyl-4-ethylpyrrolidin-3-yl]-1-isopropyl-1,5-dihydro-4H-pyrazolo[3,4-d]pyrimidin-4-one;

6-[(3S,4S)-1-benzyl-4-ethylpyrrolidin-3-yl]-1-isopropyl-1,5-dihydro-4H-pyrazolo[3,4-d]pyrimidin-4-one;

1-isopropyl-6-{(3S,4S)-4-methyl-1-[(2-methylpyrimidin-5-yl)methyl]pyrrolidin-3-yl}-1,5-dihydro-4H-pyrazolo[3,4-d]pyrimidin-4-one;

6-(1-benzylpyrrolidin-3-yl)-1-cyclopentyl-1,5-dihydro-4H-pyrazolo[3,4-d]pyrimidin-4-one;

1-isopropyl-6-(3S,4S)-1-[(6-methoxypyridin-3-yl)methyl]-4-methylpyrrolidin-3-yl-1,5-dihydro-4H-pyrazolo[3,4-d]pyrimidin-4-one;

6-[(3,4-trans)-4-ethyl-1-(quinolin-3-ylmethyl)pyrrolidin-3-yl]-1-isopropyl-1,5-dihydro-4H-pyrazolo[3,4-d]pyrimidin-4-one;

6-{(3,4-trans)-4-ethyl-1-[(6-methoxypyridin-3-yl)methyl]pyrrolidin-3-yl}-1-isopropyl-1,5-dihydro-4H-pyrazolo[3,4-d]pyrimidin-4-one;

6-[(3,4-trans)-4-ethyl-1-(quinoxalin-6-ylmethyl)pyrrolidin-3-yl]-1-isopropyl-1,5-dihydro-4H-pyrazolo[3,4-d]pyrimidin-4-one;

1-cyclopentyl-6-{(3S,4S)-1-[(1,3-dimethyl-1H-pyrazol-5-yl)methyl]-4-methylpyrrolidin-3-yl}-1,5-dihydro-4H-pyrazolo[3,4-d]pyrimidin-4-one;

1-cyclopentyl-6-[(3S,4S)-4-methyl-1-(4,5,6,7-tetrahydropyrazolo[1,5-a]pyridin-3-ylmethyl) pyrrolidin-3-yl]-1,5-dihydro-4H-pyrazolo[3,4-d]pyrimidin-4-one;

1-cyclopentyl-6-{(3S,4S)-4-methyl-1-[(1-methyl-1H-benzimidazol-2-yl) methyl]pyrrolidin-3-yl}-1,5-dihydro-4H-pyrazolo[3,4-d]pyrimidin-4-one;

1-isopropyl-6-{(3S,4S)-4-methyl-1-[(5-methylpyrazin-2-yl)methyl]pyrrolidin-3-yl}-1,5-dihydro-4H-pyrazolo[3,4-d]pyrimidin-4-one;

6-[(3S,4S)-1-(cinnolin-3-ylmethyl)-4-methylpyrrolidin-3-yl]-1-cyclopentyl-1,5-dihydro-4H-pyrazolo[3,4-d]pyrimidin-4-one;

1-cyclopentyl-6-[(3,4-trans)-1-(quinoxalin-6-ylmethyl)-4-(trifluoromethyl)pyrrolidin-3-yl]-1,5-dihydro-4H-pyrazolo[3,4-d]pyrimidin-4-one;

1-cyclopentyl-6-{(3S,4S)-4-methyl-1-[(2-methylpyrimidin-4-yl)methyl]pyrrolidin-3-yl}-1,5-dihydro-4H-pyrazolo[3,4-d]pyrimidin-4-one;

1-cyclopentyl-6-[(3S,4S)-1-{[2-(dimethylamino)pyrimidin-4-yl]methyl}-4-methylpyrrolidin-3-yl]-1,5-dihydro-4H-pyrazolo[3,4-d]pyrimidin-4-one;

1-cyclopentyl-6-{(3,4-trans)-4-cyclopropyl-1-[(5-methylpyrazin-2-yl)methyl]pyrrolidin-3-yl}-1,5-dihydro-4H-pyrazolo[3,4-d]pyrimidin-4-one;

1-cyclopentyl-6-[(3,4-trans)-4-cyclopropyl-1-(quinoxalin-6-ylmethyl)pyrrolidin-3-yl]-1,5-dihydro-4H-pyrazolo[3,4-d]pyrimidin-4-one;

1-cyclopentyl-6-[(3,4-trans)-4-cyclopropyl-1-methylpyrrolidin-3-yl]-1,5-dihydro-4H-pyrazolo [3,4-d]pyrimidin-4-one;

6-[(3,4-trans)-1-benzyl-4-methylpyrrolidin-3-yl]-1-ethyl-1,5-dihydro-4H-pyrazolo [3,4-d]pyrimidin-4-one;

6-{(3,4-trans)-4-ethyl-1-[(2-methylpyrimidin-5-yl)methyl]pyrrolidin-3-yl}-1-isopropyl-1,5-dihydro-4H-pyrazolo [3,4-d]pyrimidin-4-one;

6-[(3,4-trans)-1-benzyl-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-methylpyrrolidin-3-yl]-1-(tetrahydro-2H-pyran-4-yl)-1,5-dihydro-4H-pyrazolo[3,4-d]pyrimidin-4-one;

6-[(3,4-trans)-1-benzyl-4-(2,2,2-trifluoroethyl)pyrrolidin-3-yl]-1-cyclopentyl-1,5-dihydro-4H-pyrazolo[3,4-d]pyrimidin-4-one;

6-[(3,4-trans)-1-benzyl-4-methylpyrrolidin-3-yl]-1-(4,4-difluorocyclohexyl)-1,5-dihydro-4H-pyrazolo[3,4-d]pyrimidin-4-one;

6-[(3,4-trans)-1-benzyl-4-methylpyrrolidin-3-yl]-1-(2,2,2-trifluoroethyl)-1,5-dihydro-4H-pyrazolo [3,4-d]pyrimidin-4-one;

1-isopropyl-6-[(3S,4S)-4-methyl-1-(1,5-naphthyridin-4-ylmethyl)pyrrolidin-3-yl]-1,5-dihydro-4H-pyrazolo[3,4-d]pyrimidin-4-one;

1-isopropyl-6-[(3S,4S)-4-methyl-1-(1,8-naphthyridin-4-ylmethyl)pyrrolidin-3-yl]-1,5-dihydro-4H-pyrazolo[3,4-d]pyrimidin-4-one;

1-isopropyl-6-[3S,4S)-4-methyl-1-(quinolin-4-ylmethyl)pyrrolidin-3-yl]-1,5-dihydro-4H-pyrazolo[3,4-d]pyrimidin-4-one;

1-isopropyl-6-[(3S,4S)-4-methyl-1-(pyrido[2,3-b]pyrazin-8-ylmethyl)pyrrolidin-3-yl]-1,5-dihydro-4H-pyrazolo[3,4-d]pyrimidin-4-one;

1-isopropyl-6-{(3,4-trans)-1-[(6-methoxy-1,5-naphthyridin-4-yl)methyl]-4-methylpyrrolidin-3-yl}-1,5-dihydro-4H-pyrazolo[3,4-d]pyrimidin-4-one;

6-{(3,4-trans)-1-[(8-fluoroquinolin-2-yl)methyl]-4-methylpyrrolidin-3-yl}-1-isopropyl-1,5-dihydro-4H-pyrazolo[3,4-d]pyrimidin-4-one;

1-isopropyl-6-{(v)-1-[(6-methoxyquinolin-4-yl)methyl]-4-methylpyrrolidin-3-yl}-1,5-dihydro-4H-pyrazolo[3,4-d]pyrimidin-4-one;

6-[(3,4-trans)-1-benzyl-4-methylpyrrolidin-3-yl]-1-cyclobutyl-1,5-dihydro-4H-pyrazolo[3,4-d]pyrimidin-4-one;

6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one;

6-{(3,4-trans)-4-ethyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-4-methyl-1-[(5-methylpyrazin-2-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-1-[(6-methoxypyridin-3-yl)methyl]-4-methylpyrrolidin-3-yl}-1-(tetrahydro-2H-pyran-4-yl)-1,5-dihydro-4H-pyrazolo[3,4-d]pyrimidin-4-one;

6-[(3S,4S )-4-methyl-1-(quinolin-3-ylmethyl)pyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[(2-methylpyrimidin-4-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-4-methyl-1-[(6-methylpyridin-3-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-4-methyl-1-}([6-(trifluoromethyl)pyridin-3-yl]methyl}pyrrolidin-3-yl}-1-(tetrahydro-2H-pyran-4-yl)-1,5-dihydro-4H-pyrazolo[3,4-d]pyrimidin-4-one;

6-{(3S,4S)-4-methyl-1-[(1-methyl-1H-imidazo[4,5-c]pyridin-2-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-1-[(1,3-dimethyl-1H-pyrazol-5-yl)methyl]-4-methylpyrrolidin-3-yl}-1-(tetrahydro-2H-pyran-4-yl)-1,5-dihydro-4H-pyrazolo[3,4-d]pyrimidin-4-one;

1-cyclobutyl-6-{(3,4-trans)-4-methyl-1-[(2-methylpyrimidin-5-yl)methyl]pyrrolidin-3-yl}-1,5-dihydro-4H-pyrazolo[3,4-d]pyrimidin-4-one;

6-[(3S,4S)-1-(2,1,3-benzothiadiazol-5-ylmethyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-4-methyl-1-(quinoxalin-2-ylmethyl)pyrrolidin-3-yl]-1-(tetrahydro-2H-pyran-4-yl)-1,5-dihydro-4H-pyrazolo[3,4-d]pyrimidin-4-one;

6-[(3S,4S)-4-methyl-1-(quinolin-4-ylmethyl)pyrrolidin-3-yl]-1-tetrahydro-2H-pyran-4-yl)-1,5-dihydro-4H-pyrazolo[3,4-d]pyrimidin-4-one;

6-[(3S,4S)-4-methyl-1-(pyridin-2-ylmethyl)pyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-methylpyrrolidin-3-yl]-3-methyl-1-(tetrahydro-2H-pyran-4-yl)-1,5-dihydro-4H-pyrazolo[3,4-d]pyrimidin-4-one;

6-[(3S,4S)-1-(3-fluorobenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(35-difluorobenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[4-(trifluoromethyl)benzyl]pyrrolidin-3-yl}-1-(tetrahydro-2H-pyran-4-y)-1,5-dihydro-4H-pyrazolo[3,4-d]pyrimidin-4-one;

6-[(3,4-trans)-1-benzyl-4-ethylpyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-ethylpyrrolidin-3-yl]-1-(tetrahydro-2H-pyran-4-yl)-1,5-dihydro-4H-pyrazolo[3,4-d]pyrimidin-4-one;

3-methyl-6-[(3S,4S)-4-methyl-1-(pyridin-3-ylmethyl)pyrrolidin-3-yl]-1-(tetrahydro-2H-pyran-4-yl)-1,5-dihydro-4H-pyrazolo[3,4-d]pyrimidin-4-one;

3-methyl-6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-1-[(6-methoxypyridin-3-yl)methyl]-4-methylpyrrolidin-3-yl}-3-methyl-1-(tetrahydro-2H-pyran-4-yl)-1,5-dihydro-4H-pyrazolo[3,4-d]pyrimidin-4-one;

6-{(3S,4S)-4-methyl-1-[(6-methylpyridin-2-yl)methyl]pyrrolidin-3-yl}-1-(tetrahydro-2H-pyran-4-yl)-1,5-dihydro-4H-pyrazolo[3,4-d]pyrimidin-4-one;

6-[(3S,4S)-1-(4-fluorobenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(2-fluorobenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[2-(trifluoromethyl)benzyl]pyrrolidin-3-yl}-1-(tetrahydro-2H-pyran-4-yl)-1,5-dihydro-4H-pyrazolo[3,4-d]pyrimidin-4-one;

6-[(3S,4S)-1-(2,4-difluorobenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(4-methoxybenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-methylpyrrolidin-3-yl]-1-(tetrahydro-2H-thiopyran-4-yl)-1,5-dihydro-4H-pyrazolo[3,4-d]pyrimidin-4-one;

6-[(3S,4S)-1-(2-methoxybenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(3-methoxybenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[3-(trifluoromethyl)benzyl]pyrrolidin-3-yl}-1-(tetrahydro-2H-pyran-4-yl)-1,5-dihydro-4H-pyrazolo[3,4-d]pyrimidin-4-one;

6-[(3S,4S)-1-(26-difluorobenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-ethyl-1-[(5-methylpyrazin-2-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-4-ethyl-1-[(6-methoxypyridin-3-yl)methyl]pyrrolidin-3-yl}-1-(tetrahydro-2H-pyran-4-yl)-1,5-dihydro-4H-pyrazolo[3,4-d]pyrimidin-4-one;

6-[(3S,4S)-4-ethyl-1-(pyridin-2-ylmethyl)pyrrolidin-3-yl]-1-(tetrahydro-2H-pyran-4-yl)-1,5-dihydro-4H-pyrazolo[3,4-d]pyrimidin-4-one;

6-[(3S,4S)-4-ethyl-1-(quinoxalin-2-ylcarbonyl)pyrrolidin-3-yl]-1-(tetrahydro-2H-pyran-4-yl)-1,5-dihydro-4H-pyrazolo[3,4-d]pyrimidin-4-one;

6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one;

2-({(3S,4S)-3-ethyl-4-[4-oxo-1-(tetrahydro-2H-pyran-4-yl)-45-dihydro-1H-pyrazolo[3,4-d]pyrimidin-6-yl]pyrrolidin-1-yl}methyl)benzonitrile;

3-({(3S,4S)-3-ethyl-4-[4-oxo-1-(tetrahydro-2H-pyran-4-yl)-45-dihydro-1H-pyrazolo[3,4-d]pyrimidin-6-yl]pyrrolidin-1-yl}methyl)benzonitrile;

4-({(3S,4S)-3-ethyl-4-[4-oxo-1-(tetrahydro-2H-pyran-4-yl)-45-dihydro-1H-pyrazolo[3,4-d]pyrimidin-6-yl]pyrrolidin-1-yl}methyl)benzonitrile;

1-cyclopentyl-6-(3,4-trans)-4-methyl-1-[3-(1H-pyrazol-1-yl)benzyl]pyrrolidin-3-yl]-1,5-dihydro-4H-pyrazolo[3,4-d]pyrimidin-4-one;

1-cyclopentyl-6-{(3,4-trans)-4-methyl-1-[(2-methylpyridin-4-yl)methyl]pyrrolidin-3-yl}-1,5-dihydro-4H-pyrazolo[3,4-d]pyrimidin-4-one;

6-[(3,4-trans)-1-(2-chloro-6-fluorobenzyl)-4-methylpyrrolidin-3-yl]-1-cyclopentyl-1,5-dihydro-4H-pyrazolo[3,4-d]pyrimidin-4-one;

1-cyclopentyl-6-[(3,4-trans)-1-(2,3-dimethylbenzyl)-4-methylpyrrolidin-3-yl]-1,5-dihydro-4H-pyrazolo[3,4-d]pyrimidin-4-one;

1-cyclopentyl-6-{(3,4-trans)-1-[2-(difluoromethoxy)benzyl]-4-methylpyrrolidin-3-yl}-1,5-dihydro-4H-pyrazolo[3,4-]pyrimidin-4-one 1-cyclopentyl-6-{(3,4-trans)-1-[(2-ethoxypyridin-3-yl)methyl]-4-methylpyrrolidin-3-yl}-1,5-dihydro-4H-pyrazolo[3,4-d]pyrimidin-4-one;

1-cyclopentyl-6-[(3,4-trans)-4-methyl-1-(4,5,6,7-tetrahydropyrazolo[1,5-a]pyridin-3-ylmethyl)pyrrolidin-3-yl]-1,5-dihydro-4H-pyrazolo[3,4-d]pyrimidin-4-one;

1-cyclopentyl-6-[(3,4-trans)-1-(2,3-dihydro-1,4-benzodioxin-6-ylmethyl)-4-methylpyrrolidin-3-yl]-1,5-dihydro-4H-pyrazolo[3,4-d]pyrimidin-4-one;

1-cyclopentyl-6-{(3,4-trans)-1-[4-(1H-imidazol-1-yl)benzyl]-4-methylpyrrolidin-3-yl}-1,5-dihydro-4H-pyrazolo[3,4-d]pyrimidin-4-one;

1-cyclopentyl-6-[(3,4-trans)-1-(2,5-dichlorobenzyl)-4-methylpyrrolidin-3-yl]-1,5-dihydro-4H-pyrazolo[3,4-d]pyrimidin-4-one;

1-cyclopentyl-6-[(3,4-trans)-1-(4-methoxy-3-methylbenzyl)-4-methylpyrrolidin-3-yl]-1,5-dihydro-4H-pyrazolo[3,4-d]pyrimidin-4-one;

1-cyclopentyl-6-[(3,4-trans)-1-(2,3-dihydro-1-benzofuran-7-ylmethyl)-4-methylpyrrolidin-3-yl]-1,5-dihydro-4H-pyrazolo[3,4-d]pyrimidin-4-one;

1-cyclopentyl-6-[(3,4-trans)-1-(2,3-difluorobenzyl)-4-methylpyrrolidin-3-yl]-1,5-dihydro-4H-pyrazolo[3,4-d]pyrimidin-4-one;

1-cyclopentyl-6-[(3,4-trans)-1-(5-fluoro-2-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(2-fluoro-4-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(3-fluoro-4-methylbenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(2-methyl-1,3-thiazol-5-yl)methyl]pyrrolidin-3-yl}-1,5-dihydro-4H-pyrazolo[3,4-d]pyrimidin-4-one;

1-cyclopentyl-6-{(3,4-trans)-1-[(4-isopropyl-1,3-thiazol-2-yl)methyl]-4-methylpyrrolidin-3-yl}-1,5-dihydro-4H-pyrazolo[3,4-d]pyrimidin-4-one;

1-cyclopentyl-6-{(3,4-trans)-1-[(1,3-dimethyl-1H-pyrazol-5-yl)methyl]-4-methylpyrrolidin-3-yl}-1,5-dihydro-4H-pyrazolo[3,4-d]pyrimidin-4-one;

1-cyclopentyl-6-[(3,4-trans)-1-(2,3-difluoro-4-methylbenzyl)-4-methylpyrrolidin-3-yl]-1,5-dihydro-4H-pyrazolo[3,4-d]pyrimidin-4-one;

1-cyclopentyl-6-[(3,4-trans)-4-methyl-1-{[6-(1H-pyrazol-1-yl)pyridin-2-yl]methyl}pyrrolidin-3-yl]-1,5-dihydro-4H-pyrazolo[3,4-d]pyrimidin-4-one;

1-cyclopentyl-6-[(3,4-trans)-4-methyl-1-(4-methylbenzyl)pyrrolidin-3-yl]-1,5-dihydro-4H-pyrazolo[3,4-d]pyrimidin-4-one;

1-cyclopentyl-6-[(3,4-trans)-4-methyl-1-(2-naphthylmethyl)pyrrolidin-3-yl]-1,5-dihydro-4H-pyrazolo[3,4-d]pyrimidin-4-one;

1-cyclopentyl-6-{(3,4-trans)-1-[(2-methoxypyridin-3-yl)methyl]-4-methylpyrrolidin-3-yl}-1,5-dihydro-4H-pyrazolo[3,4-d]pyrimidin-4-one;

1-cyclopentyl-6-[(3,4-trans)-1-(2-ethoxybenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[4-(1H-1,2,4-triazol-1-yl)benzyl]pyrrolidin-3-yl}-1,5-dihydro-4H-pyrazolo[3,4-d]pyrimidin-4-one;

1-cyclopentyl-6-[(3,4-trans)-1-(3-methoxy-4-methylbenzyl)-4-methylpyrrolidin-3-yl]-1,5-dihydro-4H-pyrazolo[3,4-d]pyrimidin-4-one;

1-cyclopentyl-6-[(3,4-trans)-4-methyl-1-(1-naphthylmethyl)pyrrolidin-3-yl]-1,5-dihydro-4H-pyrazolo[3,4-d]pyrimidin-4-one;

1-cyclopentyl-6-[(3,4-trans)-1-(3-fluoro-4-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(2,5-dimethoxybenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(5-methylisoxazol-3-yl)methyl]pyrrolidin-3-yl}-1,5-dihydro-4H-pyrazolo[3,4-d]pyrimidin-4-one;

1-cyclopentyl-6-[(3,4-trans)-1-(2-fluoro-6-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(2,4-difluorobenzyl)-4-methylpyrrolidin-3-yl]-1,5-dihydro-4H-pyrazolo[3,4-d]pyrimidin-4-one;

1-cyclopentyl-6-[(3,4-trans)-1-(4-fluoro-3-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(2,3-dihydro-1,4-benzodioxin-5-ylmethyl)-4-methylpyrrolidin-3-yl]-1,5-dihydro-4H-pyrazolo[3,4-d]pyrimidin-4-one;

6-[(3,4-trans)-1-(2-chloro-4-fluorobenzyl)-4-methylpyrrolidin-3-yl]-1-cyclopentyl-1,5-dihydro-4H-pyrazolo[3,4-d]pyrimidin-4-one;

1-cyclopentyl-6-[(3,4-trans)-1-(2,4-dimethylbenzyl)-4-methylpyrrolidin-3-yl]-1,5-dihydro-4H-pyrazolo[3,4-d]pyrimidin-4-one;

1-cyclopentyl-6-[(3,4-trans)-1-(3,5-dimethoxybenzyl)-4-methylpyrrolidin-3-yl]-1,5-dihydro-4H-pyrazolo[3,4-d]pyrimidin-4-one;

1-cyclopentyl-6-[(3,4-trans)-1-(3-ethoxybenzyl)-4-methylpyrrolidin-3-yl]-1,5-dihydro-4H-pyrazolo[3,4-d]pyrimidin-4-one;

6-[(3,4-trans)-1-(4-chloro-2-fluorobenzyl)-4-methylpyrrolidin-3-yl]-1-cyclopentyl-1,5-dihydro-4H-pyrazolo[3,4-d]pyrimidin-4-one;

3-{[(3,4-trans)-3-(1-cyclopentyl-4-oxo-4,5-dihydro-1H-pyrazolo[3,4-d]pyrimidin-6-yl)-4-methylpyrrolidin-1-yl]methyl}benzonitrile;

1-cyclopentyl-6-[(3,4-trans)-1-(2,5-difluorobenzyl)-4-methylpyrrolidin-3-yl]-1,5-dihydro-4H-pyrazolo[3,4-d]pyrimidin-4-one;

2-{[(3,4-trans)-3-(1-cyclopentyl-4-oxo-4,5-dihydro-1H-pyrazolo[3,4-d]pyrimidin-6-yl)-4-methylpyrrolidin-1-yl]methyl}benzonitrile;

6-[(3,4-trans)-1-(3-chloro-4-fluorobenzyl)-4-methylpyrrolidin-3-yl]-1-cyclopentyl-1,5-dihydro-4H-pyrazolo[3,4-d]pyrimidin-4-one;

1-cyclopentyl-6-{(3,4-trans)-1-[4-(difluoromethoxy)benzyl]-4-methylpyrrolidin-3-yl}-1,5-dihydro-4H-pyrazolo[3,4-d]pyrimidin-4-one;

1-cyclopentyl-6-[(3,4-trans)-4-methyl-1-(3-methylbenzyl)pyrrolidin-3-yl]-1,5-dihydro-4H-pyrazolo[3,4-d]pyrimidin-4-one;

1-cyclopentyl-6-[(3,4-trans)-1-(3,4-difluorobenzyl)-4-methylpyrrolidin-3-yl]-1,5-dihydro-4H-pyrazolo[3,4-d]pyrimidin-4-one;

1-cyclopentyl-6-[(3,4-trans)-1-(2,5-dimethylbenzyl)-4-methylpyrrolidin-3-yl]-1,5-dihydro-4H-pyrazolo[3,4-d]pyrimidin-4-one;

6-[(3,4-trans)-1-(3-chloro-2-fluorobenzyl)-4-methylpyrrolidin-3-yl]-1-cyclopentyl-1,5-dihydro-4H-pyrazolo[3,4-d]pyrimidin-4-one;

1-cyclopentyl-6-[(3,4-trans)-1-(2,3-dichlorobenzyl)-4-methylpyrrolidin-3-yl]-1,5-dihydro-4H-pyrazolo[3,4-d]pyrimidin-4-one;

1-cyclopentyl-6-[(3,4-trans)-4-methyl-1-(1,3-thiazol-2-ylmethyl)pyrrolidin-3-yl]-1,5-dihydro-4H-pyrazolo[3,4-d]pyrimidin-4-one;

1-cyclopentyl-6-[(3,4-trans)-1-(3-fluoro-2-methylbenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(2-methylpyrimidin-5-yl)methyl]pyrrolidin-3-yl}-1,5-dihydro-4H-pyrazolo[3,4-d]pyrimidin-4-one;

1-cyclopentyl-6-{(3,4-trans)-1-[(2-ethylpyrimidin-5-yl)methyl]-4-methylpyrrolidin-3-yl}-1,5-dihydro-4H-pyrazolo[3,4-d]pyrimidin-4-one;

1-cyclopentyl-6-[(3,4-trans)-1-(4-isopropylbenzyl)-4-methylpyrrolidin-3-yl]-1,5-dihydro-4H-pyrazolo[3,4-d]pyrimidin-4-one;

1-cyclopentyl-6-{(3,4-trans-1-[(1-ethyl-1H-pyrazol-4-yl)methyl]-4-methylpyrrolidin-3-yl}-1,5-dihydro-4H-pyrazolo[3,4-d]pyrimidin-4-one;

1-cyclopentyl-6-{(3,4-trans)-1-[(4-methoxypyridin-3-yl)methyl]-4-methylpyrrolidin-3-yl}-1,5-dihydro-4H-pyrazolo[3,4-d]pyrimidin-4-one;

1-cyclopentyl-6-[(3,4-trans)-1-(isoxazol-5-ylmethyl)-4-methylpyrrolidin-3-yl]-1,5-dihydro-4H-pyrazolo[3,4-d]pyrimidin-4-one;

1-cyclopentyl-6-[(3,4-trans)-1-(4-ethoxybenzyl)-4-methylpyrrolidin-3-yl]-1,5-dihydro-4H-pyrazolo[3,4-d]pyrimidin-4-one;

1-cyclopentyl-6-[(3,4-trans)-1-{[6-(1-hydroxy-1-methylethyl)pyridin-3-yl]methyl}-4-methylpyrrolidin-3-yl]-1,5-dihydro-4H-pyrazolo[3,4-d]pyrimidin-4-one;

1-cyclopentyl-6-{(3,4-trans)-1-[(2,2-dimethyl-2,3-dihydro-1-benzofuran-5-yl)methyl]-4-methylpyrrolidin-3-yl}-1,5-dihydro-4H-pyrazolo[3,4-d]pyrimidin-4-one;

1-cyclopentyl-6-[(3,4-trans)-1-(3,4-dimethoxybenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(5-methylpyrazin-2-yl)methyl]pyrrolidin-3-yl}-1,5-dihydro-4H-pyrazolo[3,4-d]pyrimidin-4-one;

1-cyclopentyl-6-[(3,4-trans)-1-(imidazo[1,2-a]pyridin-2-ylmethyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(2-phenyl-1,3-oxazol-4-yl)methyl]pyrrolidin-3-yl}-1,5-dihydro-4H-pyrazolo[3,4-d]pyrimidin-4-one;

1-cyclopentyl-6-[(3,4-trans)-4-methyl-1-(2-methylbenzyl)pyrrolidin-3-yl]-1,5-dihydro-4H-pyrazolo[3,4-d]pyrimidin-4-one;

1-cyclopentyl-6-[(3,4-trans)-1-(2-isopropoxybenzyl)-4-methylpyrrolidin-3-yl]-1,5-dihydro-4H-pyrazolo[3,4-d]pyrimidin-4-one;

6-[(3,4-trans)-1-(cinnolin-3-ylmethyl)-4-methylpyrrolidin-3-yl]-1-cyclopentyl-1,5-dihydro-4H-pyrazolo[3,4-d]pyrimidin-4-one;

1-cyclopentyl-6-{(3,4-trans)-1-[3-(difluoromethoxy)benzyl]-4-methylpyrrolidin-3-yl}-1,5-dihydro-4H-pyrazolo[3,4-d]pyrimidin-4-one;

1-cyclopentyl-6-[(3,4-trans)-1-(4-fluoro-3-methylbenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[4-(1H-pyrazol-1-yl)benzyl]pyrrolidin-3-yl}-1,5-dihydro-4H-pyrazolo[3,4-d]pyrimidin-4-one;

1-cyclopentyl-6-{(3,4-trans)-1-[(2,7-dimethylimidazo[1,2-a]pyridin-3-yl)methyl]-4-methylpyrrolidin-3-yl}-1,5-dihydro-4H-pyrazolo[3,4-d]pyrimidin-4-one;

1-cyclopentyl-6-[(3,4-trans)-1-(3,5-dichlorobenzyl)-4-methylpyrrolidin-3-yl]-1,5-dihydro-4H-pyrazolo[3,4-d]pyrimidin-4-one;

1-cyclopentyl-6-[(3,4-trans)-1-(4-isopropoxybenzyl)-4-methylpyrrolidin-3-yl]-1,5-dihydro-4H-pyrazolo[3,4-d]pyrimidin-4-one;

1-cyclopentyl-6-[(3,4-trans)-1-{[2-(1-hydroxy-1-methylethyl)pyridin-4-yl]methyl}-4-methylpyrrolidin-3-yl]-1,5-dihydro-4H-pyrazolo[3,4-d]pyrimidin-4-one;

1-cyclopentyl-6-[(3,4-trans)-4-methyl-1-(4,5,6,7-tetrahydro-1,3-benzothiazol-2-ylmethyl)pyrrolidin-3-yl]-1,5-dihydro-4H-pyrazolo[3,4-d]pyrimidin-4-one;

1-cyclopentyl-6-[(3,4-trans)-1-(mesitylmethyl)-4-methylpyrrolidin-3-yl]-1,5-dihydro-4H-pyrazolo[3,4-d]pyrimidin-4-one;

1-cyclopentyl-6-[(3,4-trans)-1-(2,6-dichlorobenzyl)-4-methylpyrrolidin-3-yl]-1,5-dihydro-4H-pyrazolo[3,4-d]pyrimidin-4-one;

4-{[(3,4-trans)-3-(1-cyclopentyl-4-oxo-4,5-dihydro-1H-pyrazolo[3,4-d]pyrimidin-6-yl)-4-methylpyrrolidin-1-yl]methyl}benzonitrile;

1-cyclopentyl-6-[(3,4-trans)-1-(2-fluoro-5-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(2,6-dimethylbenzyl)-4-methylpyrrolidin-3-yl]-1,5-dihydro-4H-pyrazolo[3,4-d]pyrimidin-4-one;

1-cyclopentyl-6-{(3,4-trans)-1-[(4-methoxy-3,5-dimethylpyridin-2-yl)methyl]-4-methylpyrrolidin-3-yl}-1,5-dihydro-4H-pyrazolo[3,4-d]pyrimidin-4-one;

1-cyclopentyl-6-[(3,4-trans)-1-(3,5-dimethylbenzyl)-4-methylpyrrolidin-3-yl]-1,5-dihydro-4H-pyrazolo[3,4-d]pyrimidin-4-one;

1-cyclopentyl-6-[(3,4-trans)-1-(3,4-dimethylbenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(1-methyl-1H-benzimidazol-2-yl) methyl]pyrrolidin-3-yl}-1,5-dihydro-4H-pyrazolo[3,4-d]pyrimidin-4-one;

1-cyclopentyl-6-{(3,4-trans)-4-methyl-1-[(4-methyl-3,4-dihydro-2H-1,4-benzoxazin-7-yl)methyl]pyrrolidin-3-yl}-1,5-dihydro-4H-pyrazolo[3,4-d]pyrimidin-4-one;

1-cyclopentyl-6-[(3,4-trans)-4-methyl-1-(3-phenylpropyl)pyrrolidin-3-yl]-1,5-dihydro-4H-pyrazolo[3,4-d]pyrimidin-4-one;

1-cyclopentyl-6-{(3,4-trans)-4-methyl-1-[2-(trifluoromethyl)benzyl]pyrrolidin-3-yl}-1,5-dihydro-4H-pyrazolo[3,4-d]pyrimidin-4-one;

1-cyclopentyl-6-[(3,4-trans)-4-methyl-1-(4,4,4-trifluorobutyl)pyrrolidin-3-yl]-1,5-dihydro-4H-pyrazolo[3,4-d]pyrimidin-4-one;

1-cyclopentyl-6-[(3,4-trans)-1-(3-methoxybenzyl)-4-methylpyrrolidin-3-yl]-1,5-dihydro-4H-pyrazolo[3,4-d]pyrimidin-4-one;

1-cyclopentyl-6-[(3,4-trans)-1-(cyclopentylmethyl)-4-methylpyrrolidin-3-yl]-1,5-dihydro-4H-pyrazolo[3,4-d]pyrimidin-4-one;

1-cyclopentyl-6-[(3,4-trans)-1-(2,4-dimethoxybenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[4-(morpholin-4-ylmethyl)benzyl]pyrrolidin-3-yl}-1,5-dihydro-4H-pyrazolo[3,4-d]pyrimidin-4-one;

6-[(3,4-trans)-1-(2,1,3-benzothiadiazol-5-ylmethyl)-4-methylpyrrolidin-3-yl]-1-cyclopentyl-1,5-dihydro-4H-pyrazolo[3,4-d]pyrimidin-4-one;

6-{(3,4-trans)-1-[2-(benzyloxy)ethyl]-4-methylpyrrolidin-3-yl}-1-cyclopentyl-1,5-dihydro-4H-pyrazolo[3,4-d]pyrimidin-4-one;

1-cyclopentyl-6-[(3,4-trans)-1-(2,6-difluorobenzyl)-4-methylpyrrolidin-3-yl]-1,5-dihydro-4H-pyrazolo[3,4-d]pyrimidin-4-one;

1-cyclopentyl-6-[(3,4-trans)-1-(2-methoxybenzyl)-4-methylpyrrolidin-3-yl]-1,5-dihydro-4H-pyrazolo[3,4-d]pyrimidin-4-one;

1-cyclopentyl-6-{(3,4-trans)-4-methyl-1-[(3,5,6-trimethylpyrazin-2-yl)methyl]pyrrolidin-3-yl}-1,5-dihydro-4H-pyrazolo[3,4-d]pyrimidin-4-one;

1-cyclopentyl-6-[(3,4-trans)-1-(2,4-dichlorobenzyl)-4-methylpyrrolidin-3-yl]-1,5-dihydro-4H-pyrazolo[3,4-d]pyrimidin-4-one;

1-cyclopentyl-6-[(3,4-trans)-4-methyl-1-(5,6,7,8-tetrahydro-4H-pyrazolo[1,5-a]azepin-3-ylmethyl)pyrrolidin-3-yl]-1,5-dihydro-4H-pyrazolo[3,4-d]pyrimidin-4-one;

1-cyclopentyl-6-[(3,4-trans)-1-(3-fluorobenzyl)-4-methylpyrrolidin-3-yl]-1,5-dihydro-4H-pyrazolo[3,4-d]pyrimidin-4-one;

1-cyclopentyl-6-[(3,4-trans)-1-(2,3-dihydro-1-benzofuran-5-ylmethyl)-4-methylpyrrolidin-3-yl]-1,5-dihydro-4H-pyrazolo[3,4-d]pyrimidin-4-one;

1-cyclopentyl-6-[(3,4-trans)-1-(2-methoxy-5-methylbenzyl)-4-methylpyrrolidin-3-yl]-1,5-dihydro-4H-pyrazolo[3,4-d]pyrimidin-4-one;

1-cyclopentyl-6-[(3,4-trans)-1-(2-fluorobenzyl)-4-methylpyrrolidin-3-yl]-1,5-dihydro-4H-pyrazolo[3,4-d]pyrimidin-4-one;

6-[(3,4-trans)-1-(2-chlorobenzyl)-4-methylpyrrolidin-3-yl]-1-cyclopentyl-1,5-dihydro-4H-pyrazolo[3,4-d]pyrimidin-4-one;

1-cyclopentyl-6-[(3,4-trans)-1-(3,4-dichlorobenzyl)-4-methylpyrrolidin-3-yl]-1,5-dihydro-4H-pyrazolo[3,4-d]pyrimidin-4-one;

6-[(3,4-trans)-1-(2,1,3-benzothiadiazol-4-ylmethyl)-4-methylpyrrolidin-3-yl]-1-cyclopentyl-1,5-dihydro-4H-pyrazolo[3,4-d]pyrimidin-4-one;

1-cyclopentyl-6-{(3,4-trans)-4-methyl-1-[(2-propylpyrimidin-5-yl)methyl]pyrrolidin-3-yl}-1,5-dihydro-4H-pyrazolo[3,4-d]pyrimidin-4-one;

1-cyclopentyl-6-{(3,4-trans)-1-[(1-ethyl-1H-pyrazol-5-yl)methyl]-4-methylpyrrolidin-3-yl}-1,5-dihydro-4H-pyrazolo[3,4-d]pyrimidin-4-one;

1-cyclopentyl-6-{(3,4-trans)-4-methyl-1-[2-(trifluoromethoxy)benzyl]pyrrolidin-3-yl}-1,5-dihydro-4H-pyrazolo[3,4-d]pyrimidin-4-one;

1-cyclopentyl-6-{(3,4-trans)-4-methyl-1-[4-(trifluoromethyl)benzyl]pyrrolidin-3-yl}-1,5-dihydro-4H-pyrazolo[3,4-d]pyrimidin-4-one;

1-cyclopentyl-6-{(3,4-trans)-4-methyl-1-[(1-methyl-1H-imidazo[4,5-c]pyridin-2-yl)methyl]pyrrolidin-3-yl}-1,5-dihydro-4H-pyrazolo[3,4-d]pyrimidin-4-one;

1-cyclopentyl-6-[(3,4-trans)-1-(3,5-difluorobenzyl)-4-methylpyrrolidin-3-yl]-1,5-dihydro-4H-pyrazolo[3,4-d]pyrimidin-4-one; or 1-cyclopentyl-6-[(3,4-trans)-1-(5,6-dihydro-4H-pyrrolo[1,2-b]pyrazol-3-ylmethyl)-4-methylpyrrolidin-3-yl]-1,5-dihydro-4H-pyrazolo[3,4-d]pyrimidin-4-one;

or a pharmaceutically acceptable salt thereof.

The compounds of the invention have been surprising found to show pharmacological activity including in selectively inhibiting PDE9 that makes them suitable for the treatment, prevention and/or control of in treating conditions that may be regulated or normalized by inhibition of PDE9.

The compounds and intermediates of the present invention may be named according to either the IUPAC (International Union for Pure and Applied Chemistry) or CAS (Chemical Abstracts Service, Columbus, OH) nomenclature systems.

Definitions

Certain terms used herein are generally defined as follows:

The carbon atom content of the various hydrocarbon-containing moieties herein may be indicated by a prefix designating the minimum and maximum number of carbon atoms in the moiety. Thus, for example, $(C_1-C_6)$alkyl refers to an alkyl group of one to six carbon atoms inclusive.

The term "alkoxy" refers to a straight or branched, monovalent, saturated aliphatic hydrocarbon radical bonded to an oxygen atom that is attached to a core structure. Examples of alkoxy groups include methoxy, ethoxy, propoxy, isopropoxy, butoxy, isobutoxy, tert-butoxy, pentoxy, and the like.

The term "alkyl" means a saturated monovalent straight or branched aliphatic hydrocarbon radical. Examples of alkyl groups include methyl, ethyl, propyl, isopropyl, butyl, isobutyl, tert-butyl, sec-butyl, pentyl, isopentyl, neopentyl, hexyl, isohexyl, and the like.

The term "alkenyl" means a partially unsaturated straight or branched aliphatic hydrocarbon radical having one or more double bonds. Examples of alkenyl groups include ethenyl (also known as "vinyl"), allyl, 1-propenyl, isopropenyl, n-butenyl, n-pentenyl, and the like. The term "alkenyl" embraces radicals having "cis" and "trans" orientations, or alternatively, "Z" and "E" orientations.

The term "alkynyl" means a partially unsaturated straight or branched aliphatic hydrocarbon radical having one or more double bonds. Examples of alkynyl groups include 1-propynyl, 2-propynyl (also known as "propargyl"), 1-butynyl, 2-butynyl, 1-pentynyl, and the like.

The term "aryl" denotes a monocyclic or polycyclic aromatic ring system, for example, anthracenyl, benzyl, fluorenyl, indenyl, naphthyl, phenanthrenyl, phenyl and the like.

The term "aryl" is also intended to include the partially hydrogenated derivatives of such ring systems, e.g. 1,2,3,4-tetrahydronaphthyl.

The term "aryloxy" denotes an aryl radical bonded to an oxygen atom that is attached to a core structure, such as benzyloxy.

The term "cycloalkyl" denotes a saturated monocyclic or bicyclic cycloalkyl group. Examples of cycloalkyl groups include cyclopropyl, cyclobutyl, cyclopentyl, cyclohexyl, cycloheptyl, cyclooctyl, and the like.

The term "halogen" or "halo" represents chlorine, bromine, fluorine and iodine atoms and radicals.

The term "haloalkyl" refers to an alkyl or cycloalkyl substituent wherein at least one hydrogen radical is replaced with a halogen radical. Where more than one hydrogen is replaced with halogen, the halogens may be the same or different. Examples of haloalkyl radicals include trifluoromethyl, 2,2,2-trifluoroethyl, 4,4,4-trifluorobutyl, 4,4-difluorocyclohexyl, chloromethyl, dichloromethyl, trichloromethyl, 1-bromoethyl, and the like.

The term "haloalkoxy" refers to an alkoxy radical in which at least one hydrogen radical is replaced with a halogen radical. Where more than one hydrogen is replaced with halogen, the halogens may be the same or different. Examples of haloalkoxy radicals include difluoromethoxy, trifluoromethoxy, 2,2,2-trifluoroethoxy, chloromethoxy, bromomethoxy, and the like.

The term "heteroaryl" as used herein includes heterocyclic unsaturated ring systems containing one or more heteroatoms such as nitrogen, oxygen, and sulfur. If the heteroaryl group contains more than one heteroatom, the heteroatoms may be the same or different. The heteroaryl radicals may be bonded via a carbon atom or a heteroatom. The term "heteroaryl" is also intended to include the partially hydrogenated derivatives of such ring systems. Examples of heteroaryl groups include furanyl (also known as "furyl"), imidazolinyl, imidazolyl (also known as "1,3-diazolyl"), indolyl, oxadiazolyl, oxazinyl, oxazolyl, isoxazolyl, pyranyl, pyrazinyl (also known as "1,4-diazinyl"), pyrazolyl (also known as "1,2-diazolyl"), pyrazolinyl, pyrazyl, pyridazinyl (also known as "1,2-diazinyl"), pyridyl (also known as pyridinyl), pyrimidinyl (also known as "1,3 diazinyl" and "pyrimidyl"), pyrrolyl, thiadiazinyl, thiadiazolyl, thiatriazolyl, thiazolyl, isothiazolyl, thienyl, thiofuranyl (also known as "thiophenyl"), thiopyranyl, triazinyl, triazolyl, and the like.

The term "heteroaryl" also embraces radicals in which 2 or 3 rings are fused together, wherein at least on such ring contains a heteroatom as a ring atom, including radicals wherein (a) a heterocycloalkyl ring is fused with an aryl or heteroaryl ring, or (b) a cycloalkyl ring is fused with a heteroaryl ring. Examples of 2-fused ring heteroaryls include benzodioxinyl, dihydrobenzodioxinyl, benzofuranyl, dihydrobenzofuranyl, isobenzofuranyl, benzimidazolyl, benzothiadiazolyl, tetrahydrobenzothiadiazolyl, benzothiazolyl, benzothienyl (also known as "benzothiophenyl," "thionaphthenyl," and "benzothiofuranyl"), benzoxazinyl, dihydrobenzoxazinyl, benzoxazolyl, chromanyl, isochromanyl, chromenyl, cinnolinyl (also known as "1,2-benzodiazinyl"), imidazopyridinyl (e.g. imidazo[1,2-a]pyridinyl or imidazo[4,5-c]pyridinyl), indazolyl, indolinyl, isoindolinyl, indolizinyl, indolyl, isoindolyl, naphthyridinyl, oxathiolopyrrolyl, pteridinyl, pthalazinyl, purinyl (also known as "imidazo[4,5-d]pyrimidinyl"), pyranopyrrolyl, pyrazoloazepinyl, tetrahydropyrazoloazepinyl (e.g. tetrahydropyrazolo[1,5-a]azepinyl), pyrazolopyridinyl, tetrahydropyrazolopyridinyl (e.g. tetrahydropyrazolo[1,5-a]pyridinyl), pyrazolopyrimidinyl (e.g. pyrazolo[3,4-d]pyrimidinyl), pyridopyrazinyl (e.g. pyrido[2,3-b]pyrazinyl), pyridopyridinyl, pyrrolopyrazolyl, dihydropyrrolopyrazolyl (e.g. dihydropyrrolo[1,2-b]pyrazolyl), quinazolinyl (also known as "1,3-benzodiazinyl"), quinolinyl (also known as "1-benzazinyl"), isoquinolinyl (also known as "2-benzazinyl"), quinolizinyl, quinolyl, isoquinolyl, quinoxalinyl, dithianaphthalenyl, thienofuranyl (e.g. thieno[3,2-b]furanyl), and the like.

Examples of 3-fused ring heteroaryls include acridinyl, diazaanthryl, triazaphenanthrene, carbazolyl, carbolinyl, furocinnolinyl, perimidinyl, phenanthridinyl, phenanthrolinyl, phenazinyl, phenothiazinyl, phenoxathiinyl, phenoxazinyl, thianthrenyl, xanthenyl, and the like.

The term "heterocycloalkyl" denotes a saturated monocyclic or polycyclic cycloalkyl group, in which at least one of the carbon atoms is replaced with a heteroatom such as nitrogen, oxygen or sulfur. If the heterocycle contains more than one heteroatom, the heteroatoms may be the same or different. The heterocycloalkyl radicals may be bonded via a carbon atom or a heteroatom. Examples of heterocycloalkyl groups include azetidinyl, dioxacyclohexyl, 1,3-dioxolanyl, imidazolidinyl, morpholinyl, piperazinyl, piperidinyl, pyrazolidinyl, pyrrolidinyl, tetrahydrofuranyl, tetrahydropyranyl, tetrahydrothiopyranyl, thiazanyl, and the like.

A cyclic group may be bonded to another group in more than one way. If no particular bonding arrangement is specified, then all possible arrangements are intended. For example, the term "pyridyl" includes 2-, 3- or 4-pyridyl (2-, 3-, or 4-pyridinyl).

The term "mammal" means animals including, for example, dogs, cats, cows, sheep, goats, horses and humans. Preferred mammals include humans.

The term "oxo" means a carbonyl group formed by the combination of a carbon atom and an oxygen atom.

The term "patient" includes both human and non-human patients.

The phrase "pharmaceutically acceptable" indicates that the designated carrier, vehicle, diluent, and/or salt is generally chemically and/or physically compatible with the other ingredients comprising the formulation, and physiologically compatible with the recipient thereof.

The term "salts" refers to both organic and inorganic salts of a compound of Formula (I). Such salts can be prepared in situ during the final isolation and purification of a compound, or by separately reacting a compound, prodrug or stereoisomer of Formula (I) with a suitable organic or inorganic acid or base and isolating the salt thus formed. Representative anionic salts include hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts and the like. Representative cationic salts include sodium, potassium, calcium, and magnesium salts and the like. See generally, e.g., Berge, et al., *J. Pharm. Sci.*, 66, 1-19 (1977).

A salt of a compound of Formula (I) may be readily prepared by mixing together solutions of a compound of Formula (I) and the desired acid or base, as appropriate. The salt may precipitate from solution and be collected by filtration or may be recovered by evaporation of the solvent.

The term "radical" denotes a group of atoms that behaves as a single reactant in a chemical reaction, e. g., an organic radical is a group of atoms that imparts characteristic properties to a compound containing it, or which remains unchanged during a series of reactions or transformations.

The symbol "—" represents a covalent bond.

The phrase "reaction-inert solvent" or "inert solvent" refers to a solvent, or mixture of solvents, that does not interact with starting materials, reagents, intermediates or products in a manner that adversely affects their desired properties.

The terms "treat," "treating," "treated" or "treatment" as used herein includes preventative (e.g., prophylactic), palliative or curative uses or results.

The compounds of Formula (I) may contain asymmetric or chiral centers and, therefore, exist in different stereoisomeric forms. Those skilled in the art will appreciate that, unless otherwise specified, all stereoisomers (e.g., enantiomers and diastereoisomers, and racemic mixtures thereof) of the novel compounds and intermediates described, illustrated and/or discussed herein are within the scope of the claimed invention. In addition, unless otherwise specified, the present invention embraces all geometric and positional isomers. The (3S,4S) enantiomer of the core pyrrolidinyl configuration is preferred.

Diasteriomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diastereomers and converting (e.g., hydrolyzing) the individual diastereomers to the corresponding pure enantiomers. Additional methods include resolution of racemic mixtures using chiral salts, as well as chiral chromatography.

Those skilled in the art will further recognize that the compounds of Formula (I) can exist in crystalline form as hydrates wherein molecules of water are incorporated within the crystal structure thereof and as solvates wherein molecules of a solvent are incorporated therein. All such hydrate and solvate forms are considered part of this invention.

Practitioners will appreciate that certain compounds of Formula (I) may exist as tautomeric isomers, i.e., that equilibrium exists between two isomers which are in rapid equilibrium with each other. A common example of tautomerism is keto-enol tautomerism, i.e.,

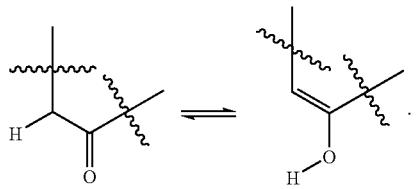

The degree to which one tautomer is present over the other depends upon various factors, including substitution pattern and solvent type. Other examples in accordance with the present invention will be recognized by those skilled in the art. All tautomeric forms of Formula (I) are included within the scope of the invention unless otherwise specified.

The present invention also includes prodrugs of the compounds of the invention. The term "prodrug" refers to a drug precursor which, following administration, releases the drug in vivo via a chemical or physiological process (e.g., upon being brought to physiological pH or through enzymatic activity). The prodrug may itself be biologically active, or may be converted to a biologically active compound (e.g. by metabolism or hydrolysis) during its residence time in the body. A discussion of the preparation and use of prodrugs is provided by Higuchi & Stella, "Prodrugs as Novel Delivery Systems", Vol. 14 of the A.C.S. Symposium Series, and in "Bioreversible Carriers in Drug Design," ed. Edward B. Roche, American Pharmaceutical Association and Pergamon Press, 1987. All prodrugs of the various compounds of Formula (I) are within the scope of the present invention.

The present invention also embraces isotopically-labeled compounds of Formula (I) that are identical to those recited herein, but for the fact that one or more atoms are replaced by an atom having an atomic mass or mass number different from the atomic mass or mass number usually found in nature. Examples of isotopes that can be incorporated into compounds of Formula (I) include isotopes of hydrogen, carbon, nitrogen, oxygen, phosphorus, fluorine, and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. The compounds of Formula (I), and pharmaceutically acceptable salts thereof, that contain the aforementioned isotopes and/or other isotopes of the other atoms are within the scope of the instant invention.

Certain isotopically-labeled compounds of Formula (I), for example those into which radioactive isotopes such as $^3H$ and $^{14}C$ are incorporated, are useful in drug and/or substrate tissue distribution assays. Tritiated, i.e., $^3H$ and $^{14}C$, isotopes are particularly preferred for their ease of preparation and detectability. Furthermore, substitution with heavier isotopes such as deuterium, i.e., $^2H$, may afford certain therapeutic advantages resulting from greater metabolic stability, for example, increased in vivo half-life, or reduced dosage requirements and, hence, may be preferred in some circumstances. Isotopically-labeled compounds of Formula (I), and pharmaceutically acceptable salts thereof, can be generally prepared by carrying out analogous procedures to those disclosed in the Schemes and/or in the Examples below, by substituting a readily available isotopically-labeled reagent for a non-isotopically labeled reagent.

The invention also includes pharmaceutical compositions comprising an amount of a compound of Formula (I), or a pharmaceutically acceptable salt of the compound, and optionally a pharmaceutically acceptable vehicle, carrier or diluent. In a preferred embodiment, the pharmaceutical composition is of an amount effective at inhibiting the enzyme PDE9 in a mammal. In another preferred embodiment, the mammal is a human.

The present invention includes the use of a combination of a PDE9 inhibitor compound as provided in Formula (I) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula (I) or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula (I), depending on the disease, disorder, or condition to be treated. Pharmaceutically active agents that may be used in combination with the compositions of the present invention include, without limitation:

(i) acetylcholinesterase inhibitors, such as donepezil hydrochloride (E2020, ARICEPT, MEMAC), physostigmine salicylate (ANTILIRIUM), physostigmine sulfate (ESERINE), metrifonate, neostigmine, pyridostigmine (MESTI- NON), ambenonium (MYTELASE), demarcarium, Debio992 (also known as ZT-1), rivastigmine (EXELON), ladostigil (also known as TV3326), NP-0361, galantamine hydrobromide (RAZADYNE, RIMINYL, NIVALIN), tacrine (COGNEX), velnacrine maleate, memoquin, huperzine A (HUP-A), phenserine, and edrophonium (ENLON, TENSILON);

(ii) amyloid-β (or fragments thereof), such as $A\beta_{1-15}$ conjugated to pan HLA DR-binding epitope (PADRE), ACC-001, ACI-01, ACI-24, AN-1792, Affitope AD-01, CAD106, and V-950;

(iii) antibodies to amyloid-β (or fragments thereof), such as bapineuzumab (also known as AAB-001), AAB-002, ACI-01-Ab7, BAN-2401, intravenous Ig (GAMMAGARD), LY2062430 (humanized m266), PF-04360365 (also known as RN-1219), RN-6G, R-1450, ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid accumulation and fibrillization) such as bisnorcymserine (also known as BNC), pioglitazone, PBT2, flurbiprofen (ANSAID, FROBEN) and its R-enantiomer tarenflurbil (also known as MPC-7869; FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), insulin-degrading enzyme (also known as insulysin), the gingko biloba extract EGb-761 (ROKAN, TEBONIN), tramiprosate (NC-758, CEREBRIL, ALZHEMED), eprodisate (NC-503, FIBRILLEX, KIACTA), compound W (3,5-bis(4-nitrophenoxy)benzoic acid), NGX-96992, neprilysin (also known as neutral endopeptidase (NEP)), scyllo-inositol (also known as scyllitol, ELND005, AZD-103), atorvastatin (LIPITOR), simvastatin (ZOCOR), KLVFF-(EEX)3, and RAGE (receptor for advanced glycation end-products) inhibitors;

(v) alpha-adrenergic receptor agonists, such as clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitniptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, NON), tolterodine (DETROL), oxybutynin (DITROPAN, LYRINEL XL, OXYTROL), penthienate bromide, propantheline (PROBANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, and primidone (MYSOLINE);

(ix) antipsychotics, such as lurasidone (also known as SM-13496), aripiprazole (ABILIFY), chlorpromazine (THORAZINE), haloperidol (HALDOL), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine, loxapine (LOXITANE), mesoridazine, molindone (MOBAN), perphenazine, thioridazine, thiothixine, trifluoperazine (STELAZINE), clozapine (CLOZARIL), norclozapine (ACP-104), risperidone (RISPERDAL), paliperidone (INVEGA), melperone, olanzapine (ZYPREXA), quetiapine (SEROQUEL), sertindole, sulpiride (MERESA, DOGMATYL, SULPITIL), amisulpride, ziprasidone (GEODON), blonanserin (LONASEN), and bifeprunox;

(x) calcium channel blockers such as nilvadipine (ESCOR, NIVADIL), amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), diltiazem (CARDIZEM), verapamil (CALAN, VERELAN), and enecadin (also known as NS-7);

(xi) catechol O-methyltransferase (COMT) inhibitors, such as tolcapone (TASMAR), entacapone (COMTAN), and tropolone;

(xii) central nervous system stimulants, such as caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g. ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPOMEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocriptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), and rotigotine (NEUPRO);

(xv) dopamine receptor antagonists, such as tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SCH-23390, ecopipam, SKF-83566, and metoclopramide (REGLAN);

(xvi) dopamine reuptake inhibitors such as nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), pentobarbital (NEMBUTAL), progabide (GABRENE), and clomethiazole;

(xviii) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody), rituximab (RITUXAN), alemtuzumab (CAMPATH), daclizumab (ZENAPAX), and natalizumab TSABRI);

(xix) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-benzyloxy-5-((5-undecyl-2H-pyrrol-2-ylidene)methyl)-2,2'-bi-1H-pyrrole (also known as PNU-156804);

(xx) interferons, including interferon beta-1a (AVONEX, REBIF) and interferon beta-1b (BETASERON, BETAFERON);

(xxi) levodopa (or its methyl or ethyl ester), alone or in combination with a DOPA decarboxylase inhibitor (e.g. carbidopa (SINEMET, CARBILEV, PARCOPA, V1512), benserazide (MADOPAR), α-methyldopa, monofluromethyldopa, difluoromethyldopa, brocresine, or m-hydroxybenzylhydrazine);

(xxii) N-methyl-D-aspartate (NMDA) receptor antagonists, such as memantine (NAMENDA, AXURA, EBIXA), amantadine (SYMMETREL), acamprosate (CAMPRAL), besonprodil (also known as PD-196,860 or CI-1041), ketamine (KETALAR), delucemine (also known as NPS 1506), dexanabinol (also known as HU-211), dextromethorphan, dextrorphan, traxoprodil (also known as CP-101,606), himantane, idantadol (also known as V-3381), lancicemine (also known as AR-R 15896), levorphanol (DROMORAN), methadone, (DOLOPHINE), neramexane (also known as MRZ 2/579), perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xxiii) monoamine oxidase (MAO) inhibitors, such as selegiline (EMSAM), selegiline hydrochloride (I-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide (also known as PNU-151774E), isocarboxazid (MARPLAN), nialamide (NIAMID), rasageline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxiv) muscarinic receptor (particularly M1 subtype) agonists, such as bethanechol chloride (DUVOID, URECHOLINE), pilocarpine (SALAGEN), NGX267, arecoline, L-687306, L-689660, furtrethonium iodide (FURAMON, FURANOL), furtrethonium benzensulfonate, furtrethonium p-toluenesulfonate, McN-A-343, oxotremorine, and carbachol (CARBASTAT, MIOSTAT, CARBOPTIC);

(xxv) nicotinic receptor agonists, such as epibatidine, ABT-089, ABT-594, AZD-0328, R4996 (also known as MEM-63908), TC-5619, and EVP-6124;

(xxvi) neuroprotective drugs such as 2,3,4,9-tetrahydro-1H-carbazol-3-one oxime, AL-108, ACD3480 (also known as TC-1734), bis(4-β-D-glucopyranosyloxybenzyl)-2-β-D-glucopyranosyl-2-isobutyltartrate (also known as dactylorhin B or DHB), xaliproden (XAPRILA), dimeboline hydrochloride (DIMEBON), disufenton (NXY-059, CEROVIVE), arundic acid (ONO-2506, PROGLIA, CEREACT), citicoline (also known as cytidine 5'-diphosphocholine), edaravone (RADICUT), AEOL-10150, AGY-94806 (also known as SA-450 and Msc-1), granulocyte-colony simulating factor (AX-200), BAY-387271 (also known as KN-387271), DP-b99, HF-0220 (17-β-hydroxyepiandrosterone), HF-0420 (also known as oligotropin), pyridoxal 5'-phosphate (also known as MC-1), microplasmin, S-18986, piclozotan (also known as SUN-N4057), NP031112, L-seryl-L-methionyl-L-alanyl-L-lysyl-L-glutamyl-glycyl-L-valine, and SUN-N8075;

(xxvii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxviii) other PDE9 inhibitors, such as BAY 73-6691 and those disclosed in US Patent Publication Nos US2003/0195205, US2004/0220186, US2006/0111372, and US2006/0106035;

(xxix) other phosphodiesterase (PDE) inhibitors, including (a) PDE1 inhibitors (e.g. vinpocetine (CAVINTON, CERACTIN, INTELECTOL) and those disclosed in U.S. Pat. No. 6,235,742), (b) PDE2 inhibitors (e.g. erythro-9-(2-hydroxy-3-nonyl)adenine (EHNA), BAY 60-7550, and those described in U.S. Pat. No. 6,174,884), (c) PDE4 inhibitors (e.g. rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (d) PDE5 inhibitors (e.g. sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, PF489791, UK-357903, DA-8159, and those disclosed in International Patent Applications WO05/049616, WO06/120552, and WO07/122466);

(xxx) quinolines, such as quinine (including its hydrochloride, dihydrochloride, sulfate, bisulfate and gluconate salts), chloroquine, hydroxychloroquine (PLAQUENIL), mefloquine (LARIAM), and amodiaquine (CAMOQUIN, FLAVOQUINE);

(xxxi) β-secretase inhibitors, such as WY-25105, (+)-phenserine tartrate (POSIPHEN), LSN-2434074 (also known as LY-2434074), PNU-33312, KMI-574, SCH-745966, AcrER (N²-acetyl-D-arginyl-L-arginine), loxistatin (also known as E64d), and CA074Me;

(xxxii) γ-secretase inhibitors, such as LY-411,575, LY-685,458, ELAN-G, ELAN-Z, 4-chloro-N-[2-ethyl-1(S)-(hydroxymethyl)butyl]benzenesulfon-amide;

(xxxiii) serotonin (5-hydroxytryptamine) 1A (5-HT$_{1A}$) receptor antagonists, such as spiperone, levo-pindolol, BMY 7378, NAD-299, S(−)-UH-301, NAN 190, WAY 100635, lecozotan (also known as SRA-333);

(xxxiv) serotonin (5-hydroxytryptamine) 6 (5-HT$_6$) receptor antagonists, such as mianserin (TORVOL, BOLVIDON, NORVAL), methiothepin (also known as metitepine), ritanserin, ALX-1161, ALX-1175, MS-245, LY-483518 (also known as SGS518), MS-245, Ro 04-6790, RO 43-68544, Ro 63-0563, RO 65-7199, Ro 65-7674, SB-399885, SB-214111, SB-258510, SB-271046, SB-357134, SB-699929, SB-271046, SB-742457 and PRX-07034;

(xxxv) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, and tesofensine;

(xxxvi) trophic factors, such as nerve growth factor (NGF), basic fibroblast growth factor (bFGF), neurotrophin-3 (NT-3), brain-derived neurotrophic factor (BDNF), and glial-derived neurotrophic factor (GDNF), and agents that stimulate local production of trophic factors, such as propentofylline, idebenone, and AIT-082 (NEOTROFIN); and the like.

The invention also includes methods of inhibiting PDE9 in a mammal comprising administering to the mammal in need of such inhibition a PDE9 inhibiting amount of: (a) a compound of Formula (I), or a pharmaceutically acceptable salt thereof; or (b) a pharmaceutical composition comprising a compound of Formula (I), or a pharmaceutically acceptable salt thereof, in a pharmaceutically acceptable vehicle, carrier or diluent; either alone or in combination with a second agent as described above.

The invention also includes methods of treating conditions mediated by PDE9 inhibition in a mammal comprising administering to the mammal in need of such treatment a therapeutically effective amount of: (a) a compound of Formula (I), or a pharmaceutically acceptable salt thereof; or (b) a pharmaceutical composition comprising a compound of Formula (I), or a pharmaceutically acceptable salt thereof, in a pharmaceutically acceptable vehicle, carrier or diluent; either alone or in combination with a second agent described above.

Conditions that may be treated, controlled or prevented by the methods of the present invention include diseases and disorders associated with neurodegeneration such as: Alexander disease, Alper's disease, Alzheimer's disease, amyotrophic lateral sclerosis (ALS; also known as Lou Gehrig's disease or motor neuron disease), ataxia-telangiectasia, Batten disease (also known as Spielmeyer-Vogt-Sjogren-Batten disease), Binswanger's dementia (subcortical arteriosclerotic encephalopathy), bipolar disorders, bovine spongiform encephalopathy (BSE), Canavan disease, chemotherapy-induced dementia, Cockayne syndrome, corticobasal degeneration, Creutzfeldt-Jakob disease, depression, Down syndrome, frontotemporal lobar degeneration (including frontotemporal dementia, semantic dementia, and progressive nonfluent aphasia), Gerstmann-Sträussler-Scheinker disease, glaucoma, Huntington's disease (chorea), HIV-associated dementia, hyperkinesias, Kennedy's disease, Korsakoff's syndrome (amnesic-confabulatory syndrome), Krabbe's disease, Lewy body dementia, logopenic progressive aphasia, Machado-Joseph disease (spinocerebellar ataxia type 3), multiple sclerosis, multiple system atrophy (olivopontocerebellar atrophy), myasthenia gravis, Parkinson's disease, Pelizaeus-Merzbacher disease, Pick's disease, pre-senile dementia (mild cognitive impairment), primary lateral sclerosis, primary progressive aphasia, radiation-induced dementia, Refsum's disease (phytanic acid storage disease), Sandhoff disease, Schilder's disease, schizophrenia, semantic dementia, senile dementia, Shy-Drager syndrome, spinocerebellar ataxias, spinal muscular atrophies, Steele-Richardson-Olszewski disease (progressive supranuclear palsy), tabes dorsalis, tardive dyskinesia, vascular amyloidosis, and vascular dementia (multi-infarct dementia).

Preferably the neurodegenerative disease or disorder is Alzheimer's disease.

Other conditions and disorders associated with PDE9 that may be treated or controlled by the methods of the present invention include disorders of the urogenital system such as sexual dysfunction, attention deficit disorder (ADD), attention deficit hyperactivity disorder (ADHD), diabetes, cardiovascular disorders or diseases such as systemic hypertension, pulmonary hypertension, congestive heart failure, coronary artery disease, atherosclerosis, stroke, thrombosis, conditions of reduced blood vessel patency (e.g. post-percutaneous transluminal coronary angioplasty), peripheral vascular disease, renal disease, angina (including stable, unstable, and variant (Prinzmetal) angina), and any condition where improved blood flow leads to improved end organ function.

The present invention also relates to methods for promoting neurorestoration and functional recovery in patients suffering from traumatic or non-traumatic injury to the brain, spinal cord or peripheral nerves. Traumatic brain injuries include both closed head injuries (in which the skull is not broken) and open, or penetrating, head injuries (in which an object pierces the skull and breaches the dura mater), wherein sudden trauma (e.g., accidents, falls, assaults) causes damage to the brain tissue by tearing, stretching, bruising, or swelling. Causes of non-traumatic brain injuries include aneurism, stroke, meningitis, oxygen deprivation due to anoxia, hypoxia, or ischemia, brain tumor, infection (e.g. encephalitis), poisoning, substance abuse, and the like. The present invention is useful for the treatment of cognitive impairment and cognitive dysfunction resulting from brain injuries as well as from neurodegenerative diseases and disorders.

The present invention also relates to methods for preventing the above-described conditions in a mammal, including human, comprising the steps of administering to the mammal an amount of: (a) a compound of Formula (I), or a pharmaceutically acceptable salt thereof; or (b) a pharmaceutical composition comprising a compound of Formula (I), or a pharmaceutically acceptable salt thereof, in a pharmaceutically acceptable vehicle, carrier or diluent; either alone or in combination with a second agent as described above, as part of an appropriate dosage regimen designed to prevent said condition.

The present invention also relates to methods for improving cognitive deficits, including deficits in perception, concentration, learning, memory, communication, reasoning, and problem-solving.

The appropriate dosage regimen, the amount of each dose administered and the intervals between doses of the compound will depend, among others, upon the compound of Formula (I) of this invention being used, the type of pharmaceutical compositions being used, the characteristics of the subject being treated and the type and severity of the conditions to be treated. In general, an effective dose for compounds of Formula (I) or pharmaceutically acceptable salts thereof, is in the range of from about 0.1 mg to about 3,500 mg per day. For a normal adult human having a body mass of about 70 kg, a dosage in the range of from about 0.01 mg to about 50 mg per kg body mass is typically sufficient, and preferably from about 0.2 to 2.5 mg per kg, in single or divided doses daily. Administration may be in single (e.g., once daily) or multiple doses or via constant infusion.

Some variability in the general dosage range may be required depending upon the age and mass of the subject being treated, the intended route of administration, the particular compound being administered, and the like. The determination of dosage ranges and optimal dosages for a particular mammalian subject is within the ability of a skilled person having benefit of the instant disclosure.

The compounds of Formula (I) may be administered by a variety of conventional routes of administration, including oral, buccal, sublingual, ocular, topical (e.g., transdermal), parenteral (e.g., intravenous, intramuscular, or subcutaneous), rectal, intracisternal, intravaginal, intraperitoneal, intravesical, local (e.g., powder, ointment, or drop), nasal and/or inhalation dosage forms or using a "flash" formulation, i.e., allowing the medication to dissolve in the mouth without the need to use water. As will be recognized by one of skill in the art, the appropriate dosage regimen, the amount of each dose administered and the intervals between doses of the compound will depend upon the compound of Formula (I), or the prodrug thereof, being used, the type of pharmaceutical compositions being used, the characteristics of the subject being treated, and/or the severity of the conditions being treated.

Methods of preparing various pharmaceutical compositions with amounts of active ingredients are known, or will be apparent in light of this disclosure, to those skilled in this art. See, for example, Remington's Pharmaceutical Sciences, Mack Publishing Co., Easton, Pa., 19th Ed. (1995).

Suitable pharmaceutical carriers, vehicles and diluents for such compositions include inert solid diluents or fillers, sterile aqueous solutions and various organic solvents. The pharmaceutical compositions formed by combining a compound of this invention and pharmaceutically acceptable carriers, vehicles or diluents are readily administered in a variety of dosage forms such as tablets, powders, lozenges, syrups, injectable solutions and the like.

Solid dosage forms for oral administration include capsules, tablets, powders, and granules. In such solid dosage forms, the active compound is admixed with at least one inert conventional pharmaceutical excipient (or carrier) such as sodium citrate, calcium carbonate, or dicalcium phosphate, or (a) fillers or extenders, such as for example, starches, lactose, sucrose, mannitol and silicic acid; (b) binders, such as for example, carboxymethylcellulose, alginates, gelatin, polyvinylpyrrolidone, sucrose and acacia; (c) humectants, such as for example, glycerol; (d) disintegrating agents, such as for example, agar-agar, calcium carbonate, potato or tapioca starch, alginic acid, certain complex silicates, and sodium carbonate; (e) solution retarders, such as for example, paraffin; (f) absorption accelerators, such as for example, quaternary ammonium compounds; (g) wetting agents, such as for example, cetyl alcohol and glycerol monostearate; (h) adsorbents, such as for example, kaolin and bentonite; and/or (i) lubricants, such as for example, talc, calcium stearate, magnesium stearate, solid polyethylene glycols, sodium lauryl sulfate or mixtures thereof. In the case of capsules and tablets, the dosage forms may further comprise buffering agents.

Solid dosage forms may be formulated as modified release and pulsatile release dosage forms containing excipients such as those detailed above for immediate release dosage forms together with additional excipients that act as release rate modifiers, these being coated on and/or included in the body of the device. Release rate modifiers include, but are not limited to, hydroxypropylmethyl cellulose, methyl cellulose, sodium carboxymethylcellulose, ethyl cellulose, cellulose acetate, polyethylene oxide, xanthan gum, ammoniomethacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients.

The pharmaceutical compositions of the invention may further comprise fast dispersing or dissolving dosage formulations (FDDFs). The terms dispersing or dissolving as used herein to describe FDDFs are dependent upon the solubility of the drug substance used i.e., where the drug substance is insoluble, a fast dispersing dosage form may be prepared, and where the drug substance is soluble, a fast dissolving dosage form may be prepared.

Solid compositions of a similar type may also be employed as fillers in soft or hard filled gelatin capsules using such excipients as lactose or milk sugar, as well as high molecular weight polyethylene glycols and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethanol, isopropanol, ethyl carbonate, benzyl benzoate, propylene glycol, 1,3-butylene glycol, oils (in particular, cottonseed oil, groundnut oil, corn germ oil, olive oil, castor oil, and sesame seed oil), glycerol, tetrahydrofurfuryl alcohol, polyethylene glycols and fatty acid esters of sorbitan, or mixtures of these substances, and the like.

In addition to the active compound(s), the pharmaceutical composition may further include suspending agents, such as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like. Sweeteners, flavoring, and perfuming agents may also be included.

The pharmaceutical compositions of the invention may further comprise adjuvants, such as preserving, wetting, emulsifying and dispersing agents. Prevention of microorganism contamination of the instant compositions can be accomplished with various antibacterial and antifungal agents, for example, parabens, chlorobutanol, phenol, sorbic acid and the like. It may also be desirable to include isotonic agents, for example, sugars, sodium chloride and the like.

Prolonged absorption of injectable pharmaceutical compositions may be affected by the use of agents capable of delaying absorption, for example, aluminum monostearate and gelatin.

For parenteral administration, solutions in sesame or peanut oil, aqueous propylene glycol, or in sterile aqueous solutions may be employed. Such aqueous solutions should be suitably buffered if necessary and the liquid diluent first rendered isotonic with sufficient saline or glucose. These aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of Formula (I) are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insulator may be formulated containing a powder mix of a compound or compounds of the invention and a suitable powder base such as lactose or starch.

Pharmaceutical compositions of the present invention may also be configured for treatments in veterinary use, where a compound of the present invention, or a veterinarily acceptable salt thereof, or veterinarily acceptable solvate or prodrug thereof, is administered as a suitably acceptable formulation in accordance with normal veterinary practice and the veterinary practitioner will determine the dosing regimen and route of administration which will be most appropriate for a particular animal.

In general, the compounds of Formula (I), and pharmaceutically acceptable salts thereof, may be prepared according to the exemplary routes disclosed in the Schemes and Examples below, as well as by other conventional preparative procedures known, or apparent in light of the instant disclosure, to one of ordinary skill in the art. These processes form further aspects of the invention.

Some of the starting compounds for the reactions described in the Schemes and Examples are prepared as illustrated herein. All other starting compounds may be obtained from general commercial sources, such as Sigma-Aldrich Corporation, St. Louis, Mo.

Unless indicated otherwise, the following experimental abbreviations have the indicated meanings:

| | |
|---|---|
| µL—microliter | m—multiplet |
| bd—broad doublet | MHz—megahertz |
| bm—broad multiplet | Min(s)—minute(s) |
| BOC—t-butoxycarbonyl | MeOH—methanol |
| bs—broad singlet | Mg—milligram |
| CDCl₃—deuterated chloroform | ml—milliliter |
| CD₃OD—deuterated methanol | mmol—millimoles |
| dd—doublet of doublets | MPLC—medium pressure liquid chromatography |
| DMF—dimethylformamide | MS—mass spectroscopy |
| DMSO—dimethyl sulfoxide | NMR—nuclear magnetic resonance |
| dt—doublet of triplets | ppm—parts per million |
| EtOAc—ethyl acetate | psi—pounds per square inch |
| EtOH—ethanol | s—singlet |
| h (e.g., 1 h, 2 h)—hour(s) | SPA—scintillation proximity assay |
| H (e.g., 1H, 2H)—hydrogen(s) | t—triplet |
| Hz—hertz | THF—tetrahydrofuran |
| IPA—isopropyl alcohol | Tris—tris(hydroxymethyl)aminomethane |
| J—spin-spin coupling constant | |
| LC—liquid chromatography | |

The methods disclosed in the instant Schemes and Examples are intended for purposes of exemplifying the instant invention only and are not to be construed as limitations thereon.

Scheme 1 exemplifies multiple ways to form aliphatic hydrazines that can utilized to prepare compounds in this patent. Ketones can be converted to the hydrazide imine and reduced with borane or sodium cyanoborohydride. Other reducing agents can also be utilized. The boc group can then be removed with acid to form the desired hydrazine intermediate. Alternatively aliphatic alcohols can be converted to boc-protected hydrazines by treatment with triphenyl phosphine and di-t-butyl diazacarboxylate. The boc groups can again be removed with acid to liberate the hydrazine. Aromatic hydrazine synthesis is well known in the literature by converting anilines to hydrazines through diazotization chemistry followed by reduction.

Scheme 1

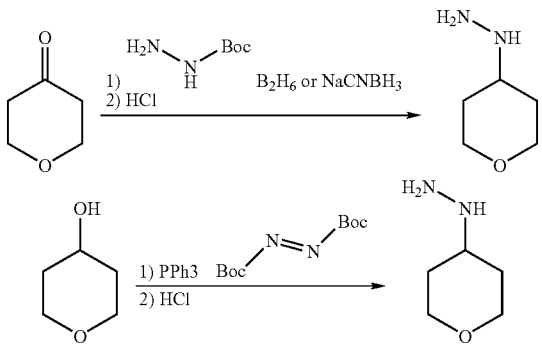

The pyrrolidine intermediates can be formed by coupling alpha-beta unsaturated esters with N-(methoxymethyl)(phenyl)-N-(trimethylsilyl)methyl)methanamine which is commercially available by catalysis with acid. This chemistry is exemplified in the experimental section below and also by numerous literature examples such as Hosomi et al., *Chem. Lett.* 13(7) 1117-1120, 1984. The pyrrolidines have also been synthesized in an enantiomeric pure fashion by either employing chiral auxiliaries on the ester (see Nichols et al., *Org. Lett.*, 8(7), 1495-1498, 2006) or by utilizing a chiral benzyl amine in the cycloaddition chemistry (see Haight et al., *Org. Proc. Res. Dev.*, 8(6), 897-902, 2004).

Scheme 2

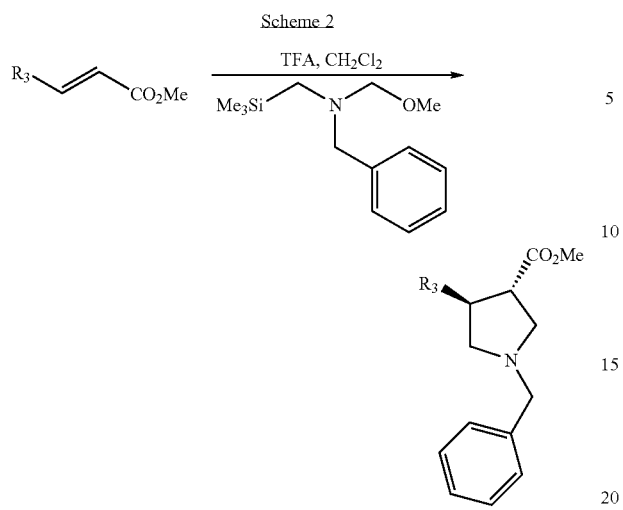

Hydrazines can then be coupled in the presence of a base such as sodium methoxide or triethylamine with 2-(ethoxymethylene)malononitrile or substituted variants to afford the desired amino cyano pyrazoles. The cyano group can be oxidized by a variety of reagent but two conditions have been utilized to prepare compounds for this patent. Concentrated sulfuric acid or hydrogen peroxide with ammonium hydroxide has afforded the amino-amide-pyrazoles. The amino-amide pyrazoles can then be coupled with esters in the presence of a base such as potassium t-butoxide with heated. The solvent of choice for this reaction has been tetrahydrofuran and in some cases dehydrating agents such as molecular sieves can be employed to improve upon the yields of the coupling.

Scheme 3

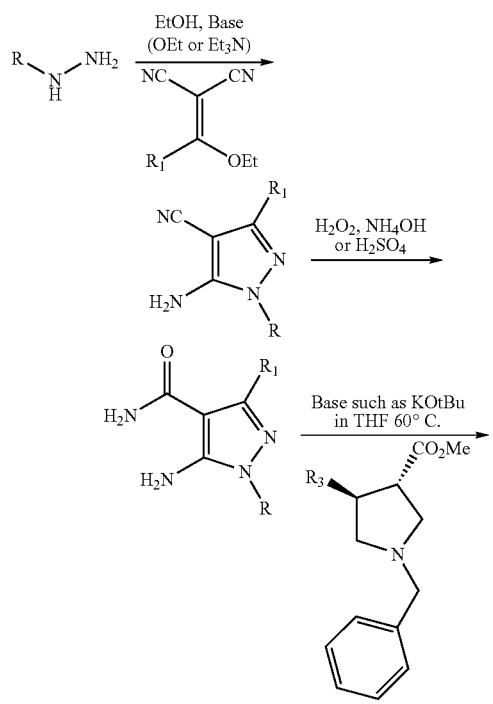

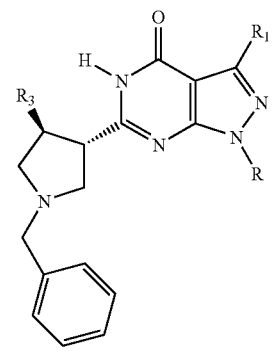

The benzyl group can then be removed via standard hydrogenation conditions to provide the secondary amine that is ready for further functionalization. The amine can be alkylated with alkyl halides in the presence of base or reductive amination chemistry utilizing a variety of hydride reducing agents can provide the desired compounds.

Scheme 4

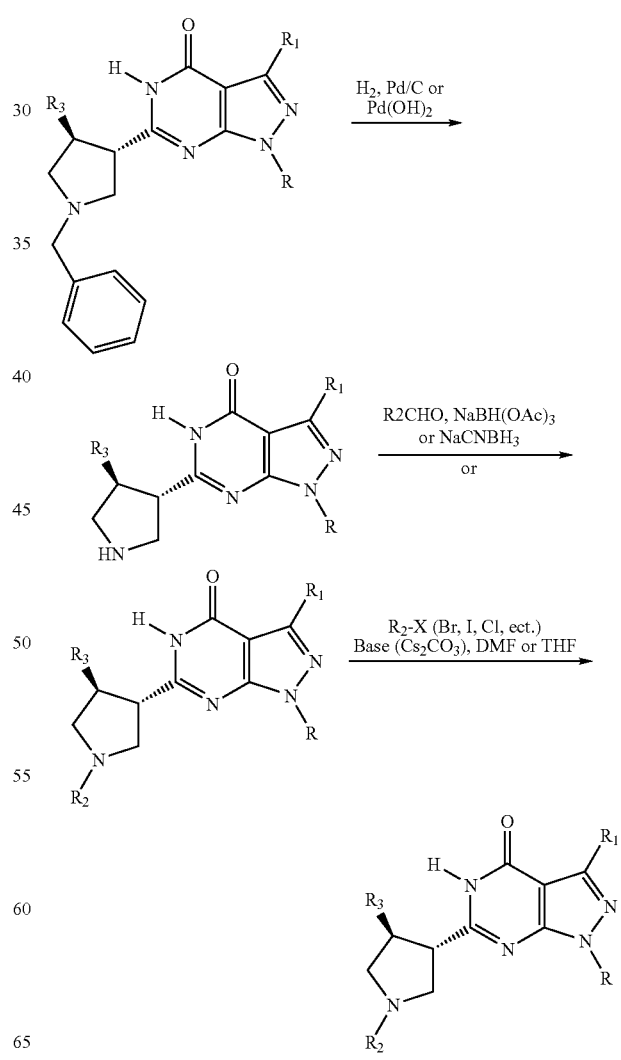

EXAMPLES

The Examples below are intended to illustrate particular embodiments of the invention and preparations thereto and are not intended to limit the specification, including the claims, in any manner. Unless otherwise noted, all reagents employed were obtained commercially.

Example 1

(a) 5-amino-1-(2-methoxyphenyl)-1H-pyrazole-4-carbonitrile

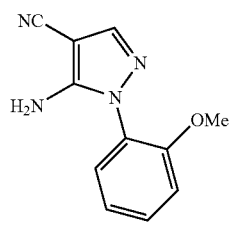

To a solution of 1-(2-methoxyphenyl)hydrazine hydrogen chloride (3 g, 0.017 mol) in ethanol (50 mL) was added 2-(methoxymethylene)malononitrile (1.89 g, 0.9 eq.) and sodium methoxide (1.92 g, 2.1 eq). The reaction mixture was heated at reflux for 18 h and concentrated. The reaction mixture was partitioned between brine and ethyl acetate. The organic layer was separated, dried with magnesium sulfate, filtered and concentrated. MPLC Biotage chromatography eluting with 20-60% ethyl acetate/hexanes afforded the title compound in 53% yield (1.9 g). 400 MHz $^1$H NMR (CDCl$_3$) δ 7.64 (m, 1 H), 7.40 (m, 2H), 7.08 (m,2H), 4.51 (bs, 2H), 3.87 (s, 3 H); MS: (M$^+$H m/z=215.2).

(b) 5-amino-1-(2-methoxyphenyl)-1H-pyrazole-4-carboxamide

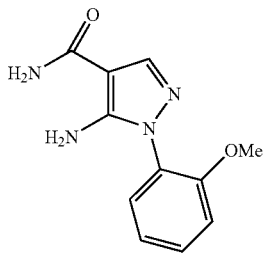

To a solution of 5-amino-1-(2-methoxyphenyl)-1H-pyrazole-4-carbonitrile (1.53 g) in saturated ammonium hydroxide (30 mL) was added 30% hydrogen peroxide solution (6 mL). The reaction stirred for 18 h at ambient temperature and was slowly quenched with 60 mL of a saturated sodium sulfate solution. The aqueous layer was extracted with ethyl acetate, dried with magnesium sulfate, filtered and concentrated. MPLC Biotage chromatography eluting with 2-6% methanol/methylene chloride provided the title compound 1.38 g (84%). 400 MHz $^1$H NMR (DMSO) δ 7.79 (s, 1 H), 7.42 (m, 1H), 7.25 (d, J=7.5 Hz, 2H), 7.19 (d, J=8.3 Hz, 2 H), 7.03 (t, J=6.2 Hz, 1H), 5.83 (s,2H), 3.76 (s, 3 H); MS: (M$^+$H m/z=233.2).

(c) (3,4-trans)-methyl 1-benzyl-4-methylpyrrolidine-3-carboxylate

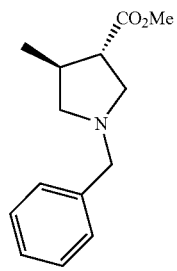

To a solution of (E)-methyl but-2-enoate (1.6 g) was added toluene (30 mL), N-(methoxymethyl)(phenyl)-N-((trimethylsilyl)methyl)methanamine (3.7 g) and trifluoroacetic acide (1.5 g). The reaction mixture was heated at 50° C. for 18 h. The reaction mixture was concentrated, quenched with saturated sodium bicarbonate, extracted with methylene chloride, dried with magnesium sulfate, filtered and concentrated. Purification via MPLC chromatography eluting with 20-30% ethyl acetate/hexanes provided the title compound (1.5 g). 400 MHz $^1$H NMR (CDCl$_3$) δ 7.33-7.20 (m, 5H), 4.15-4.08 (m, 1H), 3.66-3.53 (m, 2H), 2.87-2.74 (m, 2H), 2.53-2.44 (m, 2H), 2.23-2.19 (m, 1H), 1.23 (t, J=7.1 Hz, 3H), 1.11 (d, J=6.6 Hz, 3H).

(d) 6-[(3,4-trans)-1-benzyl-4-methylpyrrolidin-3-yl]-1-(2-methoxyphenyl)-1,5-dihydro-4H-pyrazolo[3,4-d]pyrimidin-4-one

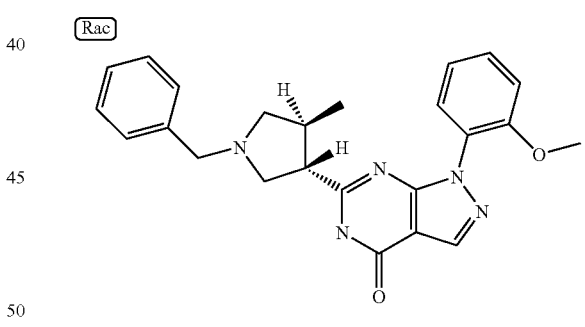

To (3,4-trans)-methyl 1-benzyl-4-methylpyrrolidine-3carboxylate (241 mg) and 5-amino-1-(2-methoxyphenyl)-1H-pyrazole-4-carboxamide (200 mg) was added a solution of potassium t-butoxide in (1M) in THF (4.31 mL, 5 eq.) The reaction mixture was heated at reflux for 16 h and poured into saturated sodium bicarbonate. The aqueous layer was extracted with ethyl acetate, dried with magnesium sulfate, filtered and concentrated. MPLC Biotage chromatography eluting with 1-4% methanol/methylene chloride with 0.5% saturated ammonium hydroxide provided 79 mg of the title compound. 400 MHz $^1$H NMR (DMSO) δ 8.16 (d, J=7.9 Hz, 1H), 7.92 (s, 1 H), 7.34 (m, 5H), 7.09 (m, 1H), 6.92 (m, 2H), 3.89 (s, 3H), 3.84 (m, 1H), 3.71 (m, 1H), 3.37 (t, J=9.1 Hz, 1H), 3.09 (m, 1H), 2.85 (m, 1H), 2.65 (m, 1H), 2.47 (m, 1H), 2.03 (m, 2H), 1.19 (d, J=7.1 Hz, 3H); MS: (M$^+$H m/z=416.1).

Example 2

6-[(3,4-trans)-1-benzyl-4-methylpyrrolidin-3-yl]-1-cyclopentyl-1,5-dihydro-4H-pyrazolo[3,4-d]pyrimidin-4-one

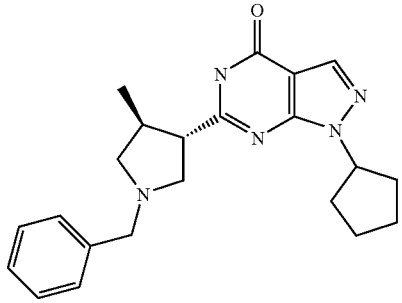

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide provided the title compound. 400 MHz $^1$H NMR (CD$_3$OD) δ 8.00 (s, 1H), 7.38-7.23 (m, 5H), 5.14-5.10 (m, 1H), 3.80-3.57 (m, 2H), 3.34 (t, J=8.3 Hz, 1H), 2.97 (d, J=9.9 Hz, 1H), 2.80-2.78 (m, 1H), 2.53-2.49 (m, 1H), 2.41-2.38 (m, 1H), 2.10-1.89 (m, 7H), 1.70-1.66 (m, 2H), 1.17 (d, J=6.6 Hz, 3H). MS: (M$^+$H m/z=378.1).

Example 3

6-[(3S,4S)-1-benzyl-4-methylpyrrolidin-3-yl]-1-cyclopentyl-1,5-dihydro-4H-pyrazolo[3,4-d]pyrimidin-4-one

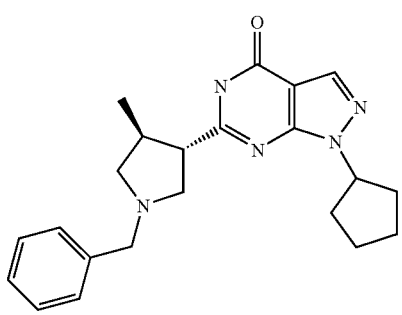

The racemate was separated on Chiralcel OD chiral HPLC column, Mobile Phase 90/10 Heptane/EtOH, T$_R$=6.807, to provide the enantiomer. 400 MHz $^1$H NMR (CDCl$_3$) δ 8.00 (s, 1H), 7.38-7.22 (m, 5H), 5.27-5.10 (m, 1H), 3.78 (d, J=12.5 Hz, 1H), 3.6 (d, J=12.5 Hz, 1H), 3.34 (t, J=8.3 Hz, 1H), 2.97 (d, J=9.9 Hz, 1H), 2.80-2.78 (m, 1H), 2.52-2.48 (m, 1H), 2.41-2.38 (m, 1H), 2.10-1.89 (m, 7H), 1.70-1.66 (m, 2H), 1.18(d, J=6.6 Hz, 3H). MS: (M$^+$H m/z=378.1).

Chiralcel OD, Mobile Phase 90/10 Heptane/IPA, T$_R$=9.433.

Example 4

(a) 1-cyclopentyl-6-[(3,4-trans-4-methylpyrrolidin-3-yl]-1H-pyrazolo[3,4-d]pyrimidin-4(5H)-one

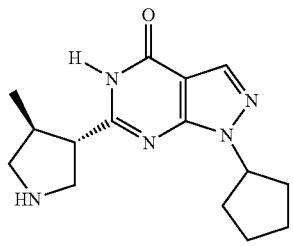

A solution of 6-[(3,4-trans)-1-benzyl-4-methylpyrrolidin-3-yl]-1-cyclopentyl-1,5-dihydro-4H-pyrazolo[3,4-d]pyrimidin-4-one (970 mg) in ethanol 25 mL was added to a Parr bottle. Acetic acid (2.5 mL) and Pd(OH)2 (500 mg) was added. The reaction mixture was placed on a hydrogenator under 40 PSI for 16 h. The reaction mixture was filtered through Celite and concentrated. The reaction mixture was partitioned between saturated bicarbonate solution and methylene chloride. The layers were separated and the aqueous layer was extracted 6× with methylene chloride. The organic layer was dried with magnesium sulfate, filtered and concentrated to provide 429 mg of the title compound. 400 MHz $^1$H NMR (CD$_3$OD) δ 9.25 (brs, 1H), 8.02 (s, 1H), 5.20-5.17 (m, 1H), 3.91 (m, 1H), 3.77-3.68 (m, 2H), 3.46-3.44 (m, 1H), 3.10 (m, 1H), 2.89 (m, 1H), 2.13-1.87 (m, 6H), 1.74-1.65 (m, 2H), 1.20 (d, J=6.2 Hz, 3H). MS: (M$^+$H m/z=288.1).

(b) 1-cyclopentyl-6-{(3,4-trans)-4-methyl-1-[4-(trifluoromethyl)pyrimidin-2-yl]pyrrolidin-3-yl}-1,5-dihydro-4H-pyrazolo[3,4-d]pyrimidin-4-one

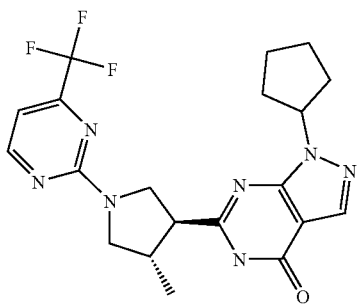

To a solution of 1-cyclopentyl-6-[(3,4-trans)-4-methylpyrrolidin-3-yl]-1H-pyrazolo[3,4-d]pyrimidin-4(5H)-one (40 mg) in dimethylformamide (1 ml) was added cesium carbonate (2 eq.) and 2-chloro-4-(trifluoromethyl)pyrimidine (1.2 eq.) and the reaction mixture was heated at 60° C. for 90 min. The reaction mixture was poured into saturated sodium bicarbonate, extracted with methylene chloride, dried with magnesium sulfate, filtered and concentrated. Purification via MPLC Biotage chromatography eluting with 20-60% ethyl acetate/hexanes provided 40 mg of the title compound. 400 MHz $^1$H NMR (CDCl$_3$) δ 8.51 (d, J=5.0 Hz, 1H), 8.02 (m, 1H), 6.79 (d, J=4.6 Hz, 1H), 5.16-5.08 (m, 1H), 4.24-3.97 (m, 3H), 3.37-3.32 (m, 1H), 3.20-3.14 (m, 1H), 2.09-2.05 (m, 3H), 1.96-1.90 (m, 1H), 1.73-1.56 (m, 5H), 1.24 (d, J=6.6 Hz, 3H). MS: (M$^+$H m/z=434.1).

Example 5

1-cyclopentyl-6-[(3,4-trans)-4-methyl-1-pyrimidin-2-ylpyrrolidin-3-yl]-1,5-dihydro-4H-pyrazolo[3,4-d]pyrimidin-4-one

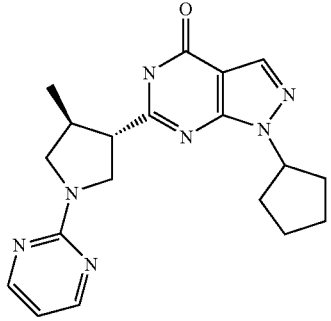

Following the procedure for the preparation of 1-cyclopentyl-6-{(3,4-trans)-4-methyl-1-[4-(trifluoromethyl)pyrimidin-2-yl]pyrrolidin-3-yl}-1,5-dihydro-4H-pyrazolo[3,4-d]pyrimidin-4-one but substituting 2-chloropyrimidine provided the title compound. 400 MHz $^1$H NMR (CD$_3$OD) δ 8.29 (d, J=5.0 Hz, 2H), 7.96 (s, 1H), 6.60 (t, J=5.0 Hz, 1H), 5.08-5.04 (m, 1H), 4.06-3.87 (m, 3H), 3.23-3.18 (m, 1H), 3.12 (q, J=7.9 Hz, 1H), 2.80-2.76 (m, 1H), 2.05-1.98 (m, 4), 1.90-1.82 (m, 2H), 1.66-1.61 (m, 2H), 1.17 (d, J=7.1 Hz, 3H). MS: (M$^+$H m/z=366.1).

Example 6

6-[(3,4-trans)-1-benzoyl-4-methylpyrrolidin-3-yl]-1-cyclopentyl-1,5-dihydro-4H-pyrazolo[3,4-d]pyrimidin-4-one

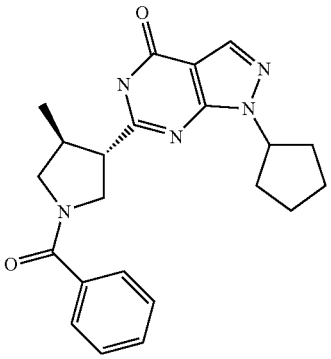

To a solution of 1-cyclopentyl-6-[(3,4-trans)-4-methylpyrrolidin-3-yl]-1H-pyrazolo[3,4-d]pyrimidin-4(5H)-one (40 mg) in methylene chloride (1 ml) was added triethyl amine (2.5 eq.) and benzoyl chloride (1.2 eq.) and the reaction mixture was stirred at ambient temperature for 1 h. The reaction mixture was poured into saturated sodium bicarbonate, extracted with methylene chloride, dried with magnesium sulfate, filtered and concentrated. Biotage MPLC chromatography eluting with 2-4% methanol/methylene chloride provided the title compound (27 mg). 400 MHz $^1$H NMR (CDCl$_3$) δ 8.06-8.03 (m, 1H), 7.57-7.50 (m, 2H), 7.43-7.37 (m, 3H), 5.20-5.13 (m, 1H), 4.16-4.03 (m,1H), 3.92 (d, J=8.3 Hz, 1H), 3.81-3.76 (m, 1H), 3.47-3.29 (m, 1H), 3.17-3.03 (m, 1H), 2.84-2.67 (m, 1H), 2.11-1.80 (m, 3H), 1.79-1.72 (m, 1H), 1.56-1.30 (m, 4H), 1.21-1.11 (m, 3H). MS: (M$^+$H m/z=392.1).

Example 7

1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one

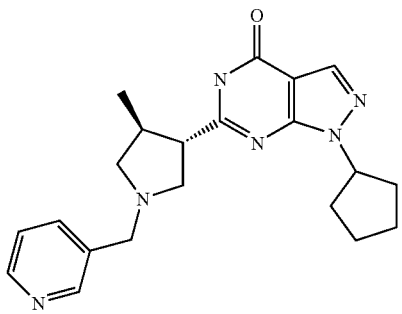

To a solution of 1-cyclopentyl-6-[(3,4-trans)-4-methylpyrrolidin-3-yl]-1H-pyrazolo[3,4-d]pyrimidin-4(5H)-one (40 mg) in 1,2-dichloroethane (2 mL) was added acetic acid (2 eq.), nicotinaldehyde (1.5 eq.) and sodium triacetoxy borohydride (58 mg). The reaction mixture was heated at 40° C. for 4 h, poured into saturated sodium bicarbonate, extracted with methylene chloride, dried with magnesium sulfate, filtered and concentrated. Purification via Biotage MPLC chromatography eluting with 1-4% methanol/methylene chloride/ 0.5% ammonium hydroxide provided the title compound (47 mg). 400 MHz $^1$H NMR (CDCl$_3$) δ 8.55 (m, 2H), 2.02 (s, 1H), 7.84 (m, 1H), 7.36 (m, 1H), 5.16-5.09 (m, 1H), 3.82-3.60 (m, 2H), 3.36 (m, 1H), 3.05-2.38 (m, 4H), 2.13-1.89 (m, 7H), 1.73-1.68 (m, 2H), 1.21 (m, J=7.1 Hz, 3H). MS: (M$^+$H m/z=379.1).

Example 8

1-cyclopentyl-6-{(3,4-trans)-4-methyl-1-[3-(trifluoromethyl)benzyl]pyrrolidin-3-yl}-1,5-dihydro-4H-pyrazolo[3,4-d]pyrimidin-4-one

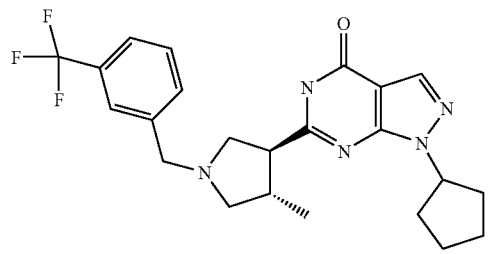

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 3-(trifluoromethyl)benzaldehyde provided the title compound. 400 MHz $^1$H NMR (CDCl$_3$) δ 8.02 (s, 1H), 7.66 (s, 1H), 7.53-7.50 (m, 3H), 5.16-5.09 (m, 1H), 3.80 (m, 1H), 3.69-3.66 (m, 1H), 3.35 (m, 1H), 2.99 (m, 1H), 2.83 (m, 1H), 2.42 (m, 1H), 2.12-1.93 (m, 7), 1.74-1.68 (m, 2H), 1.56 (m, 1H), 1.21 (d, J=6.6 Hz, 3H). MS: (M$^+$H m/z=446.0).

Example 9

1-cyclopentyl-6-[(3,4-trans)-4-methyl-1-(quinolin-2-ylmethyl)pyrrolidin-3-yl]-1,5-dihydro-4H-pyrazolo[3,4-d]pyrimidin-4-one

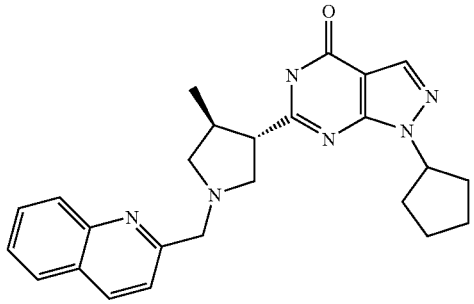

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting quinoline-2-carbaldehyde provided the title compound. 400 MHz $^1$H NMR (CDCl$_3$) δ 8.22-8.15 (m, 2H), 8.07 (s, 1H), 7.80 (d, J=7.9 Hz, 1H), 7.71 (t=8.3 Hz, 1H), 7.69-7.50 (m, 2H), 5.18-5.11 (m, 1H), 4.25 (m, 1H), 3.91 (m, 1H), 3.71 (m, 1H), 3.49 (m, 1H), 3.17 (m, 1H), 2.87 (m, 1H), 2.73-2.45 (m, 2H), 2.13-1.94 (m, 6H), 1.75-1.68 (m, 2H), 1.23 (d, J=7.1 Hz, 3H). MS: (M$^+$H m/z=429.1).

Example 10

1-cyclopentyl-6-[(3,4-trans)-4-methyl-1-(quinolin-4-ylmethyl)pyrrolidin-3-yl]-1,5-dihydro-4H-pyrazolo[3,4-d]pyrimidin-4-one

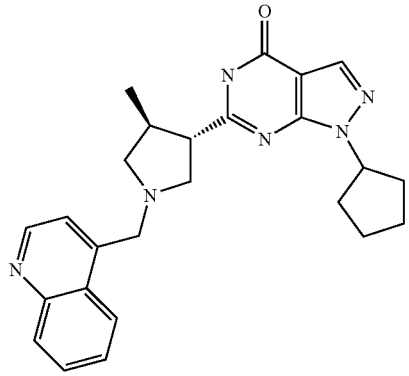

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting quinoline-4-carbaldehyde provided the title compound. 400 MHz $^1$H NMR (CDCl$_3$) δ 8.92-8.89 (m, 1H), 8.27-8.25 (m, 1H), 8.18-8.16 (m, 1H), 8.00 (s, 1H), 7.80-7.74 (m, 2H), 7.63-7.50 (m, 1H), 5.14-5.07 (m, 1H), 4.18 (m, 2H), 3.37 (m, 1H), 3.10-2.30 (m, 5H), 2.15-1.93 (m, 6H), 1.74-1.64 (m, 2H), 1.21 (d, J=6.6 Hz, 3H). MS: (M$^+$H m/z=429.1).

Example 11

1-cyclopentyl-6-[(3,4-trans)-4-methyl-1-{[6-(trifluoromethyl)pyridin-3-yl]methyl}pyrrolidin-3-yl]-1,5-dihydro-4H-pyrazolo[3,4-d]pyrimidin-4-one

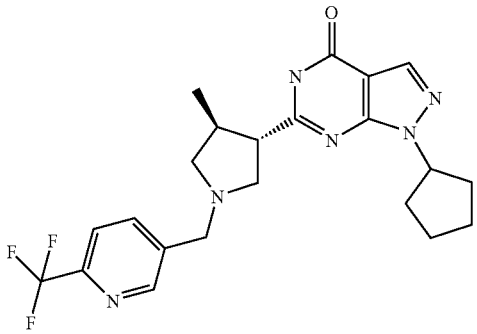

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 6-(trifluoromethyl)nicotinaldehyde provided the title compound. 400 MHz $^1$H NMR (CDCl$_3$) δ 8.63 (m, 1H), 8.01 (s, 1H), 7.7 (d, J=7.80 Hz, 1H), 5.12 (m, 1H), 4.82 (m, 1H), 3.79 (q, J=13.2, 16.2, Hz, 2H), 3.32 (t, J=8.5 Hz, 1H), 3.02 (m, 1H), 2.86 (m, 1H), 2.63 (m, 1H), 2.45 (m, 1H), 2.12-2.88 (m, 6H), ), 1.74-1.64 (m, 3H), 1.32 (d, J=7.05 Hz, 3H). MS: (M$^+$H m/z=447.0).

Example 12

1-cyclopentyl-6-[(3,4-trans)-4-methyl-1-(quinoxalin-2-ylmethyl)pyrrolidin-3-yl]-1,5-dihydro-4H-pyrazolo[3,4-d]pyrimidin-4-one

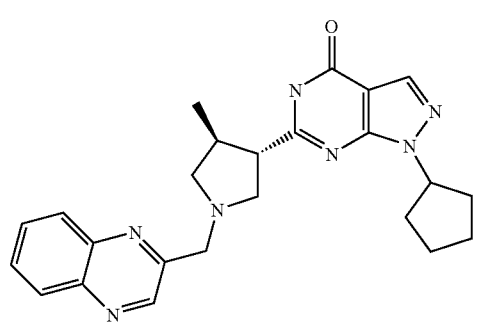

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting quinoxaline-2-carbaldehyde provided the title compound. 400 MHz $^1$H NMR (CDCl$_3$) δ 8.86 (s, 1H), 8.31-8.29 (m, 1H), 8.05-8.08 (m, 2H), 7.79-7.70 (m, 2H), 5.16-5.12 (m, 1H), 4.32-4.28 (m, 1H), 3.94-3.98 (m, 1H), 3.46 (t, J=8.3 Hz, 1H), 3.26 (d, J=9.5 Hz, 1H), 2.90-2.88 (m, 1H), 2.64-2.60 (m, 1H), 2.50-2.47 (m, 1H), 2.18 (t, J=8.3 Hz, 1H), 2.11-1.91 (m, 6H), 1.71-1.66 (m, 2H), 1.23 (d, J=7.05 Hz, 3H). MS: (M+H m/z=430.1).

Example 13

1-cyclopentyl-6-[(3,4-trans)-4-methyl-1-(quinoxalin-6-ylmethyl)pyrrolidin-3-yl]-1,5-dihydro-4H-pyrazolo[3,4-d]pyrimidin-4-one

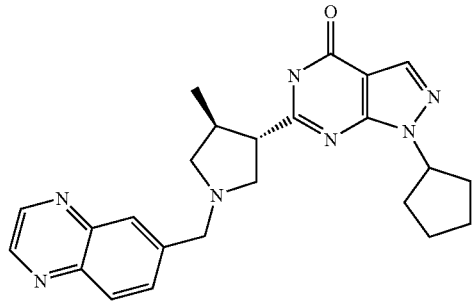

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting quinoxaline-6-carbaldehyde provided the title compound. 400 MHz ¹H NMR (CDCl₃) δ 8.82 (s, 2H), 8.14 (d, J=8.3 Hz, 1H), 8.07-7.93 (m, 3H), 5.15-5.08 (m, 1H), 4.00-3.87 (m, 2H), 3.37 (t, J=8.7 Hz, 1H), 3.04 (d, J=9.5 Hz, 1H), 2.85-2.84 (m, 1H), 2.66-2.62 (m, 1H), 2.46-2.42 (m, 1H), 2.11-1.92 (m, 7H), 1.71-1.63 (m, 2H), 1.20 (d, J=7.05 Hz, 3H). MS: (M+H m/z=430.1).

Example 14

1-cyclopentyl-6-[(3,4-trans)-4-methyl-1-(pyrimidin-5-ylmethyl)pyrrolidin-3-yl]-1,5-dihydro-4H-pyrazolo[3,4-d]pyrimidin-4-one

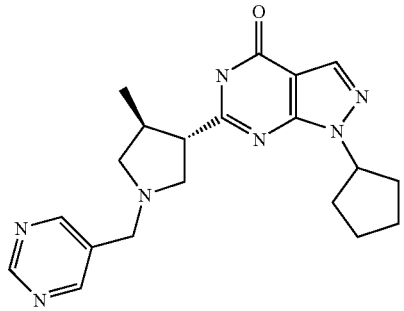

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting pyrimidine-5-carbaldehyde provided the title compound. 400 MHz ¹H NMR, (CDCl₃) δ 9.16 (s, 1H), 8.76 (s, 2H), 8.02 (s, 1H), 5.17-5.10 (m, 1H), 3.78-3.69 (m, 2H), 3.27 (t, J=8.7 Hz, 1H), 3.07 (d, J=9.5 Hz, 1H), 2.89 (m, 1H), 2.69 (m, 1H), 2.48-2.46 (m, 1H), 2.12-1.89 (m, 6H), 1.74-1.63 (m, 3H), 1.26-1.19 (m, 3H). MS: (M+H m/z=380.1).

Example 15

1-cyclopentyl-6-[(3,4-trans)-1,4-dimethylpyrrolidin-3-yl]-1,5-dihydro-4H-pyrazolo[3,4-d]pyrimidin-4-one

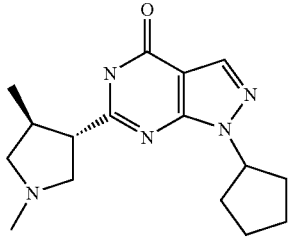

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting formaldehyde provided the title compound. 400 MHz ¹H NMR, (CDCl₃) δ 8.04 (s, 1H), 5.18-5.11 (m, 1H), 3.39 (m, 1H), 3.15 (m, 1H), 3.03-2.96 (m, 1H), 2.70 (m, 1H), 2.51 (m, 4H), 2.15-1.90 (m, 7H), 1.75-1.66 (m, 2H), 1.20 (d, J=6.6 Hz, 3H). MS: (M+H m/z=302.2).

Example 16

1-cyclopentyl-6-[(3,4-trans)-4-methyl-1-(2,2,2-trifluoroethyl)pyrrolidin-3-yl]-1,5-dihydro-4H-pyrazolo[3,4-d]pyrimidin-4-one

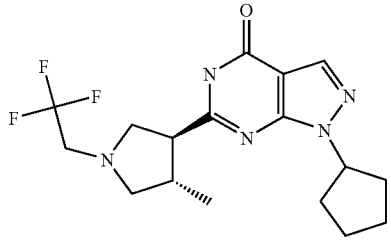

To a solution of 1-cyclopentyl-6-[(3,4-trans)-4-methylpyrrolidin-3-yl]-1H-pyrazolo[3,4-d]pyrimidin-4(5H)-one (40 mg) in dimethyl formamide (1.5 mL) was added sodium carbonate (30 mg) and 1,1,1-trifluoro-2-iodoethane (1.1 eq.). The reaction mixture was heated at 40° C. for 3 days. An additional 3 eq. of 1,1,1-trifluoro-2-iodoethane along with cesium carbonate (2 eq.) and the reaction mixture was heated at 60° C. for 3 days. The reaction mixture was poured into saturated sodium bicarbonate, extracted with methylene chloride, dried with magnesium sulfate, filtered and concentrated. Purification via MPLC Biotage eluting with 0.5-2% methanol/methylene chloride/0.5% ammonium hydroxide provided the title compound (9 mg). 400 MHz $^1$H NMR, (CDCl$_3$) δ 8.03 (s, 1H), 5.16-5.10 (m, 1H), 3.50-3.48 (m, 1H), 3.30-3.25 (m, 2H), 2.52 (m, 1H), 2.25 (m, 1H), 2.13-1.94 (m, 5H), 1.72-1.57 (m, 6H), 1.22 (d, J=7.1 Hz, 3H). MS: (M$^+$H m/z=370.1).

Example 17

1-cyclopentyl-6-{(3,4-trans)-4-methyl-1-[(2-methylpyridin-3-yl)methyl]pyrrolidin-3-yl}-1,5-dihydro-4H-pyrazolo[3,4-d]pyrimidin-4-one

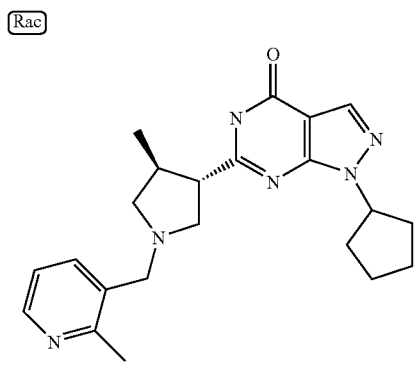

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 2-methylnicotinaldehyde provided the title compound. 400 MHz $^1$H NMR (CDCl$_3$) δ 8.40-8.39 (m, 1H), 7.99 (s, 1H), 7.62-7.60 (m, 1H), 7.12-7.09 (m, 1H), 5.15-5.08 (m, 1H), 3.73-3.65 (m, 2H), 3.30 (t, J=8.7 Hz, 1H), 3.04 (d, J=9.95 Hz, 1H), 2.86-2.84 (m, 1H), 2.66-2.62 (m, 4H), 2.46-2.39 (m, 1H), 2.11-1.89 (m, 7H), 1.71-1.64 (m, 2H), 1.19 (d, J=7.05 Hz, 3H). MS: (M$^+$H m/z=393.2).

Example 18

1-cyclopentyl-6-[(3,4-trans)-4-methyl-1-(quinolin-8-ylmethyl)pyrrolidin-3-yl]-1,5-dihydro-4H-pyrazolo[3,4-d]pyrimidin-4-one

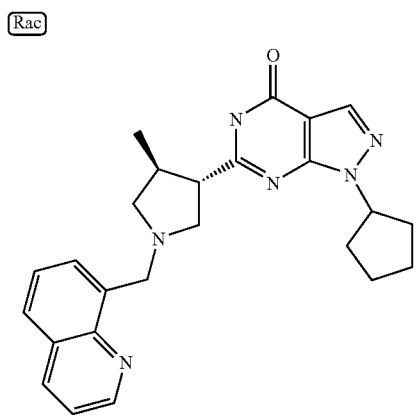

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting quinoline-5-carbaldehyde provided the tide compound. 400 MHz $^1$H NMR (CDCl$_3$) δ 9.10-9.09 (m, 1H), 8.13 (dd, J=8.3, 1.6 Hz, 1H), 7.98 (s, 1H), 7.76-7.74 (d, J=7.88 Hz, 2H), 7.50 (t, J=7.88 Hz, 1H), 7.45-7.42 (m, 1H), 5.14-5.07 (m, 1H), 4.52 (d, J=12.40 Hz, 1H), 4.21 (d, J=12.40 Hz, 1H), 3.34 (t, J=8.3 Hz, 1H), 3.1 (d, J=9.95 Hz, 1H), 2.8-2.79 (m, 1H), 2.71-2.67 (m, 1H), 2.37-2.31 (m, 1H), 2.10-1.88 (m, 7H), 1.72-1.62 (m, 2H), 1.17 (d, J=6.64 Hz, 3H). MS: (M$^+$H m/z=429.2).

Example 19

1-cyclopentyl-6-[(3,4-trans)-4-methyl-1-(quinolin-3-ylmethyl)pyrrolidin-3-yl]-1,5-dihydro-4H-pyrazolo[3,4-d]pyrimidin-4-one

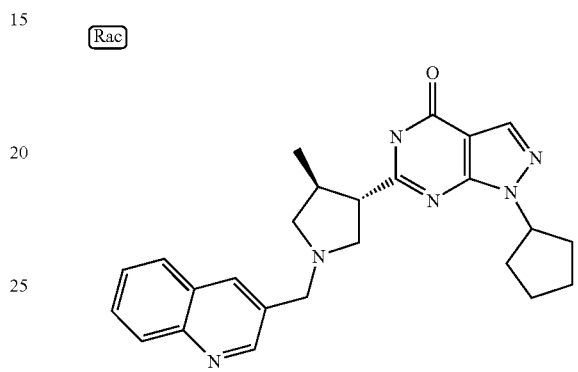

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting quinoline-3-carbaldehyde provided the title compound. 400 MHz $^1$H NMR (CDCl$_3$) δ 8.87 (s, 1H), 8.29 (s, 1H), 8.07 (d, J=7.8 Hz, 1H), 8.02 (s, 1H), 7.89 (d, J=7.9 Hz, 1H), 7.70-7.66 (m, 1H), 7.54 (t, J=7.5 Hz, 1H), 5.16-5.08 (m, 1H), 4.02-3.98 (m, 1H), 3.86-3.83 (m, 1H), 3.47 (s, 1H), 3.40 (t, J=8.3 Hz, 1H), 3.07 (d, J=8.5 Hz, 1H), 2.85 (m, 1H), 2.65-2.61 (m, 1H), 2.47-2.46 (m, 1H), 2.15-1.87 (m, 6H), 1.73-1.63 (m, 2H), 1.20 (d, J=7.1 Hz, 3H). MS: (M$^+$H m/z=429.2).

Example 20

1-cyclopentyl-6-{(3,4-trans)-4-methyl-1-[(6-methylpyridin-3-yl)methyl]pyrrolidin-3-yl}-1,5-dihydro-4H-pyrazolo[3,4-d]pyrimidin-4-one

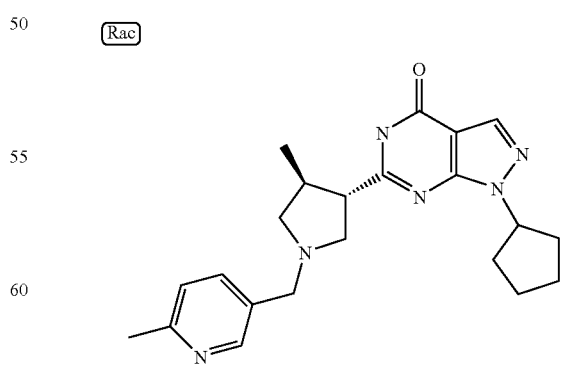

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 6-methyinicotinaldehyde provided the title compound. 400 MHz $^1$H NMR (CDCl$_3$) δ 8.37 (d, J=1.2 Hz, 1H), 8.00 (s, 1H), 7.73 (dd, J=7.9, 2.1 Hz, 1H), 7.18 (d, J=8.3 Hz, 1H), 5.16-5.08 (m, 1H), 3.76-3.72 (m, 1H), 3.61-3.57 (m, 1H), 3.32 (t, J=8.71 Hz, 1H), 2.98 (d, J=9.9 Hz, 1H), 2.83-2.81 (m, 1H), 2.57-2.51 (m, 4H), 2.42-2.38 (m, 1H), 2.11-1.89 (m, 7H), 1.72-1.64 (m, 2H), 1.19 (d, J=7.1 Hz, 3H). MS: (M$^+$H m/z=393.2).

Example 21

(a) (3,4-trans)-methyl 1-benzyl-4-isopropylpyrrolidine-3-carboxylate

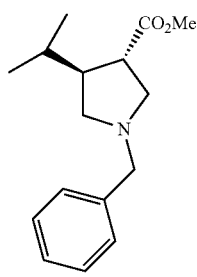

Following the procedure for the preparation of (3,4-trans)-methyl 1-benzyl-4-methyl pyrrolidine-3-carboxylate but substituting (E)-methyl 4-methylpent-2-enoate provided the title compound. 400 MHz $^1$H NMR (CDCl$_3$) δ 7.31-7.20 (m, 5H), 3.66 (s, 3H), 3.62-3.49 (m, 2H), 2.79-2.69 (m, 3H), 2.31-2.27 (m, 2H), 1.61-1.56 (m, 1H), 1.27-4.25 (m, 1H), 0.86 (t, J=2.9 Hz, 6H). MS: (M$^+$H m/z=262.2).

(b) 6-[(3,4-trans)-1-benzyl-4-isopropylpyrrolidin-3-yl]-1-cyclopentyl-1,5-dihydro-4H-pyrazolo[3,4-d]pyrimidin-4-one

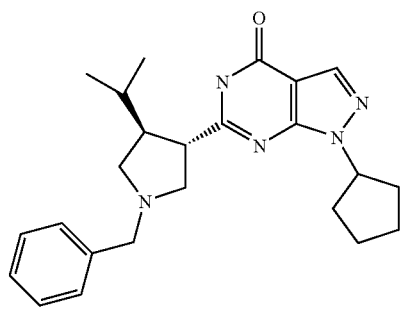

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide and (3,4-trans)-methyl 1-benzyl-4-isopropylpyrrolidine-3-carboxylate provided the title compound. 400 MHz $^1$H NMR (CDCl$_3$) δ 8.00 (s, 1H), 7.38-7.32 (m, 4H), 7.27-7.24 (m, 1H), 5.13-5.05 (m, 1H), 3.78 (d, J=12.5 Hz, 1H), 3.6 (d, J=12.5 Hz, 1H), 3.27-3.21 (m, 1H), 2.98-2.96 (m, 2H), 2.37 (m, 1H), 2.10-1.88 (m, 7H), 1.69-1.60 (m, 3H), 0.98 (d, J=6.6 Hz, 3H), 0.86 (d, J=6.6 Hz, 3H), MS: (M$^+$H m/z=406.1).

Example 22

(a) 5-amino-1-cyclopentyl-3-methyl-1H-pyrazole-4-carbonitrile

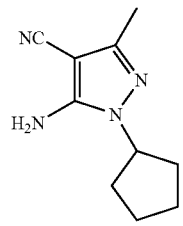

Following the procedure for the preparation of 5-amino-1-(2-methoxyphenyl)-1H-pyrazole-4-carbonitrile but substituting 1-cyclopentylhydrazine and 2-(1-methoxyethylidene)malononitrile provided the title compound. $^1$H NMR (300 MHz, CDCl3): δ 4.24 (m, 3H), 2.24 (s, 3H), 2.01 (m, 4H), 1.90 (m, 2H), 1.67 (m, 2H).

(b) 5-amino-1-cyclopentyl-3-methyl-1H-pyrazole-4-carboxamide

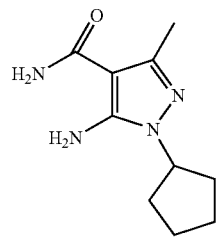

Following the procedure for the preparation of 5-amino-1-(2-methoxyphenyl)-1H-pyrazole-4-carboxamide but substituting 5-amino-1-cyclopentyl-3-methyl-1H-pyrazole-4-carbonitrile provided the title compound. $^1$H NMR (300 MHz, CDCl3): δ 5.39 (br, 2H), 5.32 (br, 2H), 4.26 (m, 1H), 2.38 (s, 3H), 2.04 (m, 4H), 1.9 (m, 2H), 1.66 (m, 2H).

(c) 6-[(3,4-trans)-1-benzyl-4-methylpyrrolidin-3-yl]-1-cyclopentyl-3-methyl-1,5-dihydro-4H-pyrazolo[3,4-d]pyrimidin-4-one

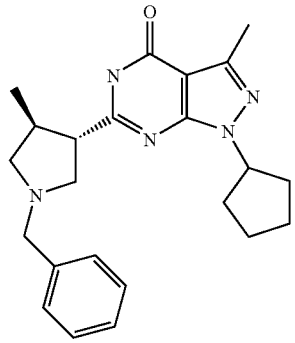

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-3-methyl-1H-pyrazole-4-carboxamide provided the title compound. 400 MHz $^1$H NMR (CDCl₃) δ 7.45-7.20 (m, 5H), 5.13-4.96 (m, 1H), 3.85-3.61 (m, 2H), 3.45-3.30 (m, 1H), 3.08-2.98 (m, 1H), 2.82-2.74 (m, 1H), 2.60-2.45 (m, 4H), 2.45-2.30 (m, 1H), 2.18-1.80 (m, 6H), 1.79-1.50 (m, 3H), 1.2-1.1 (m, 3H). MS: (M⁺H m/z=392.5).

Example 23

(a) 1-cyclopentyl-6-[(3S,4S)-4-methylpyrrolidin-3-yl]-1H-pyrazolo[3,4-d]pyrimidin-4(5H)-one

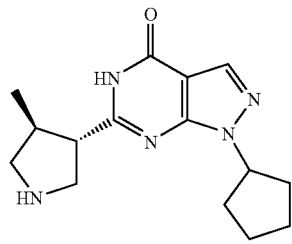

A solution of 6-[(3S,4S)-1-benzyl-4-methylpyrrolidin-3-yl]-1-cyclopentyl-1,5-dihydro-4H-pyrazolo[3,4-d]pyrimidin-4-one (9.25 g) in ethanol 100 mL was added to a Parr bottle. 2 mL of concentrated HCl followed by 3 g of palladium hydroxide was added. The reaction mixture was placed on a hydrogenator under 45 psi of H₂ gas for 4 h. The reaction mixture was filtered through Celite and concentrated to provide the title compound as an HCl salt. 400 MHz ¹H NMR (CDCl₃) δ 8.00 (s, 1H), 5.14-5.10 (m, 1H), 4.89-3.84 (m, 1H), 3.72-3.67 (m, 1H), 3.38-3.31 (m, 1H), 3.03-2.98 (m, 1H), 2.85-2.81 (m, 1H), 2.08-1.85 (m, 7H), 1.69-1.61 (m, 2H), 1.19-1.10 (m, 3H). MS: (M⁺H m/z=288.2).

(b) 1-cyclopentyl-6-[(3S,4S)-4-methyl-1-(quinoxalin-6-ylmethyl)pyrrolidin-3-yl]-1,5-dihydro-4H-pyrazolo[3,4-d]pyrimidin-4-one

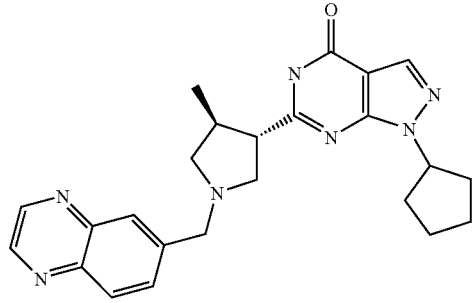

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and quinoxaline-6-carbaldehyde provided the title compound. 400 MHz ¹H NMR (CDCl₃) δ 8.82 (s, 2H), 8.14 (d, J=8.3 Hz, 1H), 8.07-7.93 (m, 3H), 5.15-5.08 (m, 1H), 4.00-3.87 (m, 2H), 3.37 (t, J=8.7 Hz, 1H), 3.04 (d, J=9.5 Hz, 1H), 2.85-2.84 (m, 1H), 2.66-2.62 (m, 1H), 2.46-2.42 (m, 1H), 2.11-1.92 (m, 7H), 1.71-1.63 (m, 2H), 1.20 (d, J=7.05 Hz, 3H), MS: (M⁺H m/z=430.1).

Example 24

1-cyclopentyl-6-[(3,4-trans)-4-methyl-1-(2-phenylethyl)pyrrolidin-3-yl]-1,5-dihydro-4H-pyrazolo[3,4-d]pyrimidin-4-one

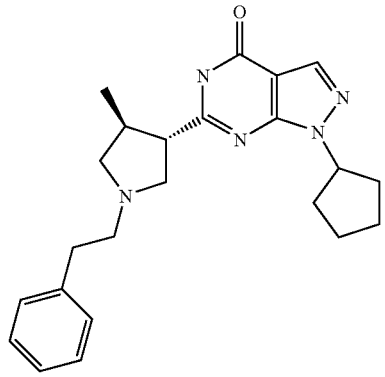

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 2-phenylacetaldehyde provided the title compound. 400 MHz ¹H NMR (CDCl₃) δ 8.03 (s, 1H), 7.32-7.19 (m, 5H), 5.18-5.11 (m, 1H), 3.44 (t, J=8.7 Hz, 1H), 3.14 (d, J=9.9 Hz, 1H), 2.90-2.78 (m, 5H), 2.56-2.52 (m, 1H), 2.40-2.39 (m, 1H), 2.14-1.89 (m, 7H), 1.73-1.67 (m, 2H), 1.19 (d, J=7.05 Hz, 3H). MS: (M⁺H m/z=392.1).

Example 25

1-cyclopentyl-6-{(3,4-trans)-1-[(6-methoxypyridin-3-yl)methyl]-4-methylpyrrolidin-3-yl}-1,5-dihydro-4H-pyrazolo[3,4-d]pyrimidin-4-one

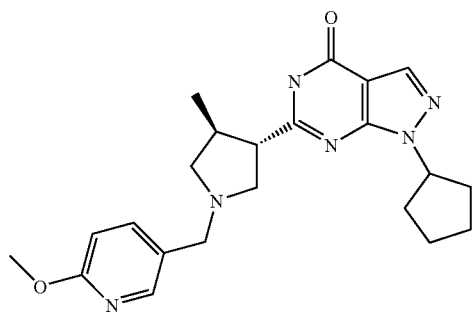

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 6-methoxynicotinaldehyde provided the title compound. 400 MHz ¹H NMR (CDCl₃) δ 8.01 (dd, J=31.5, 2.5 Hz, 1H), 8.00 (s, 1H), 7.69 (dd, J=8.3, 2.5 Hz, 1H), 6.76 (d, J=8.3 Hz, 1H), 5.16-5.09 (m, 1H), 3.90 (s, 3H), 3.68 (d, J=12.9 Hz, 1H), 3.55 (d, J=12.9 Hz, 1H), 3.31 (t, J=8.7 Hz, 1H), 2.98 (d, J=9.9 Hz, 1H), 2.81-2.79 (m, 1H), 2.54-2.50 (m, 1H), 2.41-2.36 (m, 1H), 2.12-1.87 (m, 7H), 1.73-1.64 (m, 2H), 1.18 (d, J=7.05 Hz, 3H). MS: (M+H m/z=409.1).

Example 26

1-cyclopentyl-6-[(3,4-trans)-4-methyl-1-(pyridin-2-ylmethyl)pyrrolidin-3-yl]-1,5-dihydro-4H-pyrazolo[3,4-d]pyrimidin-4-one

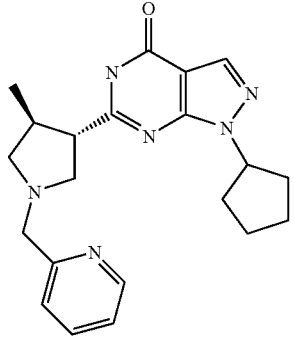

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting picolinaldehyde provided the title compound. 400 MHz $^1$H NMR (CDCl$_3$) δ 8.63-8.62 (m, 1H), 8.02 (s, 1H), 7.72-7.67 (m, 1H), 7.41 (d, J=7.9 Hz, 1H), 7.20-7.17 (m, 1H), 5.18-5.10 (m, 1H), 4.03 (d, J=13.7 Hz, 1H), 3.75 (d, J=13.7 Hz, 1H), 3.41 (t, J=8.3 Hz, 1H), 3.07 (d, J=9.9 Hz, 1H), 2.83-2.82 (m, 1H), 2.58 (m, 1H), 2.46-2.40 (m, 1H), 2.13-1.89 (m, 7H), 1.74-1.64 (m, 2H), 1.21 (d, J=7.1 Hz, 3H). MS: (M+H m/z=379.1).

Example 27

1-cyclopentyl-6-{(3,4-trans)-4-methyl-1-[(3-methylpyridin-2-yl)methyl]pyrrolidin-3-yl}-1,5-dihydro-4H-pyrazolo[3,4-d]pyrimidin-4-one

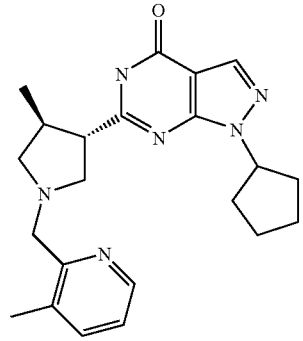

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 3-methylpicolinaldehyde provided the title compound. 400 MHz $^1$H NMR (CDCl$_3$) δ 8.02 (s, 1H), 7.57 (t, J=7.5, 1H), 7.22 (d, J=7.8 Hz, 1H), 7.02 (d, J=7.5 Hz, 1H), 5.17-5.09 (m, 1H), 3.97 (d, J=13.3 Hz, 1H), 3.68 (d, J=13.3 Hz, 1H), 3.42 (t, J=8.3 Hz, 1H), 3.05 (d, J=9.9 Hz, 1H), 2.82-2.80 (m, 1H), 2.57-2.53 (m, 1H), 5.54 (s, 3H), 2.44-2.38 (m, 1H), 2.12-1.89 (m, 7H), 1.72-1.64 (m, 2H), 1.19 (d, J=7.05 Hz, 3H). MS: M+H m/z=393.1).

Example 28

(a) (3,4-trans)-ethyl 1-benzyl-4-ethylpyrrolidine-3-carboxylate

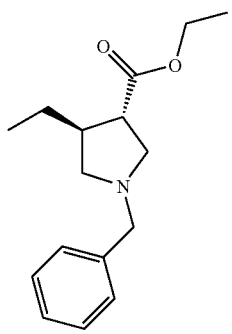

Following the procedure for the preparation of (3,4-trans)-methyl 1-benzyl-4-methylpyrrolidine-3-carboxylate but substituting (E)-methyl pent-2-enoate provided the title compound. 400 MHz $^1$H NMR (CDCl$_3$) δ 7.33-7.19 (m, 5H), 4.15-4.08 (m, 2H), 3.65-3.52 (m, 2H), 2.82-2.71 (m, 3H), 2.60-2.55 (m, 1H), 2.38-2.24 (m, 2H), 1.59-1.50 (m, 1H), 1.47-1.38 (m, 1H), 1.23 (t, J=7.5 Hz, 3H), 0.87 (t, J=7.1 Hz, 3H). MS: (M+H m/z=262.2).

(b) 6-[(3,4-trans)-1-benzyl-4-ethylpyrrolidin-3-yl]-1-cyclopentyl-1,5-dihydro-4H-pyrazolo[3,4-d]pyrimidin-4-one

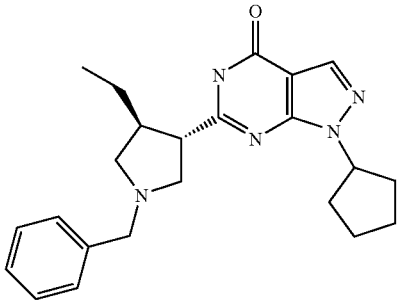

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide and (3,4-trans)-methyl 1-benzyl-4-ethylpyrrolidine-3-carboxylate provided the title compound. 400 MHz $^1$H NMR (CDCl$_3$) δ 8.00 (s, 1H), 7.39-7.24 (m, 5H), 5.13-5.07 (m, 1H), 3.78 (d, J=13.3 Hz, 1H), 3.58 (d, J=12.9 Hz, 1H), 3.42 (t, J=12.9 Hz, 1H), 3.33 (t, J=8.7 Hz, 1H), 2.98 (d, J=9.9 Hz, 1H), 2.86 (m, 1H), 2.46-2.42 (m, 1H), 2.19-1.44 (m,11H), 0.92 (t, J=7.05 Hz, 3H). MS (M+H m/z=392.1).

Example 29

(a) (3,4-trans)-methyl-1-benzyl-4-cyclopropylpyrrolidine-3-carboxylate

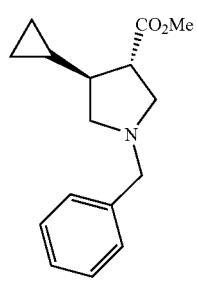

Following the procedure for the preparation of (3,4-trans)-methyl 1-benzyl-4-methylpyrrolidine-3-carboxylate but substituting (E)-methyl 3-cyclopropylacrylate provided the title compound. 400 MHz $^1$H NMR (CDCl$_3$) δ 7.33-7.20 (m, 5H), 3.66 (s, 3H), 3.64-3.54 (m, 2H), 2.87-2.81 (m, 2H), 2.77-2.70 (m, 2H), 2.47-2.43 (m, 1H), 1.84-1.78 (m, 1H), 0.87-0.79 (m, 1H), 0.45-0.36 (m, 2H), 0.20-0.06 (m, 2H). MS: (M+H m/z=260.2).

(b) 6-[(3,4-trans)-1-benzyl-4-cyclopropylpyrrolidin-3-yl]-1-cyclopentyl-1,5-dihydro-4H-pyrazolo[3,4-d]pyrimidin-4-one

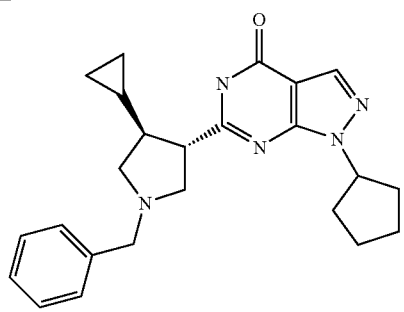

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide and (3,4-trans)-methyl-1-benzyl-4-cyclopropylpyrrolidine-3-carboxylate provided the title compound. 400 MHz $^1$H NMR (CDCl$_3$) δ 7.99 (s, 1H), 7.38-7.31 (m, 4H), 7.27-7.23 (m, 1H), 5.14-5.10 (m, 1H), 3.78 (d, J=12.4 Hz, 1H), 3.63 (d, J=12.4 Hz, 1H), 3.32 (t, J=8.7 Hz, 1H), 3.12-3.10 (m, 1H), 3.01 (d, J=9.9 Hz, 1H), 2.59-2.57 (m, 1H), 2.20-1.87 (m, 8H), 1.71-1.65 (m, 2H), 0.86-0.84 (m, 1H), 0.52-0.48 (m, 2H), 0.19-0.09 (m, 2H). MS: (M+H m/z=393.1).

Example 30

(a) 5-amino-1-isopropyl-1H-pyrazole-4-carbonitrile

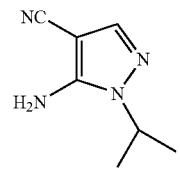

Following the procedure for the preparation of 5-amino-1-(2-methoxyphenyl)-1H-pyrazole-4-carbonitrile but substituting 1-isopropylhydrazine provided the title compound. 400 MHz $^1$H NMR (CDCl$_3$) δ 7.50 (s, 1H), 4.22-4.16 (m, 3H), 1.45 (d, J=6.6 Hz, 6H). MS: (M+H m/z=151.1).

(b) 5-amino-1-isopropyl-1H-pyrazole-4-carboxamide

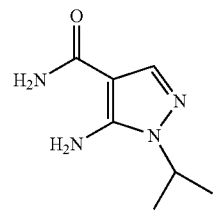

Following the procedure for the preparation of 5-amino-1-(2-methoxyphenyl)-1H-pyrazole-4-carboxamide but substituting 5-amino-1-isopropyl-1H-pyrazole-4-carbonitrile provided the title compound. 400 MHz $^1$H NMR (CDCl$_3$) δ 7.67 (s, 1H), 4.40-4.33 (m, 1H), 1.37 (d, J=6.6 Hz, 6H). MS: (M+H m/z=169.1).

(c) 6-[(3,4-trans)-1-benzyl-4-methylpyrrolidin-3-yl]-1-isopropyl-1,5-dihydro-4H-pyrazolo[3,4-d]pyrimidin-4-one

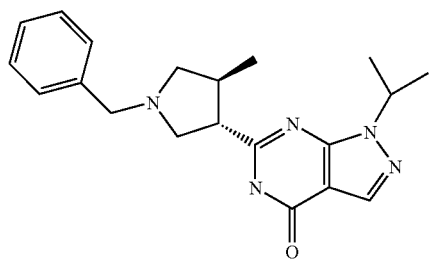

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-isopropyl-1H-pyrazole-4-carboxamide provided the title compound.

400 MHz $^1$H NMR (CDCl$_3$) δ 7.98 (s, 1H), 7.38-7.22 (m, 5H), 5.07-5.04 (m, 1H), 3.77-3.64 (m, 2H), 3.12-3.08 (m,

1H), 2.99-2.91 (m, 3H), 2.67-2.63 (m, 1H), 2.27-2.25 (m, 1H), 1.48 (d, J=7.1 Hz, 6H), 1.14 (d, J=6.6 Hz, 3H). MS: (M⁺H m/z=352.1).

Example 31

6-[(3S,4S)-1-benzyl-4-methylpyrrolidin-3-yl]-1-isopropyl-1,5-dihydro-4H-pyrazolo[3,4-d]pyrimidin-4-one

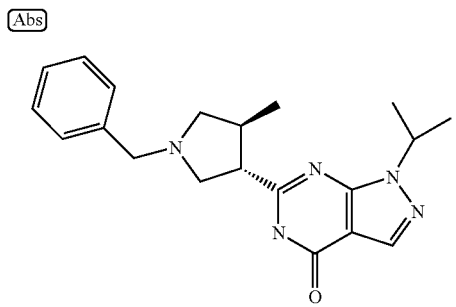

The racemate was separated on Chiralcel OD chiral HPLC column, Mobile Phase 90/10 Heptane/EtOH, T$_R$=8.917, to provide the enantiomer. 400 MHz ¹H NMR (CD₃OD) δ 7.98 (s, 1H), 7.38-7.33 (m, 2H), 7.33-7.29 (m, 2H), 7.26-7.22 (m, 1H), 5.07-5.02 (m, 1H), 3.77-3.64 (m, 2H), 3.12-3.07 (m, 1H), 2.99-2.91 (m, 3H), 2.67-2.63 (m, 1H), 2.29-2.25 (m, 1H), 1.48(d, J=6.6 Hz, 6H), 1.14 (d, J=6.6 Hz, 3H). MS: (M+H m/z 352.1).

Example 32

(a) 1-isopropyl-6-[(3,4-trans)-4-methylpyrrolidin-3-yl]-1H-pyrazolo[3,4-d]pyrimidin-4(5H)-one

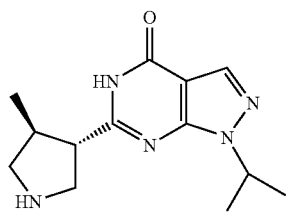

Following the procedure for the preparation of 1-cyclopentyl-6-[(3S,4S)-4-methylpyrrolidin-3-yl]-1H-pyrazolo[3,4-d]pyrimidin-4(5H)-one but substituting the 6-[(3,4-trans)-1-benzyl-4-methylpyrrolidin-3-yl]-1-isopropyl-1,5-dihydro-4H-pyrazolo[3,4-d]pyrimidin-4-one provided the title compound. 400 MHz ¹H NMR (CD₃OD) δ 8.02 (s, 1H), 5.11-5.08 (m, 1H), 3.80-3.74 (m, 2H), 3.64-3.57 (m, 1H), 3.30-3.22 (m, 1H), 3.07-3.02 (m, 1H), 2.75-2.71 (m, 1H), 1.49 (dd, J=6.6, 1.7 Hz, 6H), 1.15 (d, J=7.1 Hz, 3H). MS: (M⁺H m/z=262.2)

(b) 1-isopropyl-6-[(3,4-trans)-4-methyl-1-(quinolin-2-ylmethyl)pyrrolidin-3-yl]-1,5-dihydro-4H-pyrazolo[3,4-d]pyrimidin-4-one

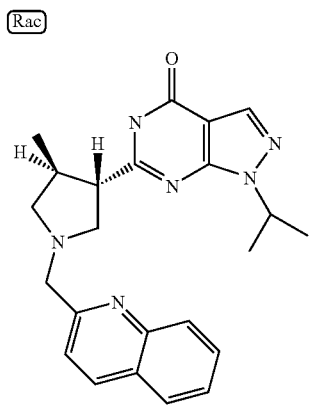

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3,4-trans)-4-methylpyrrolidin-3-yl]-1H-pyrazolo[3,4-d]pyrimidin-4(5H)-one and quinoline-2-carbaldehyde provided the title compound. 400 MHz ¹H NMR (CD₃OD) δ 8.31 (d, J=8.7 Hz, 1H), 8.02 (d, J=8.7 Hz, 1H), 7.98 (s, 1H), 7.95 (d, J=7.9 Hz, 1H), 7.75-7.68 (m, 2H), 7.58-7.54 (m, 1H), 5.07-5.04 (m, 1H), 4.11-3.96 (m, 2H), 3.22-3.18 (m, 1H), 3.14-3.11 (m, 1H), 3.05-2.96 (m, 2H), 2.71-2.68 (m, 1H), 2.42-2.37 (m, 1H), 1.49 (q, J=6.6 Hz, 6H), 1.17 (d, J=7.1 Hz, 3H). MS: (M⁺H m/z 403.1).

Example 33

1-isopropyl-6-[(3,4-trans)-4-methyl-1-(quinoxalin-6-ylmethyl)pyrrolidin-3-yl]-1,5-dihydro-4H-pyrazolo[3,4-d]pyrimidin-4-one

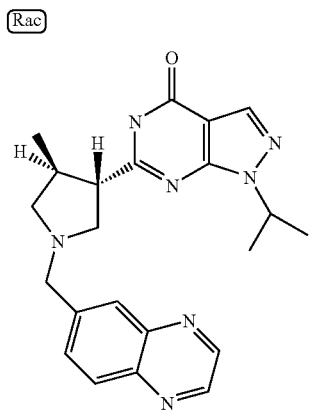

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3,4-trans)-4-methylpyrrolidin-3-yl]-1H-pyrazolo[3,4-d]pyrimidin-4(5H)-one and quinoxaline-6-carbaldehyde provided the title compound. 400

MHz ¹H NMR (CD₃OD) δ 8.84-8.81 (m, 2H), 8.04-8.00 (m, 2H), 7.96 (s, 1H), 7.91-7.88 (m, 1H), 5.09-5.02 (m, 1H), 4.01-3.87 (m, 2H), 3.14-3.93 (m, 4H), 2.72-2.66 (m, 1H), 2.39-2.34 (m, 1H), 1.47 (dd, J=6.6, 1.2 Hz, 6H), 1.15 (d, J=6.6 Hz, 3H). MS: (M+H m/z 404.1).

Example 34

1-isopropyl-6-[(3,4-trans)-4-methyl-1-(quinolin-3-ylmethyl)pyrrolidin-3-yl]-1,5-dihydro-4H-pyrazolo[3,4-d]pyrimidin-4-one

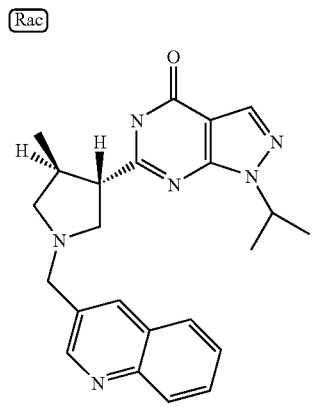

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3,4-trans)-4-methylpyrrolidin-3-yl]-1H-pyrazolo[3,4-d]pyrimidin-4(5H)-one and quinoline-3-carbaldehyde provided the title compound. 400 MHz ¹H NMR (CD₃OD) δ 8.87 (d, J=2.1 Hz, 1H), 8.30 (d, J=1.2 Hz, 1H), 7.99 (d, J=8.7 Hz, 1H), 7.97 (s, 1H), 7.90 (d, J=7.5 Hz, 1H), 7.74-7.69 (m, 1H), 7.60-7.56 (m, 1H), 5.06-4.99 (m, 1H), 3.97-3.87 (m, 2H), 3.13-3.09 (m, 1H), 3.05-3.02 (m, 2H), 2.97-2.93 (m, 1H), 2.73-2.66 (m, 1H), 2.39-2.35 (m, 1H), 1.46 (dd, J=6.6, 2.3 Hz, 6H), 1.15 (d, J=7.1 Hz, 3H). MS: (M+H m/z 403.1).

Example 35

(a) (3,4-trans)-ethyl-1-benzyl-4-(trifluoromethyl)pyrrolidine-3-carboxylate

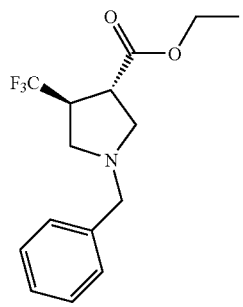

Following the procedure for the preparation of (3,4-trans)-methyl 1-benzyl-4-methylpyrrolidine-3-carboxylate but substituting (E)-methyl 4,4,4-trifluorobut-2-enoate provided the title compound. 400 MHz ¹H NMR (CDCl₃) δ 7.33-7.22 (m, 5H), 4.16 (q, J=7.1 Hz, 2H), 3.65-3.56 (m, 2H), 3.40-3.32 (m, 1H), 3.12-3.07 (m, 1H), 2.90-2.76 (m, 3H), 2.70-2.66 (m, 1H), 1.24 (t, J=7.1 Hz, 3H). MS: (M⁺H m/z=302.1).

(b) 6-[(3,4-trans)-1-benzyl-4-(trifluoromethyl)pyrrolidin-3-yl]-1-cyclopentyl-1,5-dihydro-4H-pyrazolo[3,4-d]pyrimidin-4-one

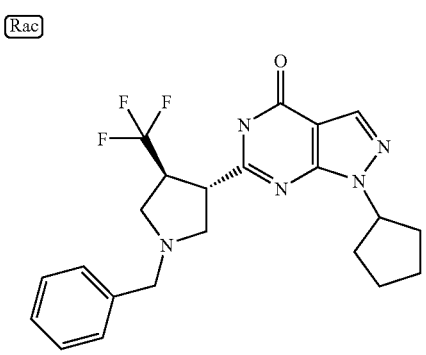

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide and (3,4-trans)-methyl 1-benzyl-4-(trifluoromethyl)pyrrolidine-3-carboxylate provided the title compound. 400 MHz ¹H NMR (CDCl₃) δ 8.02 (s, 1H), 7.38-7.26 (m, 5H), 5.15-5.11 (m, 1H), 3.83 (d, J=12.5 Hz, 1H), 3.64 (d, J=12.5 Hz, 1H), 3.44-3.41 (m, 1H), 3.34 (t, J=9.1 Hz, 1H), 3.12-3.10 (m, 1H), 3.03 (d, J=9.9 Hz, 1H), 2.70-2.65 (m, 1H), 2.55-5.50 (m, 1H), 2.11-1.93 (m, 4H), 1.72-1.66 (m, 2H), 0.86-0.83 (m, 2H). MS: (M⁺H m/z=432.0).

Example 36

(a) 1-isopropyl-6-[(3S,4S)-4-methylpyrrolidin-3-yl]-1H-pyrazolo[3,4-d]pyrimidin-4(5H) one

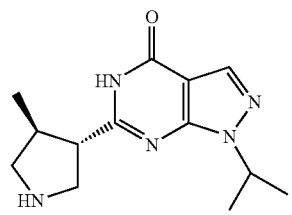

Following the procedure for the preparation of 1-cyclopentyl-6-[(3S,4S)-4-methylpyrrolidin-3-yl]-1H-pyrazolo[3,4-d]pyrimidin-4(5H)-one but substituting the 6-[(3S,4S)-1-benzyl-4-methylpyrrolidin-3-yl]-1-isopropyl-1,5-dihydro-4H-pyrazolo[3,4-d]pyrimidin-4-one provided the title compound. 400 MHz ¹H NMR (CD₃OD) δ 8.02 (s, 1H), 5.11-5.08 (m, 1H), 3.80-3.74 (m, 2H), 3.64-3.57 (m, 1H), 3.30-3.22 (m, 1H), 3.07-3.02 (m, 1H), 2.75-2.71 (m, 1H), 1.49 (dd, J=6.6, 1.7 Hz, 6H), 1.15 (d, J=7.1 Hz, 3H). MS: (M+H m/z=262.2).

(b) 1-isopropyl-6-[(3S,4S)-4-methyl-1-(quinoxalin-6-ylmethyl)pyrrolidin-3-yl]-1,5-dihydro-4H-pyrazolo[3,4-d]pyrimidin-4-one

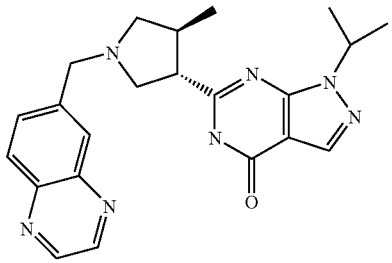

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and quinoxaline-6-carbaldehyde provided the title compound. 400 MHz $^1$H NMR (CD$_3$OD) δ 11.0 (brs, 1H), 8.81 (s, 2H), 8.13 (d, J=8.7, 1H), 8.01-7.92 (m, 3H), 5.01-4.94 (m, 1H), 4.01-3.88 (m, 2H), 3.37 (t, J=8.3, 1H), 3.05 (d, J=9.9, 1H), 2.86-2.85 (m, 1H), 2.70-2.68 (m, 1H), 2.49-2.44 (m, 1H), 2.07-2.01 (m, 1H). 1.48 (dd, J=15.3, 6.6 Hz, 6H), 1.20 (d, J=7.05 Hz, 3H). MS: (M+H m/z 404.1).

Example 37

1-isopropyl-6-[(3S,4S)-4-methyl-1-(quinolin-3-ylmethyl)pyrrolidin-3-yl]-1,5-dihydro-4H-pyrazolo[3,4-d]pyrimidin-4-one

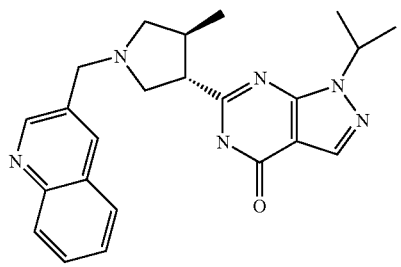

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and quinoline-3-carbaldehyde provided the title compound. 400 MHz $^1$H NMR (CD$_3$OD) δ 11.0 (brs, 1H), 8.87 (d, J=2.1 Hz, 1H), 8.29 (s, 1H), 8.07 (d, J=8.3 Hz, 1H), 8.02 (s, 1H), 7.90-7.88 (m, 1H), 7.70-7.66 (m, 1H), 7.56-7.51 (m, 1H), 5.01-4.92 (m, 1H), 4.03-3.83 (m, 2H), 3.40 (t, J=8.7 Hz, 1H), 3.07 (d, J=9.5 Hz, 1H), 2.89-2.86 (m, 1H), 2.68-2.67 (m, 1H), 2.48-2.47 (m, 1H), 2.08-2.02 (m, 1H), 1.48 (dd, J=6.6, 16.59 Hz, 6H), 1.20 (J=7.1 Hz, 3H). MS: (M+H m/z 403.1).

Example 38

1-cyclopentyl-6-{(3S,4S)-4-methyl-1-[(5-methylpyrazin-2-yl)methyl]pyrrolidin-3-yl}-1,5-dihydro-4H-pyrazolo[3,4-d]pyrimidin-4-one

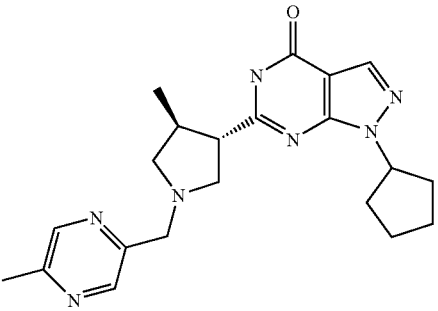

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and 5-methylpyrazine-2-carbaldehyde provided the title compound. 400 MHz $^1$H NMR (CDCl$_3$) δ 8.53 (s, 1H), 8.53 (s, 1H), 8.01 (s, 1H), 5.16-5.05 (m, 1H), 4.02 (d, J=14.1 Hz, 1H), 3.74 (d, J=14.1 Hz, 1H), 3.45-3.41 (m, 1H), 3.38 (t, J=8.3 Hz, 1 Hz, 1H), 3.08 (d, J=9.9 Hz, 1H), 2.84-2.83 (m, 1H), 2.62-2.54 (m, 1H), 2.52 (s, 3H), 2.47-2.40 (m, 1H), 2.14-1.89 (m, 6H), 1.71-1.64 (m, 2H), 1.24-1.16 (m, 3H). MS: (M+H m/z=394.1).

Example 39

6-[(3,4-trans)-1-benzyl-4-ethylpyrrolidin-3-yl]-1-isopropyl-1,5-dihydro-4H-pyrazolo[3,4-d]pyrimidin-4-one

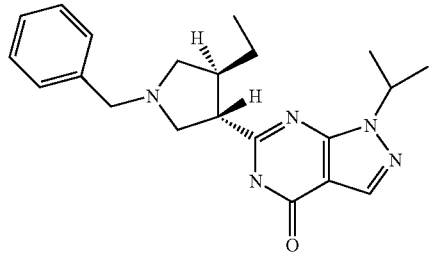

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-isopropyl-1H-pyrazole-4-carboxamideand (3,4-trans)-methyl 1-benzyl-4-ethylpyrrolidine-3- carboxylate provided the title compound. 400 MHz $^1$H NMR (CD$_3$OD) δ 8.01 (s, 1H), 7.38-7.22 (m, 5H), 5.06-5.01 (m, 1H), 3.76-3.64 (m, 2H), 3.12 (t, J=8.71 Hz, 1H), 3.00-2.91 (m, 2H), 2.87-2.82 (m, 1H), 2.51-2.47 (m, 1H), 2.30-2.26 (m, 1H), 1.60-1.50 (m, 2H), 1.49 (d, J=7.05 Hz, 6H), 3.08 (d, J=7.5 Hz, 3H). MS: (M$^+$H m/z=366.1).

Example 40

6-[(3S,4S)-1-benzyl-4-ethylpyrrolidin-3-yl]-1-isopropyl-1,5-dihydro-4H-pyrazolo[3,4-d]pyrimidin-4-one

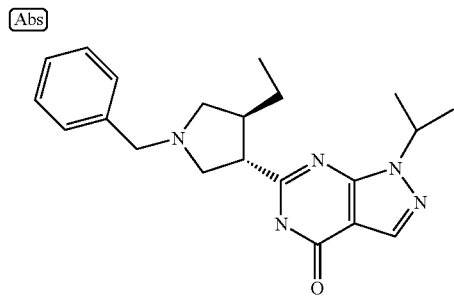

The racemate was separated on Chiralcel OJ chiral HPLC column, Mobile Phase 80/20 Heptane/EtOH, T$_R$=9.177, to provide the enantiomer. 400 MHz $^1$H NMR (CD$_3$OD) δ 8.01 (s, 1H), 7.38-7.22 (m, 5H), 5.06-5.01 (m, 1H), 3.76-3.64 (m, 2H), 3.12 (t, J=8.71 Hz, 1H), 3.00-2.91 (m, 2H), 2.87-2.82 (m, 1H), 2.51-2.47 (m, 1H), 2.30-2.26 (m, 1H), 1.60-1.50 (m, 2H), 1.49 (d, J=7.05 Hz, 6H), 3.08 (d, J=7.5 Hz, 3H). MS: (M$^+$H m/z=366.2).

Example 41

1-isopropyl-6-{(3S,4S)-4-methyl-1-[(2-methylpyrimidin-5-yl)methyl]pyrrolidin-3-yl}-1,5-dihydro-4H-pyrazolo[3,4-d]pyrimidin-4-one

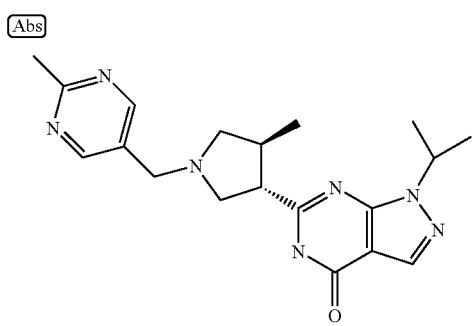

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-]pyrimidin-4(5H)-one and 2-methylpyrimidine-5carbaldehyde provided the title compound. 400 MHz $^1$H NMR (CD$_3$OD) δ 8.68 (s, 2H), 7.97 (s, 1H), 5.08-5.01 (m, 1H), 3.78-3.68 (m, 2H), 3.08-2.92 (m, 4H), 2.74-2.67 (m, 1H), 2.65 (s, 3H), 2.36-2.32 (m, 1H), 1.48 (d, J=6.6 Hz, 6H), 1.15 (d, J=7.1 Hz, 3H). MS: (M$^+$H m/z=368.1).

Example 42

6-(1-benzylpyrrolidin-3-yl)-1-cyclopentyl-1,5-dihydro-4H-pyrazolo[3,4-d]pyrimidin-4-one

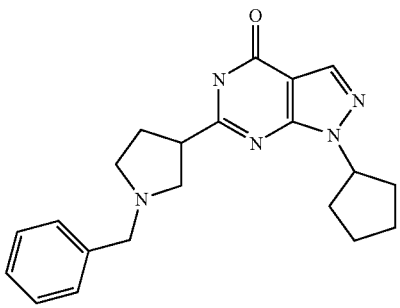

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide and methyl 1-benzylpyrrolidine-3-carboxylate provided the title compound. 400 MHz $^1$H NMR (CDCl$_3$) δ 8.01 (s, 1H), 7.39-7.32 (m, 4H), 7.27-7.23 (m, 1H), 5.12-5.09 (m, 1H), 3.84 (d, J=12.4 Hz, 1H), 3.61 (d, J=12.4 Hz, 1H), 3.30-3.26 (m, 1H), 3.18-3.14 (m, 1H), 3.01 (d, J=9.9 Hz, 1H), 2.45-2.32 (m, 3H), 2.11-1.90 (m, 7H), 1.71-1.65 (m, 2H). MS: (M$^+$H m/z=364.1).

Example 43

1-isopropyl-6-{(3S,4S)-1-[(6-methoxypyridin-3-yl)methyl]-4-methylpyrrolidin-3-yl}1,5-dihydro-4H-pyrazolo[3,4-d]pyrimidin-4-one

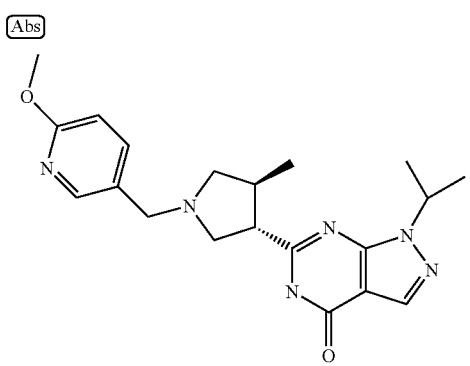

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and 6-methoxynicotinaldehyde provided the title compound. 400 MHz $^1$H NMR (CDCl$_3$) δ 8.02 (s, 2H), 7.72 (m, 1H), 6.77 (d, J=8.3 Hz, 1H), 3.90 (s, 3H), 3.73-3.53 (m, 2H), 3.39-3.33 (m, 1H), 3.30 (m, 1H), 2.8 (m, 1H), 2.55-2.40 (m, 1H), 1.9 (m, 1H), 1.57-1.53 (m, 2H), 1.52-1.47 (m, 6H), 1.19 (d, J=6.6 Hz, 3H). MS: (M+H m/z=383.2).

Example 44

(a) 6-((3,4-trans)-4-ethylpyrrolidin-3-yl)-1-isopropyl-1H-pyrazolo[3,4-d]pyrimidin-4(5H)-one

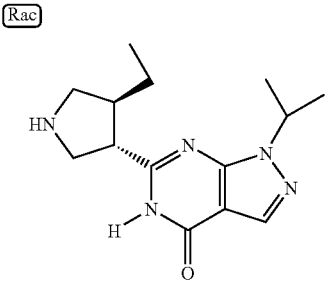

Following the procedure for the preparation of 1-cyclopentyl-6-[(3S,4S)-4-methylpyrrolidin-3-yl]-1H-pyrazolo[3,4-d]pyrimidin-4(5H)-one but substituting the 6-[(3,4-trans)-1-benzyl-4-ethylpyrrolidin-3-yl]-1-isopropyl-1,5-dihydro-4H-pyrazolo[3,4-d]pyrimidin-4-one provided the title compound. 400 MHz $^1$H NMR (CD$_3$OD) δ 8.02 (s, 1H), 5.10 (m, 1H), 3.78-3.60 (m, 3H), 3.32-3.28 (m, 1H), 3.10 (m, 1H), 2.62 (m, 1H), 1.65 (m, 1), 1.58 (m, 1H), 1.49 (dd, J=6.6, 1.7 Hz, 6H), 0.97 (t, J=7.5 Hz, 3H). MS: (M+H m/z=276.1).

(b) 6-[(3,4-trans)-4-ethyl-1-(quinolin-3-ylmethyl)pyrrolidin-3-yl]-1-isopropyl-1,5-dihydro-4-H-pyrazolo[3,4-d]pyrimidin-4-one

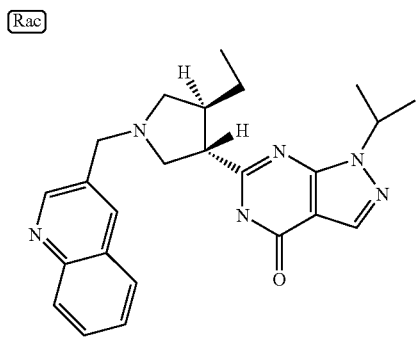

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 6-((3,4-trans)-4-ethylpyrrolidin-3-yl)-1-isopropyl-1H-pyrazolo[3,4-d]pyrimidin-4(5H)-one and quinoline-3-carbaldehyde provided the title compound. 400 MHz $^1$H NMR (CD$_3$OD) δ 8.86 (d, J=2.1 Hz, 1H), 8.29 (d, J=1.7 Hz, 1H), 7.98 (d, J=8.3 Hz, 1H), 7.97 (s, 1H), 7.89 (d, J=8.3 Hz, 1H), 7.73-7.68 (m, 1H), 7.59-7.55 (m, 1H), 5.05-4.98 (m, 1H), 3.94-3.85 (m, 2H), 3.13-3.09 (m, 1H), 3.02-2.94 (m, 3H), 2.57-2.52 (m, 1H), 2.39-2.34 (m, 1H), 1.58-1.48 (m, 2H), 1.48 (d, J=6.6 Hz, 6H) 10.87 (t, J=7.05 Hz, 3H). MS: (M+H m/z=417.0).

Example 45

6-{(3,4-trans)-4-ethyl-1-[(6-methoxypyridin-3-yl)methyl]pyrrolidin-3-yl}-1-isopropyl-1,5-dihydro-4H-pyrazolo[3,4-d]pyrimidin-4-one

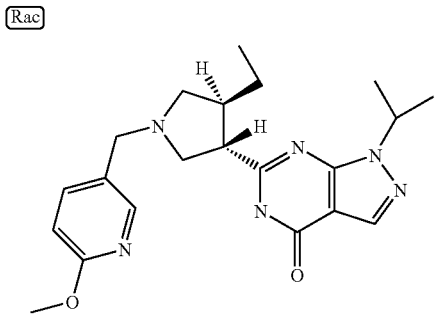

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 6-((3,4-trans)-4-ethylpyrrolidin-3-yl)-1-isopropyl-1H-pyrazolo[3,4-d]pyrimidin-4(5H)-one and 6-methoxynicotinaldehyde provided the title compound. 400 MHz $^1$H NMR (CDCl$_3$) δ 10.83 (brs, 1H), 8.02 (d, J=2.1 Hz, 1H), 8.00 (s, 1H), 7.69 (dd, J=8.7, 2.1 Hz, 1H), 6.77 (d, J=8.3 Hz, 1H), 4.98-4.94 (m, 1H), 3.89 (s, 3H), 3.69-3.54 (m, 2H), 3.29 (t, J=8.5 Hz, 1H), 2.98 (d, J=9.9 Hz, 1H), 2.88-2.87 (m, 1H), 2.55 (m, 1H), 2.18 (m, 1H), 1.91 (m, 1H), 1.60-1.55 (m, 1H), 1.51-1.47 (m, 7H), 0.91 (t, J=7.5 Hz, 3H). MS: (M+H m/z=397.0).

Example 46

6-[(3,4-trans)-4-ethyl-1-(quinoxalin-6-ylmethyl)pyrrolidin-3-yl]-1-isopropyl-1,5-dihydro-4H-pyrazolo[3,4-d]pyrimidin-4-one

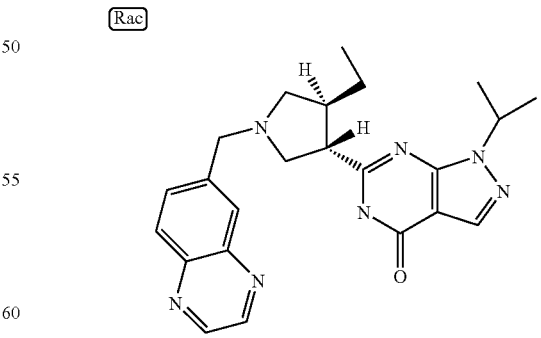

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 6-((3,4-trans)-4-ethylpyrrolidin-3-yl)-1-isopropyl-1H-pyrazolo[3,4-d]pyrimidin-4(5H)-one and quinoxaline-6-carbaldehyde provided the title compound. 400 MHz ¹H NMR (CDCl₃) δ 10.83 (brs, 1H), 8.81 (s, 2H), 7.79 (d, J=2.5 Hz, 1H), 8.15-7.92 (m, 3H), 4.99-4.92 (m, 1H), 3.98-3.86 (m, 2H), 3.35 (t, J=8.7 Hz, 1H), 3.04 (d, J=9.9 Hz, 1H), 2.92-2.91 (m, 1H), 2.61-2.57 (m, 1H), 2.25-2.2 (m, 1H), 2.02 (t, J=8.7 Hz, 1H), 1.64-1.52 (m, 1H), 1.50-1.45 (m, 7H), 0.91 (t, J=7.5 Hz, 3H). MS: (M⁺H m/z=418.1).

Example 47

1-cyclopentyl-6-{(3S,4S)-1-[(1,3-dimethyl-1H-pyrazolo-5-yl)methyl]-4-methylpyrrolidin-3-yl}-1,5-dihydro-4H-pyrazolo[3,4-d]pyrimidin-4-one

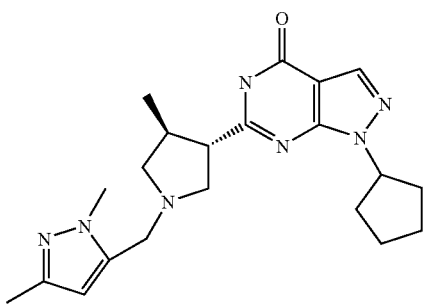

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and 1,3-dimethyl-1H-pyrazole-5-carbaldehyde provided the title compound. 400 MHz ¹H NMR (CDCl₃) δ 7.99 (s, 1H), 5.95-5.94 (m, 1H), 5.14-5.09 (m, 1H), 3.87 (s, 3H), 3.81 (s, 1H), 3.66 (q, J=14.5 Hz, 2H), 3.33 (t, J=8.3 Hz, 1H), 3.03 (d, J=9.9 Hz, 1H), 2.84-2.82 (m, 1H), 2.59-2.55 (m, 1H), 2.44-2.41 (m, 1H), 2.20-2.19 (m, 3H), 2.12-1.90 (m, 5H), 1.70-1.65 (m, 2H), 1.25-1.18 (m, 3H). MS: (M⁻H m/z=396.1).

Example 48

1-cyclopentyl-6-[(3S,4S)-4-methyl-1-(4,5,6,7-tetrahydropyrazolo[1,5-a]pyridin-3-ylmethyl)pyrrolidin-3-yl]-1,5-dihydro-4H-pyrazolo[3,4-d]pyrimidin-4-one

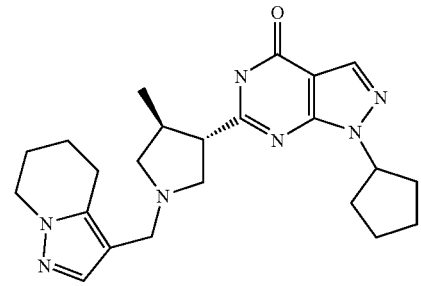

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and 4,5,6,7-tetrahydropyrazolo[1,5-a]pyridine-3-carbaldehyde provided the title compound. 400 MHz ¹H NMR (CDCl₃) δ 7.99 (s, 1H), 7.35 (s, 1H), 5.16-5.09 (m, 1H), 4.11-4.06 (m, 2H), 3.68 (d, J=13.3 Hz, 1H), 3.57 (d, J=13.3 Hz, 1H), 3.32 (t, J=8.7 Hz, 1H), 3.00 (d, J=9.9 Hz, 1H), 2.94-2.80 (m, 2H), 2.78-2.77 (m, 1H), 2.49-2.45 (m, 1H), 2.38-2.33 (m, 1H), 2.11-1.83 (m, 11H), 1.73-1.61 (m, 2H), 1.17 (d, J=7.1 Hz, 3H). MS: (M⁺H m/z=422.1).

Example 49

1-cyclopentyl-6-{(3S,4S)-4-methyl-1-[(1-methyl-1H-benzimidazol-2-yl)methyl]pyrrolidin-3-yl}-1,5-dihydro-4H-pyrazolo[3,4-d]pyrimidin-4-one

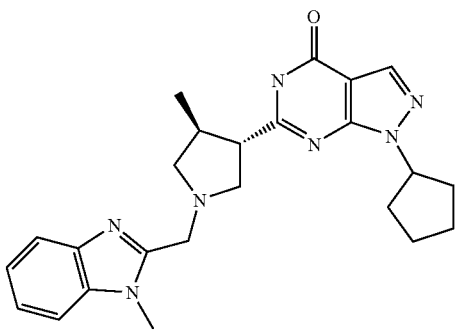

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and 1-methyl-1H-benzo[d]imidazole-2-carbaldehyde provided the title compound. 400 MHz ¹H NMR (CDCl₃) δ 7.98 (s, 1H), 7.73 (m, 1H), 7.35 (dd, J=7.1, 1.2 Hz, 1H), 7.29-7.21 (m, 2H), 5.13-5.09 (m, 1H), 4.11-4.06 (m, 2H), 3.97 (s, 3H), 3.37 (t, J=8.3 Hz, 1H), 3.06 (d, J=10.4 Hz, 1H), 2.88-2.85 (m, 1H), 2.77-2.73 (m, 1H), 2.16-1.92 (m, 8H), 1.70-1.66 (m, 2H), 1.21 (d, J=7.1 Hz, 3H). MS: (M⁺H m/z=432.1).

Example 50

1-isopropyl-6-{(3S,4S)-4-methyl-1-[(5methylpyrazin-2-yl)methyl]pyrrolidin-3-yl}-1,5-dihydro-4H-pyrazolo[3,4-d]pyrimidin-4-one

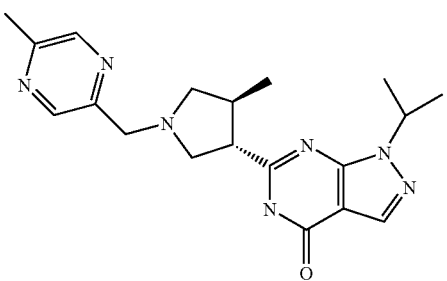

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and 5-methylpyrazine-2-carbaldehyde provided the title compound. 400 MHz $^1$H NMR (CDCl$_3$) δ 11.4 (brs, 1H), 8.49 (s, 1H), 8.44 (s, 1H), 7.99 (s, 1H), 5.00-4.93 (m, 1H), 4.00-3.97 (m, 1H), 3.78-3.67 (m, 1H), 3.33 (t, J=8.3 Hz, 1H), 3.04 (d, J=9.9 Hz, 1H), 2.85-2.82 (m, 1H), 2.65-2.61 (m, 1H), 2.49 (s, 3H), 2.48-2.41 (m, 1H), 2.13 (t, J=8.5 Hz, 1H), 1.46 (dd, J=11.6, 6.6 Hz, 6H), 1.17 (d, J=7.05 Hz, 3H). MS: (M+H m/z=368.1).

Example 51

6-[(3S,4S)-1-(cinnolin-3-ylmethyl)-4-methylpyrrolidin-3-yl]-1-cyclopentyl-1,5-dihydro-4H-pyrazolo[3,4-d]pyrimidin-4-one

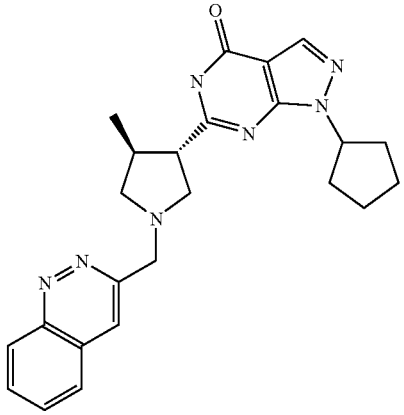

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and cinnoline-3-carbaldehyde provided the title compound. 400 MHz $^1$H NMR (CDCl$_3$) δ 8.49 (d, J=8.7 Hz, 1H), 8.16 (s, 1H), 8.01 (s, 1H), 7.93 (d, J=7.9 Hz, 1H), 7.83-7.81 (m, 1H), 7.79-7.71 (m, 1H), 5.16-5.09 (m, 1H), 4.47-4.44 (m, 1H), 4.35-4.32 (m, 1H), 3.49-3.45 (m, 2H), 3.10-3.07 (m, 1H), 2.87-2.71 (m, 2H), 2.49-2.48 (m, 1H), 2.23 (m, 1H), 2.11-1.87 (m, 5H), 1.73-1.63 (m, 2H), 1.22 (d, J=7.1 Hz, 3H). MS: (M+H m/z=430.1).

Example 52

(a) 1-cyclopentyl-6-[(3,4-trans)-4-(trifluoromethyl)pyrrolidin-3-yl]-1H-pyrazolo[3,4-d]pyrimidin-4(5H)-one

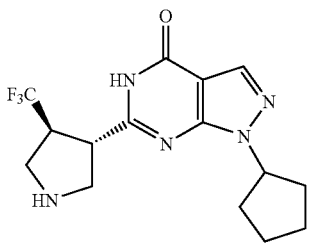

Following the procedure for the preparation of 1-cyclopentyl-6-[(3S,4S)-4-methylpyrrolidin-3-yl]-1H-pyrazolo[3,4-d]pyrimidin-4(5H)-one but substituting the 6-[(3,4-trans)-1-benzyl-4-(trifluoromethyl)pyrrolidin-3-yl]-1-cyclopentyl-1,5-dihydro-4H-pyrazolo[3,4-d]pyrimidin-4-one provided the title compound. 400 MHz $^1$H NMR (CD$_3$OD) δ 7.98 (s, 1H), 5.23 (m, 1H), 3.73 (m, 1H), 3.42 (m, 2H), 3.10 (m, 2H), 2.19-1.92 (m, 7H), 1.75 (m, 2H), 1.23-1.19 (m, 3H).

(b) 1-cyclopentyl-6-[(3,4-trans)-1-(quinoxalin-6-ylmethyl)-4-(trifluoromethyl)pyrrolidin-3-yl]-1,5-dihydro-4H-pyrazolo[3,4-d]pyrimidin-4-one

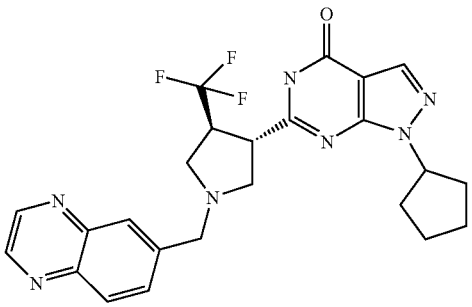

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3,4-trans)-4-(trifluoromethyl)pyrrolidin-3-yl]-1H-pyrazolo[3,4-d]pyrimidin-4(5H)-one and quinoxaline-6-carbaldehyde provided the title compound. 400 MHz $^1$H NMR (CDCl$_3$) δ 8.80 (s, 1H), 8.08 (d, J=8.3 Hz, 1H), 7.99 (m, 1H), 7.86-7.83 (m, 1H), 5.13-5.10 (m, 1H), 4.88 (s, 1H), 3.96-3.88 (m, 2H), 3.50-3.35 (m, 2H), 3.17 (t, J=9.9 Hz, 1H), 3.03-2.99 (m, 1H), 2.92-2.88 (m, 1H), 2.79-2.75 (m, 1H), 2.11-1.90 (m, 6H), 1.71-1.65 (m, 1H).

Example 53

1-cyclopentyl-6-{(3S,4S)-4-methyl-1-[(2-methylpyrimidin-4-yl)methyl]pyrrolidin-3-yl}-1,5-dihydro-4H-pyrazolo[3,4-d]pyrimidin-4-one

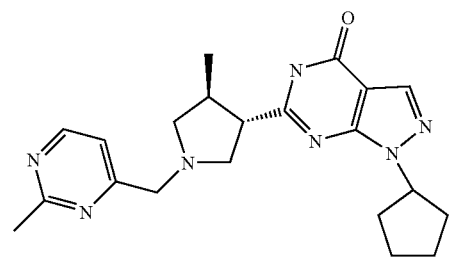

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and 2-methylpyrimidine-4-carbaldehyde provided the title compound. 400 MHz $^1$H NMR (CDCl$_3$) δ 8.60 (d, J=5.4 Hz, 1H), 8.03 (s, 1H), 7.24 (s, 1H), 5.18-5.10 (m, 1H), 3.97-3.94 (m, 1H), 3.72-3.68 (m, 1H), 3.40 (t, J=8.3 Hz, 1H), 3.15 (d, J=9.5

Hz, 1H), 2.89 (m, 1H), 2.73 (s, 3H), 2.68-2.63 (m, 1H), 2.53-2.47 (m, 1H), 2.15-1.89 (m, 7H), 1.74-1.65 (m, 2H), 1.21 (d, J=7.1 Hz, 3H). MS: (M+H m/z=394.1).

Example 54

1-cyclopentyl-6-[(3S,4S)-1-{[2-(dimethylamino)pyrimidin-4-yl]methyl}-4-methylpyrrolidin-3-yl]-1,5-dihydro-4H-pyrazolo[3,4-d]pyrimidin-4-one

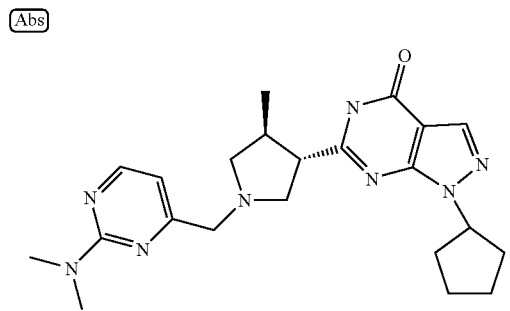

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-cyclopentyl-6-[(3S,4S)-4-methylpyrrolidin-3-yl]-1H-pyrazolo[3,4-d]pyrimidin-4(5H)-one and 2-(dimethylamino)pyrimidine-4-carbaldehyde provided the title compound. 400 MHz $^1$H NMR (CDCl$_3$) δ 8.24-8.21 (m, 1H), 8.00-7.99 (m, 1H), 6.52-6.50 (m, 1H), 5.13-5.10 (m, 1H), 3.72-3.68 (m, 1H), 3.56-3.52 (m, 1H), 3.46-3.40 (m, 3H), 3.17-3.11 (m, 7H), 2.84-2.82 (m, 1H), 2.64-2.60 (m, 1H), 2.44-2.38 (m, 1H), 2.06-1.92 (m, 5H), 1.66-1.65 (m, 2H), 1.20-1.16 (m, 3H). MS: (M+H m/z=423.1).

Example 55

(a) 1-cyclopentyl-6-[(3,4-trans)-4-cylopropylpyrrolidin-3-yl]-1H-pyrazolo[3,4-d]pyrimidin-4(5H)-one

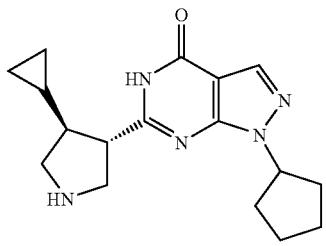

Following the procedure for the preparation of 1-cyclopentyl-6-[(3S,4S)-4-methylpyrrolidin-3-yl]-1H-pyrazolo[3,4-d]pyrimidin-4(5H)-one but substituting 6-[(3,4-trans)-1-benzyl-4-cyclopropylpyrrolidin-3-yl]-1-cyclopentyl-1,5-dihydro-4H-pyrazolo[3,4-d]pyrimidin-4-one provided the title compound. 400 MHz $^1$H NMR (CDCl$_3$) δ 8.08-7.94 (m, 1 H), 5.17-5.10 (m, 1H), 3.39-3.34 (m, 1H), 3.29-3.28 (m, 2H), 3.17-3.14 (m, 1H), 2.13-1.91 (m, 7H), 1.78-1.67 (m, 3H), 0.82 (m, 1H), 0.47-0.44 (m, 2H), 0.13-0.08 (m, 2H). MS: (M+H m/z=314.2).

(b) 1-cyclopentyl-6-{(3,4-trans)-4-cyclopropyl-1-[(5-methylpyrazin-2-yl)methyl]pyrrolidin-3-yl}-1,5-dihydro-4H-pyrazolo[3,4-d]pyrimidin-4-one

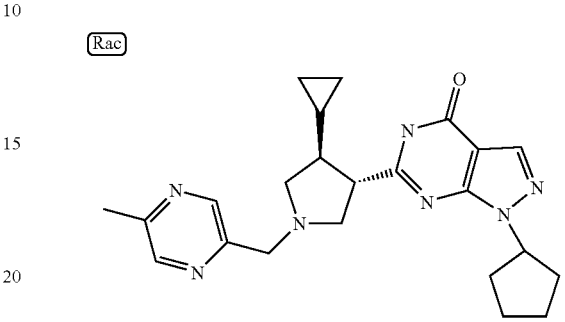

Following the procedure for the preparation of 1-cyclopentyl-6-[(3S,4S)-4-methylpyrrolidin-3-yl]-1H-pyrazolo[3,4-d]pyrimidin-4(5H)-one but substituting 1-cyclopentyl-6-[(3,4-trans)-4-cyclopropylpyrrolidin-3-yl]-1H-pyrazolo[3,4-d]pyrimidin-4(5H)-one and 5-methylpyrazine-2-carbaldehyde provided the title compound. 400 MHz $^1$H NMR (CDCl$_3$) δ 8.52 (d, J=0.8 Hz, 1H), 8.46 (s, 1H), 8.00 (s, 1H), 5.14-5.10 (m, 1H), 4.04-4.01 (m, 1H), 3.78-3.75 (m, 1H), 3.35 (t, J=8.7 Hz, 1H), 3.15-3.09 (m, 2H), 2.66-2.64 (m, 1H), 2.52 (s, 3H), 2.38 (t, J=8.7 Hz, 1H), 2.11-2.01 (m, 3H), 1.96-1.91 (m, 2H), 1.73-1.65 (m, 2H), 1.24-1.20 (m, 1H), 0.59-0.83 (m, 2H), 0.53-0.49 (m, 2H), 0.23-0.11 (m, 2H). MS: (M+H m/z=420.1).

Example 56

1-cyclopentyl-6-[(3,4-trans)-4-cyclopropyl-1-(quinoxalin-6-ylmethyl)pyrrolidin-3-yl]-1,5-dihydro-4H-pyrazolo[3,4-d]pyrimidin-4-one

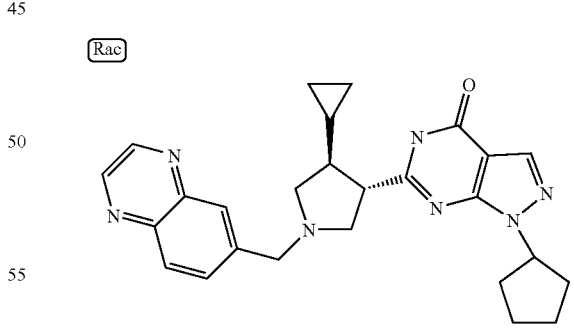

Following the procedure for the preparation of 1-cyclopentyl-6-[(3S,4S)-4-methylpyrrolidin-3-yl]-1H-pyrazolo[3,4-d]pyrimidin-4(5H)-one but substituting 1-cyclopentyl-6-[(3,4-trans)-4-cyclopropylpyrrolidin-3-yl]-1H-pyrazolo[3,4-d]pyrimidin-4(5H)-one and quinoxaline-6-carbaldehyde provided the title compound. 400 MHz $^1$H NMR (CDCl$_3$) δ 8.82 (s, 2H), 8.14 (d, J=8.7 Hz, 1H), 8.00 (s, 2H), 7.96-7.94 (m, 1H), 5.16-5.09 (m, 1H), 3.98-3.95 (m, 2H), 3.35 (t, J=8.3 Hz, 1H), 3.15-3.08 (m, 2H), 2.70 (m, 1H), 2.27 (m, 1H), 2.15-1.88 (m, 6H), 1.74-1.62 (m, 3H), 0.91-0.87 (m, 1H), 0.55-0.47 (m, 2H), 0.21-0.09 (m, 2H). MS: (M+H m/z=456.1).

Example 57

1-cyclopentyl-6-[(3,4-trans)-4-cyclopropyl-1-methylpyrrolidin-3-yl]-1,5-dihydro-4H-pyrazolo[3,4-d]pyrimidin-4-one

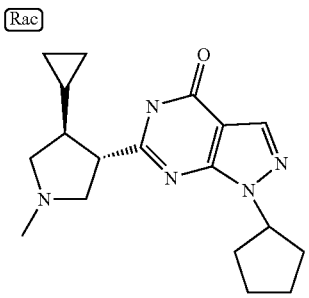

Following the procedure for the preparation of 1-cyclopentyl-6-[(3S,4S)-4-methylpyrrolidin-3-yl]-1H-pyrazolo[3,4-d]pyrimidin-4(5H)-one but substituting 1-cyclopentyl-6-[(3,4-trans)-4-cyclopropylpyrrolidin-3-yl]-1H-pyrazolo[3,4-d]pyrimidin-4(5H)-one and formaldehyde provided the tide compound. 400 MHz $^1$H NMR (CDCl$_3$) δ 8.01 (s, 1H), 5.19-5.11 (m, 1H), 3.31 (d, J=8.7 Hz, 1H), 3.14-3.13 (m, 1H), 3.06 (d, J=9.9 Hz, 1H), 2.57 (m, 1H), 2.43 (s, 3H), 2.14-1.91 (m, 7H), 1.75-1.64 (m, 3H), 0.91-0.82 (m, 1H), 0.53-0.50 (m, 2H), 0.20-0.14 (m, 2H). MS: (M+H m/z=328.2).

Example 58

6-[(3,4-trans)-1-benzyl-4-methylpyrrolidin-3-yl]-1-ethyl-1,5-dihydro-4H-pyrazolo[3,4-d]pyrimidin-4-one

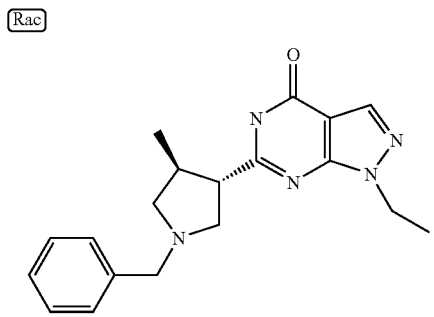

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-ethyl-1H-pyrazole-4-carboxamide provided the title compound. 400 MHz $^1$H NMR (CDCl$_3$) δ 8.02 (s, 1H), 7.42-7.27 (m, 5H), 4.38-4.30 (m, 2H), 3.83-3.80 (m, 1H), 3.63-3.59 (m, 1H), 3.49-3.35 (m, 1H), 2.99 (d, J=10.3 Hz, 1H), 2.83-2.80 (m, 1H), 2.55-2.50 (m, 1H), 2.44- 2.378 (m, 1H), 1.95-1.90 (m, 1H), 1.47 (t, J=7.1 Hz, 3H), 1.22 (t, J=10.3 Hz, 3H). MS: (M+H m/z=338.1).

Example 59

(a) 6-((3S,4S)-4-ethylpyrrolidin-3-yl)-1-isopropyl-1H-pyrazolo[3,4-d]pyrimidin-4(5H)-one

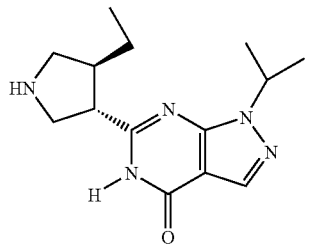

Following the procedure for the preparation of 1-cyclopentyl-6-[(3S,4S)-4-methylpyrrolidin-3-yl]-1H-pyrazolo[3,4-d]pyrimidin-4(5H)-one but substituting 6-[(3S,4S)-1-benzyl-4-ethylpyrrolidin-3-yl]-1-isopropyl-1,5-dihydro-4H-pyrazolo[3,4-d]pyrimidin-4-one provided the title compound. 400 MHz $^1$H NMR (CD$_3$OD) δ 8.02 (s, 1H), 5.10 (m, 1H), 3.78-3.60 (m, 3H), 3.32-3.28 (m, 1H), 3.10 (m, 1H), 2.62 (m, 1H), 1.65 (m, 1H), 1.58 (m, 1H), 1.49 (dd, J=6.6, 1.7 Hz, 6H), 0.97 (t, J=7.5 Hz, 3H). MS: (M+H m/z=276.1).

(b) 6-{(3,4-trans)-4-ethyl-1-[(2-methylpyrimidin-5-yl)methyl]pyrrolidin-3-yl}-1-isopropyl-1,5-dihydro-4H-pyrazolo[3,4-d]pyrimidin-4-one

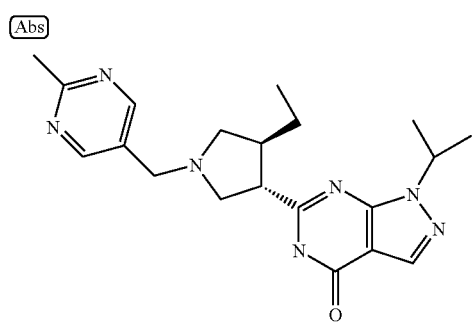

Following the procedure for the preparation of 1-cyclopentyl-6-[(3S,4S)-4-methylpyrrolidin-3-yl]-1H-pyrazolo[3,4-d]pyrimidin-4(5H)-one but substituting 6-((3S,4S)-4-ethylpyrrolidin-3-yl)-1-isopropyl-1H-pyrazolo[3,4-d]pyrimidin-4(5H)-one and 2-methylpyrimidine-5-carbaldehyde provided the title compound. 400 MHz $^1$H NMR (CDCl$_3$) δ 10.8 (brs, 1H), 8.62 (s, 2H), 8.01 (s, 1H), 5.00-4.93 (m, 1H), 3.66 (s, 2H), 3.25-3.20 (m, 1H), 3.02 (d, J=9.9 Hz, 1H), 2.95-2.92 (m, 1H), 2.70 (s, 3H), 2.62-2.58 (m, 1H), 2.28-2.23 (m, 1H), 1.98 (t, J=8.7 Hz, 1H), 1.62-1.52 (m, 1H), 1.48 (t, J=6.6 Hz, 6H), 1.46-1.42 (m, 1H), 3.08 (t, J=7.5 Hz, 3H). MS: (M+H m/z=382.2).

Example 60

(a) 1-(tetrahydro-2H-pyran-4-yl)hydrazine

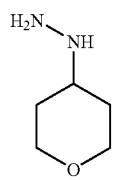

To a solution of tetrahydropyran-4-one (71.6 g, 715 mmol) in methanol (2 L) was added tert-butylcarbazate (100 g, 758 mmol) at ambient temp. The mixture was stirred at ambient temp for 20 h. The reaction mixture was concentrated under reduced pressure to dryness to afford a white solid (154 g). To a suspension of the white solid (154 g, 715 mmol) in water (1 L) was added acetic acid (500 mL, 8.73 mol) and the mixture was stirred for 30 min to get a clear solution. To this solution, solid NaCNBH$_3$ (44.5 g, 708 mmol) was added portion-wise. The mixture was stirred at ambient temp for 2 h. The mixture was then transferred to a 12 L flask, cooled to 0° C., and quenched with 1N NaOH (8.73 L, 8.73 mol). The mixture was extracted with CH$_2$Cl$_2$ (3×3 L) and dried over Na$_2$SO$_4$. The organic layer was filtered and concentrated to afford a white solid (164 g, contains ~15% of N-acetyl-N'-Boc-hydrazine derivative). Chromatography [silica, ethyl acetate/MeOH (95:5] gave 94 g of 90% pure boc-hydrazine. A solution of boc-hydrazine (50 g, 231 mmol) in methanol (500 mL) was added a solution of HCl in dioxane (462 mL, 1.85 mol, 4.0 M). The mixture was stirred at ambient temp overnight. Concentration of the reaction mixture under reduced pressure afforded the title compound as a white solid (43 g, 98%). 400 MHz $^1$H NMR (DMSO) δ 3.85-3.82 (m, 2H), 3.27-3.21 (m, 2H), 3.13-3.05 (m, 1H), 1.88-1.84 (m, 2H), 1.48-1.38 (m, 2H). MS: (M+H m/z=117.2).

(b) 5-amino-1-(tetrahydro-2H-pyran-4-yl)-1H-pyrazole-4-carbonitrile

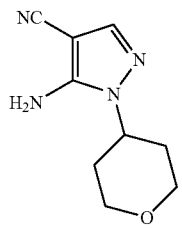

To a mixture of 1-(tetrahydro-2H-pyran-4-yl)hydrazine dihydrogen chloride (18 g, 96 mmol) in 200 mL of EtOH was added Et$_3$N (30 g, 40 mL, 288 mmol) at 0° C. (ice bath). The resulting mixture was stirred for 1 h, then a solution of 2-(ethoxymethylene)malononitrile (12 g, 96 mmol) in 100 mL of EtOH was added slowly to keep the reaction temp below 5° C. This mixture was stirred at ambient temp overnight and then heated to reflux for 2 hr. After removal of the solvent under vacuum, the residue was washed with 300 mL of water. The solid was collected, washed with additional 200 mL of water, 200 mL of 1:1 of hexane and ether, dried to give 17 g of yellow solid. 400 MHz $^1$H NMR (CD$_3$OD) δ 7.71 (s, 1H), 4.29-4.21 (m, 1H), 4.02 (dd, J=11.6, 4.6 Hz, 2H), 3.28 (t, J=1.7 Hz, 2H), 2.12-2.02 (m, 2H), 1.80-1.76 (m, 2H). MS: (M$^+$H m/z=193.1).

(c) 5-amino-1-(tetrahydro-2H-pyran-4-yl)-1H-pyrazole-4-carboxamide

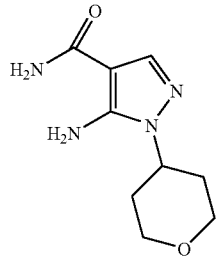

A stirred solution of 5-amino-1-(tetrahydro-2H-pyran-4-yl)-1H-pyrazole-4-carbonitrile (~228 mmol) in ethanol (300 mL) was treated with 35% aqueous H$_2$O$_2$ (100 mL) followed by aqueous ammonia (300 mL). The reaction mixture was stirred for 48 h at ambient temp and then quenched with aq saturated sodium thiosulfate (800 mL) and concentrated under reduced pressure to remove most of the ethanol. The resulting solid was removed by filtration and washed with water (2×200 mL) and ether (2×150 mL). The solid was dried in vacuo to constant weight (31 g, 65% yield for 2 steps). 400 MHz $^1$H NMR (CD$_3$OD) δ 7.67 (s, 1H), 4.27-4.21 (m, 1H), 4.03 (dd, J=11.6, 4.6 Hz, 2H), 3.28 (t, J=1.7 Hz, 2H), 2.14-2.04 (m, 2H), 1.81-1.78 (m, 2H). MS: (M$^1$H m/z=382.2).

(d) 6-[(3,4-trans)-1-benzyl-4-methylpyrrolidin-3-yl]-1-(tetrahydro-2H-pyran-4-yl)-1,5-dihydro-4H-pyrazolo[3,4-d]pyrimidin-4-one

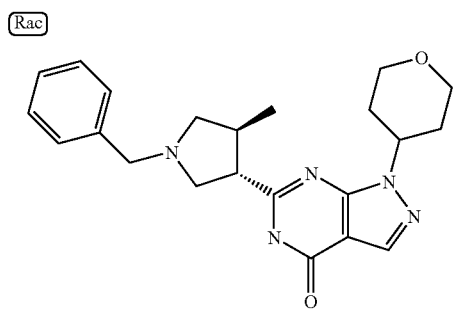

To a mixture of 5-amino-1-(tetrahydro-2H-pyran-4-yl-1H-pyrazole-4-carboxamide (6.0 g, 28.54 mmol) and (3,4-trans)-methyl 1-benzyl-4-methylpyrrolidine-3-carboxylate (13.3 g, 57.08 mmol) was added molecular sieves (pellets). To the stirred mixture was added a 1.0 M solution of t-BuOK in THF (57.1 ml, 57.08 mmol) and the resulting mixture was heated at reflux under an atmosphere of nitrogen with vigorous stirring overnight. Analysis of the reaction mixture by LC/MS indicated consumption of the starting material. The reaction mixture was cooled to ambient temp and solids were removed by filtration. The solids were washed with EtOAc (2×) and the combined filtrates were concentrated under reduced pressure. The remainder was partitioned between CH$_2$Cl$_2$ and H$_2$O and the aqueous and organic layers were separated. The aqueous phase was extracted with CH₂Cl₂ (1×) and the combined organic extracts were dried over Na₂SO₄, filtered and concentrated under reduced pressure. The remaining residue was purified by chromatography (silica gel, 1% Et₃N in EtOAc) to afford the title compound (7.8 g, 70% yield) as an off-white solid. 400 MHz ¹H NMR (CDCl₃) δ 8.02 (s, 1H), 7.39-7.25 (m, 6H), 4.83-4.75 (m, 1H), 4.14-4.09 (m, 2H), 3.82 (m, 1H), 3.62-3.54 (m, 3H), 3.39-3.37 (m, 1H), 3.00 (m, 1H), 2.83 (m, 1H), 2.66-2.27 (m, 4H), 2.10-1.83 (m, 3H), 1.20 (d, J=6.6 Hz, 3H). MS: (M⁺H m/z=394.2).

Example 61

6-[(3S,4S)-1-benzyl-4-methylpyrrolidin-3-yl]-1-(tetrahydro-2H-pyran-4-yl)-1,5-dihydro-4H-pyrazolo[3,4-d]pyrimidin-4-one

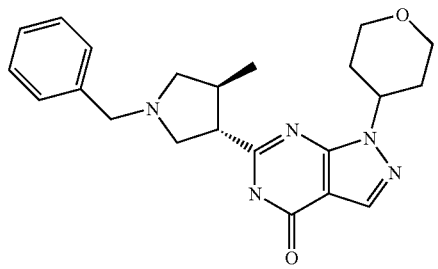

The racemate of Example 60 was separated on Chiralcel OD-H chiral HPLC column, Mobile Phase 70/30 Heptane/EtOH, T_R=11.465, to provide the enantiomer. 400 MHz ¹H NMR (CDCl₃) δ 8.02 (s, 1H), 7.39-7.25 (m, 6H), 4.82-4.76 (m, 1H), 4.14-4.09 (m, 2H), 3.82-3.79 (m, 1H), 3.62-3.54 (m, 3H), 3.37 (d, J=8.7 Hz, 1H), 3.00 (d, J=9.9 Hz, 1H), 2.79 (dd, J=6.3, 2.5 Hz, 1H), 2.52-2.48 (m, 1H), 2.42-2.30 (m, 3H), 1.94-1.82 (m, 3H), 1.20 (d, J=6.6 Hz, 3H). MS: (M⁺H m/z=394.2).

Example 62

(a) (3,4-trans)-ethyl-1-benzyl-4-(2,2,2-trifluoroethyl)pyrrolidine-3-carboxylate

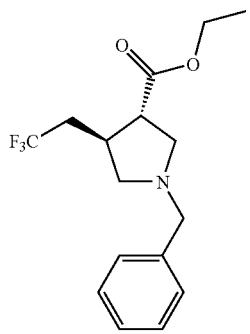

Following the procedure for the preparation of (3,4-trans)-methyl-1-benzyl-4-methylpyrrolidine-3-carboxylate but substituting (E)-methyl-5,5,5-trifluoropent-2-enoate provided the title compound. 400 MHz ¹H NMR (CDCl₃) δ 7.32-7.21 (m, 5H), 4.18-4.10 (m, 2H), 3.67-3.55 (m, 2H), 2.90-2.63 (m, 4H), 2.43-2.34 (m, 2H), 2.24-2.15 (m, 1H), 1.27-1.22 (m, 3H), 0.88-0.85 (m, 1H).

(b) 6-[(3,4-trans)-1-benzyl-4-(2,2,2-trifluoroethyl)pyrrolidin-3-yl]-1-cyclopentyl-1,5-dihydro-4H-pyrazolo[3,4-d]pyrimidin-4-one

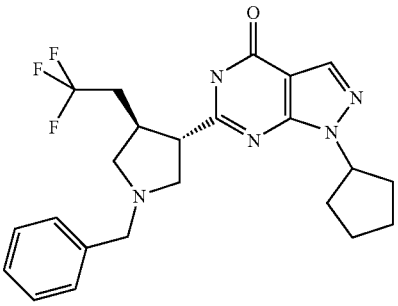

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclopentyl-1H-pyrazole-4-carboxamide and (3,4-trans)ethyl-1-benzyl-4-(2,2,2-trifluoroethyl)pyrrolidine-3-carboxylate provided the title compound. 400 MHz ¹H NMR (CDCl₃) δ 8.02 (s, 1H), 7.36-7.26 (m, 5H), 5.12-5.08 (m, 1H), 3.85-3.81 (m, 1H), 3.60-3.57 (m, 1H), 3.42 (t, J=8.3 Hz, 1H), 3.02-2.96 (m, 2H), 2.64 (m, 1H), 2.53-2.44 (m, 2H), 2.34-1.89 (m, 6H), 1.81-1.62 (m, 4H).

Example 63

(a) 1-(4,4-difluorocyclohexyl)hydrazine

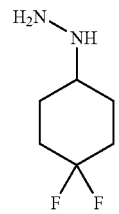

To a solution of 4,4-difluorocyclohexanol (0.9 g) in toluene was added triphenyl phosphine (2.6 g) and di-t-butyldiazacarboxalate (1.82 g) and the reaction mixture stirred for 18 h. The reaction mixture was concentrated and methanol was added (13 mL). To the methanol solution HCl in dioxane (4M, 13 mL) was added. The reaction mixture was stirred for 3 h and concentrated. The reaction mixture was partitioned between water and ethyl acetate. The layers were separated and the aqueous layer was extracted 3× with ethyl acetate. The organic layer was dried with magnesium sulfate, filtered and concentrated. The title compound was used without purification in the preparation of 5-amino-1-(4,4-difluorocyclohexyl)-1H-pyrazole-4-carbonitrile. 400 MHz ¹H NMR (CD₃OD) δ 2.15-2.07 (m, 4H), 2.00-1.81 (m, 2H), 1.68-1.58 (m,2H). (M⁺H m/z=279.0).

(b) 5-amino-1-(4,4-difluorocyclohexyl)-1H-pyrazole-4-carbonitrile

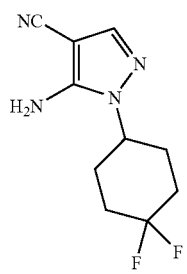

Following the procedure for the preparation of 5-amino-1-(2-methoxyphenyl)-1H-pyrazole-4-carbonitrile but substituting 1-(4,4-difluorocyclohexyl)hydrazine provided the title compound. 400 MHz ¹H NMR (CDCl₃) δ 7.5 (m, 1H), 3.90 (m, 1H), 2.40-1.00 (m, 8H).

(c) 5-amino-1-(4,4-difluorocyclohexyl)-1H-pyrazole-4-carboxamide

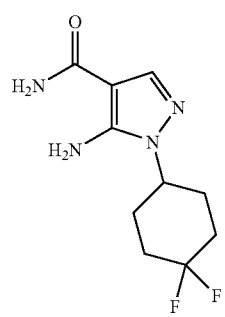

Following the procedure for the preparation of 5-amino-1-(2-methoxyphenyl)-1H-pyrazole-4-carboxamide but substituting 5-amino-1-(4,4-difluorocyclohexyl)-1H-pyrazole-4-carbonitrile provided the title compound. 400 MHz ¹H NMR (CD₃OD) δ 8.01 (s, 1H), 4.19 (m, 1H), 2.22-1.90 (m, 8H).

(d) 6-[(3,4-trans)-1-benzyl-4-methylpyrrolidin-3-yl]-1-(4,4-difluorocyclohexyl)-1,5-dihydro-4H-pyrazolo[3,4-d]pyrimidin-4-one

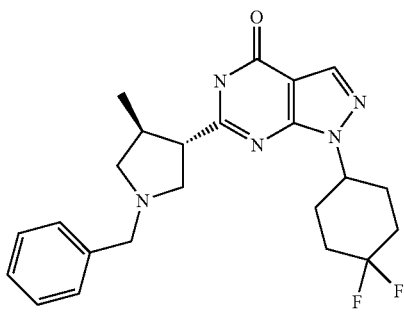

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-(4,4-difluorocyclohexyl)-1H-pyrazole-4-carboxamide provided the title compound. 400 MHz ¹H NMR (CDCl₃) δ 8.00 (s, 1H), 7.40-7.25 (m, 5H), 4.73-4.67 (m, 1H), 3.85-3.82 (m, 1H), 3.64-3.61 (m, 1H), 3.38 (t, J=8.7 Hz, 1H), 3.00 (m, 1H), 2.83 (m, 1H), 2.56-2.52 (m, 1H), 2.43-2.25 (m, 5H), 2.04-1.90 (m, 5H), 1.20 (d, J=7.1 Hz, 3H). MS: (M⁺H m/z=428.1).

Example 64

(a) 5-amino-1-(2,2,2-trifluoroethyl)-1H-pyrazole-4-carbonitrile

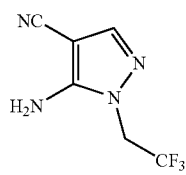

Following the procedure for the preparation of 5-amino-1-(2-methoxyphenyl)-1H-pyrazole-4-carbonitrile but substituting 1-(2,2,2-trifluoroethyl)hydrazine provided the title compound. 400 MHz ¹H NMR (CDCl₃) δ 7.60 (s, 1H), 4.59 (m, 2H), 4.40 (brs, 2H).

(b) 5-amino-1-(2,2,2-trifluoroethyl)-1H-pyrazole-4-carboxamide

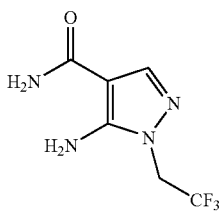

Following the procedure for the preparation of 5-amino-1-(2-methoxyphenyl)-1H-pyrazole-4-carboxamide but substituting 5-amino-1-(2,2,2-trifluoroethyl)-1H-pyrazole-4-carbonitrile provided the tile compound. 400 MHz ¹H NMR (DMSO) δ 7.75 (s, 1H), 7.30 (brs, 1H), 6.78 (brs, 1H) 6.58 (m, 2H), 4.88 (m, 2H).

(c) 6-[(3,4-trans)-1-benzyl-4-methylpyrrolidin-3-yl]-1-(2,2,2-trifluoroethyl)-1,5-dihydro-4H-pyrazolo[3,4-d]pyrimidin-4-one]

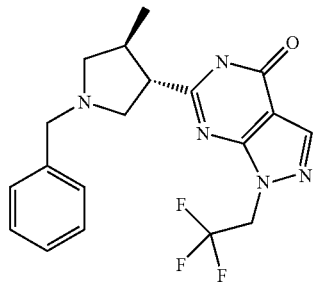

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-(2,2,2-trifluoroethyl)-1H-pyrazole-4-carboxamide provided the title compound. 400 MHz $^1$H NMR (CDCl$_3$) δ 8.15 (s, 1H), 7.59-7.57 (m, 2H), 7.44-7.41 (m, 3H), 4.96-4.88 (m, 2H), 4.22-4.11 (m, 2H), 3.57-3.37 (m, 4H), 2.85 (m, 2H), 1.26-1.23 (m, 3H), MS: (M$^+$H m/z=392.1).

Example 65

1-isopropyl-6-[(3S,4S)-4-methyl-1-(1,5-naphthyridin-4-ylmethyl)pyrrolidin-3-yl]-1,5-dihydro-4H-pyrazolo[3,4-d]pyrimidin-4-one

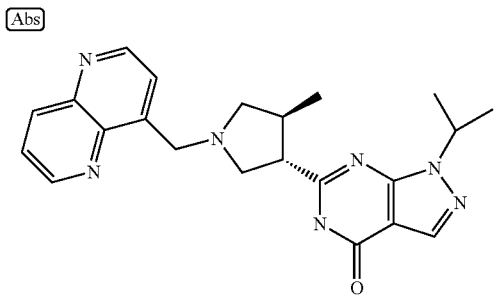

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and 1,5-naphthyridine-4-carbaldehyde provided the title compound. 400 MHz $^1$H NMR (CDCl$_3$) δ 9.09-9.08 (m, 1H), 8.95-8.87 (m, 1H), 8.44-8.39 (m, 1H), 8.00 (s, 1H), 7.73-7.70 (m, 1H), 7.67-7.64 (m, 1H), 5.00-4.96 (m, 1H), 4.56-4.53 (m, 1H), 4.33-4.29 (m, 1H), 3.34 (t, J=8.3 Hz, 1H), 3.19 (d, J=9.5 Hz, 1H), 2.91-2.82 (m, 2H), 2.47-2.43 (m, 1H), 2.12 (t, J=8.3 Hz, 1H), 1.48 (dd, J=9.9. 6.6 Hz, 6H), 1.18 (d, J=7.1 Hz, 3H). MS: (M$^+$H m/z=404.2).

Example 66

1-isopropyl-6-[(3S,4S)-4-methyl-1-(1,8-naphthyridin-4-ylmethyl)pyrrolidin-3-yl]-1,5-dihydro-4H-pyrazolo[3,4-d]pyrimidin-4-one]

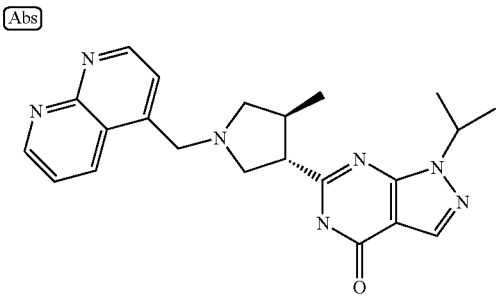

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and 1,8-naphthyridine-4-carbaldehyde provided the title compound. 400 MHz $^1$H NMR (CDCl$_3$) δ 9.15 (dd, J=4.1, 1.7 Hz, 1H), 9.07 (d, J=4.6 Hz, 1H), 8.69 (dd, J=8.3, 1.66 Hz, 1H), 7.99 (s, 1H), 7.69-7.65 (m, 1H), 7.46 (d, J=4.6 Hz, 1H), 5.00-4.93 (m, 1H), 4.14 (s, 3H), 3.26 (t, J=8.3 Hz, 1H), 3.03 (d, J=9.5 Hz, 1H), 2.92-2.90 (m, 1H), 2.80-2.76 (m, 1H), 2.52-2.43 (m, 1H), 1.50-1.46 (m, 6H), 1.20 (d, J=6.6 Hz, 3H). MS: (M$^+$H m/z=404.1).

Example 67

1-isopropyl-6-[3S,4S)-4-methyl-1-(quinolin-4-ylmethyl)pyrrolidin-3-yl]-1,5-dihydro-4H-pyrazolo[3,4-d]pyrimidin-4-one

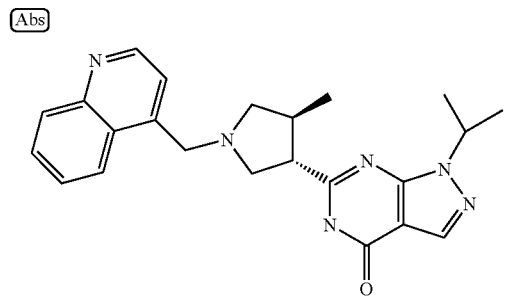

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and quinoline-4-carbaldehyde provided the title compound. 400 MHz $^1$H NMR (CDCl$_3$) δ 10.63 (brs, 1H), 8.85 (d, J=4.6 Hz, 1H), 8.26-4.24 (m, 1H), 8.13-8.11 (m, 1H), 7.99 (s, 1H), 7.77-7.69 (m, 2H), 7.39 (d, J=4.6 Hz, 1H), 5.00-4.94 (m, 1H), 4.13 (d, J=3.3 Hz, 2H), 3.32 (t, J=8.3 Hz, 1H), 3.06 (d, J=9.5 Hz, 1H), 2.89-2.87 (m, 1H), 2.74-2.70 (m, 1H), 2.46-2.42 (m, 1H), 2.04 (t, J=8.7 Hz, 1H), 1.48 (dd, J=12.9, 7.1 Hz, 6H), 1.20 (d, J=7.1 Hz, 3H). MS: (M+H m/z 403.2).

Example 68

1-isopropyl-6-[(3S,4S)-4-methyl-1-(pyrido[2,3-b]pyrazin-8-ylmethyl)pyrrolidin-3-yl]-1,5-dihydro-4H-pyrazolo[3,4-d]pyrimidin-4-one

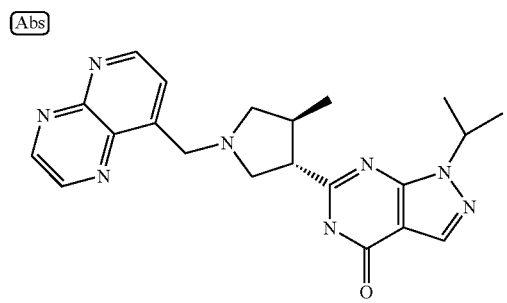

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3S,4S)-4-methylpyrrolidin-3-yl]-1H-pyrazolo[3,4-d]pyrimidin-4(5H)-one and pyrido[2,3-b]pyrazine-8-carbaldehyde provided the title compound. 400 MHz $^1$H NMR (CDCl$_3$) δ 10.00 (brs, 1H), 9.16-9.10 (m, 3H), 8.00 (s, 1H), 7.78 (m, 1H), 5.00-4.97 (m, 1H), 4.63-4.58

(m, 1H), 4.34-4.18 (m, 1H), 3.30 (m, 1H), 3.27 (m, 1H), 2.92-2.77 (m, 2H), 2.49-2.38 (m, 1H), 2.09-1.97 (m, 1H), 1.48 (dd, J=10.8, 6.6 Hz, 6H), 1.20 (d, J=6.6 Hz, 3H). MS: (M+H m/z 405.2).

Example 69

1-isopropyl-6-{(3,4-trans)-1-[(6-methoxy-1,5-naphthyridin-4-yl)methyl]-4-methylpyrrolidin-3-yl}-1,5-dihydro-4H-pyrazolo[3,4-d]pyrimidin-4-one

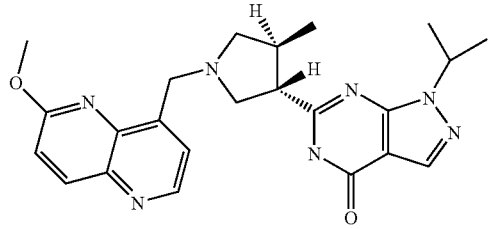

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3,4-trans)-4-methylpyrrolidin-3-yl]-1H-pyrazolo[3,4-d]pyrimidin-4(5H)-one and 6-methoxy-1,5-naphthyridine-4-carbaldehyde provided the title compound. 400 MHz $^1$H NMR (CDCl$_3$) δ 8.78 (d, J=4.6 Hz, 1H), 8.21 (d, J=9.1 Hz, 1H), 8.01 (s, 1H), 7.63 (m, 1H), 7.17 (d, J=9.1 Hz, 1H), 5.01-4.95 (m, 1H), 4.4 (m, 1H), 4.07 (s, 3H), 3.48 (m, 1H), 3.18 (m, 1H), 2.89-2.75 (m, 2H), 2.43 (m, 1H), 2.10-2.08 (m, 2H), 1.49 (dd, J=11.6, 6.6 Hz, 6H), 1.21 (d, J=6.6 Hz, 3H). MS: (M+H m/z 434.2).

Example 70

6-{(3,4-trans)-1-[(8-fluoroquinolin-2-yl)methyl]-4-methylpyrrolidin-3-yl}-1-isopropyl-1,5-dihydro-4H-pyrazolo[3,4-d]pyrimidin-4-one

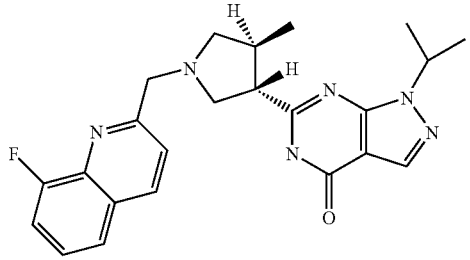

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3,4-trans)-4-methylpyrrolidin-3-yl]-1H-pyrazolo[3,4-d]pyrimidin-4(5H)-one and 8-fluoroquinoline-2-carbaldehyde provided the title compound. 400 MHz $^1$H NMR (CDCl$_3$) δ 8.27-8.25 (m, 1H), 8.04 (s, 1H), 7.86 (m, 1H), 7.66-7.60 (m, 1H), 7.50-7.38 (m, 2H), 5.04-4.97 (m, 1H), 4.30 (m, 1H), 4.18 (m, 1H), 3.47 (m, 2H), 3.28 (m, 1H), 3.00 (m, 1H), 2.59 (m, 1H), 2.40 (m, 1H), 1.50 (dd, J=11.2, 6.6 Hz, 6H), 1.22 (d, J=7.1 Hz, 3H). MS: (M+H m/z 421.2).

Example 71

1-isopropyl-6-{(y)-1-[(6-methoxyquinolin-4-yl)methyl]-4-methylpyrrolidin-3-yl}-1,5-dihydro-4H-pyrazolo[3,4-d]pyrimidin-4-one

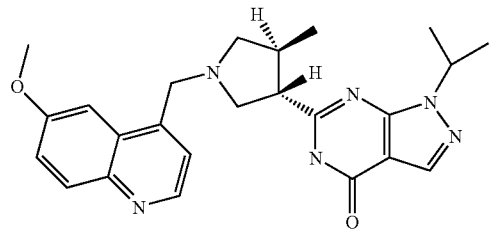

Following the procedure for the preparation of 1-cyclopentyl-6-[(3,4-trans)-4-methyl-1-(pyridin-3-ylmethyl)pyrrolidin-3-yl]-1,5-dihydro-4H-pyrazolo[3,4-d]pyrimidin-4-one but substituting 1-isopropyl-6-[(3,4-trans)-4-methylpyrrolidin-3-yl]-1H-pyrazolo[3,4-d]pyrimidin-4(5H)-one and 6-methoxyquinoline-4-carbaldehyde provided the title compound. 400 MHz $^1$H NMR (CD$_3$OD) δ 8.87 (d, J=5.0 Hz, 1H), 8.08 (d, J=9.5 Hz, 1H), 8.00-7.95 (m, 2H), 7.70 (d, J=2.5 Hz, 1H), 7.61 (d, J=2.9 Hz, 1H), 5.03-4.97 (m, 1H), 4.08 (s, 3H), 4.08-4.02 (m, 3H), 3.91-3.86 (m, 2H), 3.46-3.41 (m, 1H), 3.33 (s, 1H), 2.94 (m, 1H), 1.48 (d, J=7.1 Hz, 3H), 1.42 (d, J=6.6 Hz, 3H), 1.21 (d, J=6.6 Hz, 3H). MS: (M+H m/z 433.2).

Example 72

(a) 5-amino-1-cyclobutyl-1H-pyrazole-4-carbonitrile

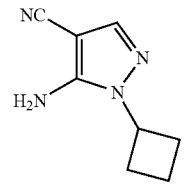

Following the procedure for the preparation of 5-amino-1-(2-methoxyphenyl)-1H-pyrazole-4-carbonitrile but substituting 1-cyclobutylhydrazine provided the title compound. 400 MHz $^1$H NMR (CDCl$_3$) δ 7.50 (s, 1H), 4.48-4.40 (m, 1H), 4.23 (m, 2H), 2.70-2.58 (m, 2H), 2.48-2.35 (m, 2H), 1.97-1.79 (m, 2H). MS: (M+H m/z 163.1).

(b) 5-amino-1-cyclobutyl-1H-pyrazole-4-carboxamide

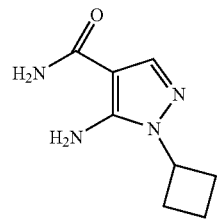

Following the procedure for the preparation of 5-amino-1-(2-methoxyphenyl)-1H-pyrazole-4-carboxamide but substituting 5-amino-1-cyclobutyl-1H-pyrazole-4-carbonitrile provided the title compound. 400 MHz $^1$H NMR (CD$_3$OD) δ 7.71 (s, 1H), 4.71-4.55 (m, 1H), 2.61-2.50 (m,2H), 2.46-2.31 (m, 2H), 1.89-1.83 (m, 2H).

(c) 6-[(3,4-trans)-1-benzyl-4-methylpyrrolidin-3-yl]-1-cyclobutyl-1,5-dihydro-4H-pyrazolo[3,4-d]pyrimidin-4-one

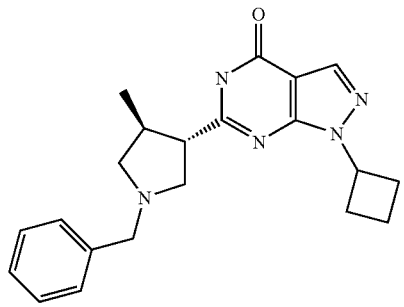

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-cyclobutyl-1H-pyrazole-4-carboxamide provided the title compound. 400 MHz $^1$H NMR (CDCl$_3$) δ 8.03 (d, J=3.32 Hz, 1H), 7.35-7.24 (m, 5H), 5.25-5.20 (m, 1H), 3.79-3.57 (m, 3H), 3.36-3.32 (m, 1H), 2.98 (d, J=9.9 Hz, 1H), 2.80-2.60 (m, 3H), 3.53-2.38 (m, 3H), 1.92-1.79 (m, 3H), 1.25-1.12 (m, 3H). MS: (M+H m/z 464.2).

Example 73

(a) 6-[(3S,4S)-4-methylpyrrolidin-3-yl]-1-(tetrahydro-2H-pyran-4-yl)-1H-pyrazolo[3,4-d]pyrimidin-4(5H)-one

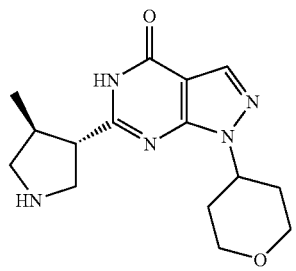

6-[(3S,4S)-1-benzyl-4-methylpyrrolidin-3-yl]-1-(tetrahydro-2H-pyran-4-yl)-1,5-dihydro-4H-pyrazolo[3,4-d]pyrimidin-4-one (5.6 g) was dissolved in 100 mL of methanol and added to a Parr bottle. Palladium hydroxide (3.76 g) was added along with 3.56 mL of concentrated hydrochloric acid. The reaction mixture was placed on a hydrogenator under 40 psi of H2 for 18 h. The reaction mixture was filtered through Celite and concentrated to provide 4.47 g of the title compound as the hydrogen chloride salt. 400 MHz $^1$H NMR (CD$_3$OD) δ 8.03 (s, 1H), 4.49 (m, 1H), 4.09-4.06 (m, 2H), 3.74-3.57 (m, 4H), 3.24 (m, 1H), 3.05 (m, 1H), 2.89 (m, 1H), 2.77 (m, 1H), 2.30 (m, 2H), 1.90 (m, 2H), 1.22 (d, J=6.6 Hz, 3H). MS: (M$^+$H m/z=304.2).

(b) 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one

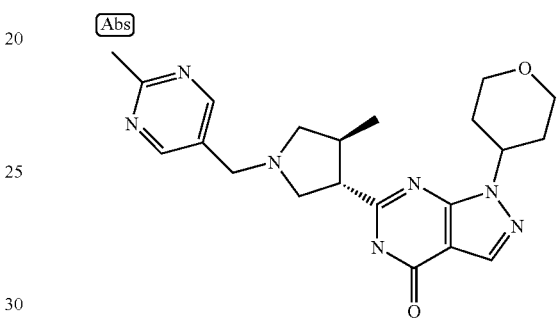

To a solution of 6-[(3S,4S)-4-methylpyrrolidin-3-yl]-1-(tetrahydro-2H-pyran-4-yl)-1H-pyrazolo[3,4-d]pyrimidin-4(5H)-one hydrogen chloride (493 mg) in 1,2-dichloroethane (10 mL) was added acetic acid (174 mg), 2-methylpyrimidine-5-carbaldehyde (236 mg) and sodium triacetoxy borohydride (635 mg). The reaction mixture was heated at 50° C. overnight. The reaction mixture was concentrated onto silica gel and purified by CombiFlash chromatography to provide the title compound (146 mg). 400 MHz $^1$H NMR (CDCl$_3$) δ 8.63 (s, 2H), 8.01 (s, 1H), 4.82-4.76 (m, 1H), 4.12-4.08 (m, 2H), 3.68 (d, J=5.0 Hz, 3H), 3.64-3.54 (m, 2H), 3.28 (t, J=8.3 Hz, 1H), 3.04 (d, J=9.9 Hz, 1H), 2.89-2.86 (m, 1H), 2.71 (s, 3H), 2.66-2.62 (m, 1H), 2.49-2.27 (m, 3H), 1.97 (t, J=7.9 Hz, 1H), 1.91-1.83 (m, 2H), 1.19 (d, J=7.05 Hz, 3H). MS: (M+H m/z 410.2).

Example 74

6-{(3,4-trans)-4-ethyl-1-[(2-methylpyrimidin-5-yl)methyl]pyrrolidin-3-yl}-1-tetrahydro-2H-pyran-4-yl)-1,5-dihydro-4H-pyrazolo[3,4-d]pyrimidin-4-one

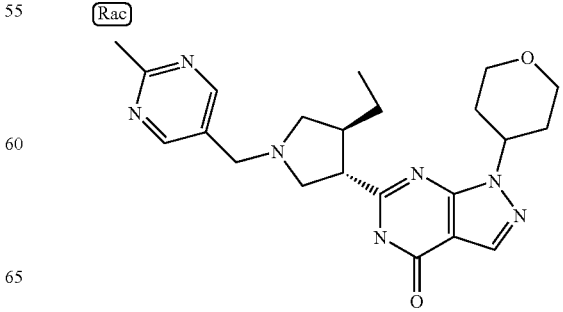

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-[(3,4-trans)-4-ethylpyrrolidin-3-yl]-1-(tetrahydro-2H-pyran-4-yl)-1H-pyrazolo[3,4-d]pyrimidin-4(5H)-one hydrogen chloride provided the title compound. 400 MHz $^1$H NMR (CDCl$_3$) δ 10.55 (brs, 1H), 8.64 (s, 2H), 8.01 (s, 1H), 4.81-4.73 (m, 1H), 4.11-4.09 (m, 2H), 3.68 (s, 2H), 3.61-3.53 (m, 2H), 3.28 (t, J=8.7 Hz, 1H), 3.03 (d, J=9.9 Hz, 1H), 2.94-2.92 (m, 1H), 2.71 (s, 3H), 2.57-2.53 (m, 1H), 2.40-2.20 (m, 3H), 1.96 (t, J=8.7 Hz, 1H), 1.89-1.84 (m, 2H), 1.64-1.57 (m, 1H), 1.52-1.44 (m, 1H), 0.91 (t, J=7.1 Hz, 3H). MS: (M+H m/z 424.3).

Example 75

6-{(3S,4S)-4-methyl-1-[(5-methylpyrazin-2-yl)methyl]pyrrolidin-3-yl}-1-(tetrahydro-2H-pyran-4-yl)-1,5-dihydro-4H-pyrazolo[3,4-d]pyrimidin-4-one

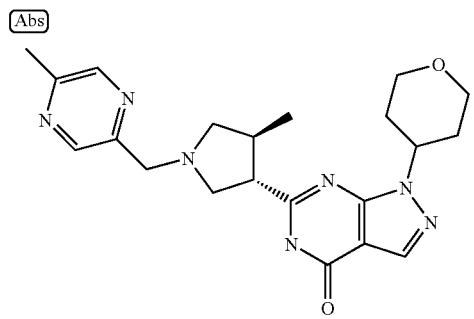

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 5-methylpyrazine-2-carbaldehyde provided the title compound. 400 MHz $^1$H NMR (CDCl$_3$) δ 8.53 (s, 1H), 8.47 (s, 1H), 8.03 (s, 1H), 4.83-4.79 (m, 1H), 4.12-4.03 (m, 2H), 3.78-3.75 (m, 1H), 3.61-3.55 (m, 2H), 3.46-3.40 (m, 1H), 3.12-3.09 (m, 1H), 2.87 (m, 1H), 2.64 (m, 1H), 2.53 (m, 2H), 2.47-2.28 (m, 4H), 2.16 (m, 2H), 1.91-1.84 (m, 2H), 1.23-1.20 (m, 3H). MS: (M+H m/z 410.3).

Example 76

6-{(3S,4S)-1-[(6-methoxypyridin-3-yl)methyl]-4-methylpyrrolidin-3-yl}-1-(tetrahydro-2H-pyran-4-yl)-1,5-dihydro-4H-pyrazolo[3,4-d]pyrimidin-4-one

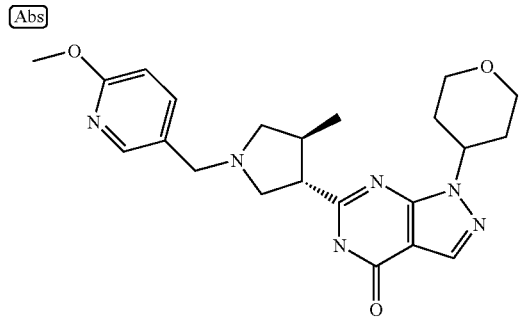

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-methoxynicotinaldehyde provided the title compound. 400 MHz $^1$H NMR (CDCl$_3$) δ 8.03 (d, J=2.1 Hz, 1H), 8.01 (s, 1H), 7.69 (dd, J=8.7, 2.5 Hz, 1H), 7.77 (d, J=8.7 Hz, 1H), 4.83-4.75 (m, 1H), 4.14-4.08 (m, 2H), 3.89 (s, 3H), 3.72-3.68 (m, 1H), 3.62-3.3.54 (m, 3H), 3.33 (t, J=8.3 Hz, 1H), 2.99 (d, J=9.9 Hz, 1H), 2.84-2.82 (m, 1H), 2.57-2.53 (m, 1H), 2.43-2.27 (m, 3H), 1.95-1.82 (m, 3H), 1.19 (d, J=6.6 Hz, 3H). MS: (M+H m/z 425.3).

Example 77

6-[(3S,4S)-4-methyl-1-(quinolin-3-ylmethyl)pyrrolidin-3-yl]-1-(tetrahydro-2H-pyran-4-yl)-1,5-dihydro-4H-pyrazolo[3,4-d]pyrimidin-4-one

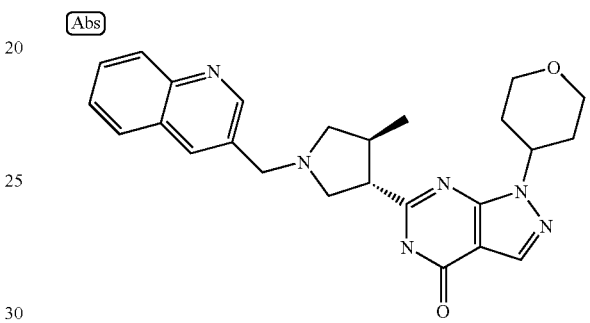

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting quinoline-3-carbaldehyde provided the title compound. 400 MHz $^1$H NMR (CDCl$_3$) δ 8.86 (d, J=2.1 Hz, 1H), 8.27 (d, J=1.7 Hz, 1H), 8.08-8.06 (m, 1H), 8.03 (s, 1H), 7.90-7.57 (m, 1H), 7.70-7.66 (m, 1H), 7.56-7.52 (m, 1H), 4.83-4.75 (m, 1H), 4.11-4.07 (m, 2H), 4.02-3.99 (m, 1H), 3.85-3.82 (m, 1H), 3.60-3.53 (m, 2H), 3.33 (t, J=8.3 Hz, 1H), 3.05 (d, J=9.9 Hz, 1H), 2.87-2.85 (m, 1H), 2.68-2.60 (m, 1H), 2.53-2.40 (m, 1H), 2.38-2.29 (m, 2H), 2.05 (m, 1H), 1.90-1.84 (m, 2H), 1.19 (d, J=6.6 Hz, 3H). MS: (M+H m/z 445.1).

Example 78

6-{(3S,4S)-4-methyl-1-[(2-methylpyrimidin-4-yl)methyl]pyrrolidin-3-yl}-1-(tetrahydro-2H-pyran-4-yl)-1,5-dihydro-4H-pyrazolo[3,4-d]pyrimidin-4-one

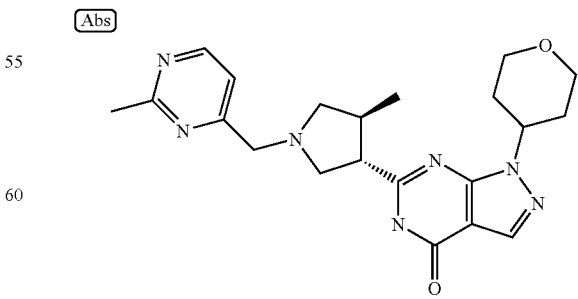

Following the procedure for the preparation of 6-{(3S,4S)-4-methyl-1-[(2-methylpyrimidin-5-yl)methyl]pyrrolidin-3- yl}-1-(tetrahydro-2H-pyran-4-yl)-1,5-dihydro-4H-pyrazolo[3,4-d]pyrimidin-4-one but substituting 2-methylpyrimidine-4-carbaldehyde provided the title compound. 400 MHz $^1$H NMR (CDCl$_3$) δ 8.59 (d, J=5.0 Hz, 1H), 8.03 (s, 1H), 7.20 (d, J=5.0 Hz, 1H), 4.84-4.76 (m, 1H), 4.13-4.08 (m, 2H), 3.97-3.93 (m, 1H), 3.70-3.67 (m, 1H), 3.61-3.53 (m, 2H), 3.40 (t, J=8.3 Hz, 1H), 3.14 (d, J=9.5 Hz, 1H), 2.88 (m, 1H), 2.72 (s, 3H), 2.69-2.63 (m, 1H), 2.47-2.27 (m, 3H), 2.10-2.08 (m, 1H), 1.91-1.83 (m, 2H), 1.21 (d, J=7.1 Hz, 3H). MS: (M+H m/z 410.2).

Example 79

6-{(3S,4S)-4-methyl-1-[(6-methylpyridin-3-yl)methyl]pyrrolidin-3-yl}-1-(tetrahydro-2H-pyran-4-yl)-1,5-dihydro-4H-pyrazolo[3,4-d]pyrimidin-4-one

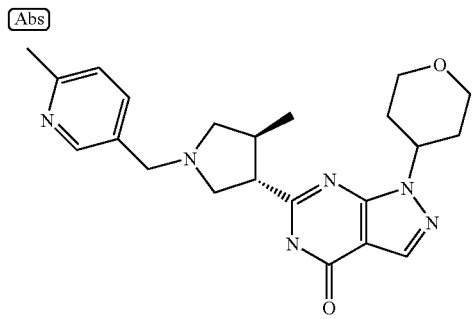

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-methylnicotinaldehyde provided the title compound. 400 MHz $^1$H NMR (CD$_3$OD) δ 8.38 (d, J=2.1 Hz, 1H), 7.99 (s, 1H), 7.77 (d, J=2.07 Hz, 1H), 7.75 (d, J=2.07 Hz, 1H), 4.94-4.83 (m, 1H), 4.09-4.05 (m, 2H), 3.78-3.57 (m, 4H), 3.31-3.28 (m, 1H), 3.11-3.06 (m, 1H), 3.01-2.91 (m, 2H), 2.72-2.65 (m, 1H), 2.50 (s, 3H), 2.33-2.23 (m, 3H), 1.90-1.86 (m, 2H), 1.14 (d, J=7.1 Hz, 3H). MS: (M+H m/z 409.2).

Example 80

6-[(3S,4S)-4-methyl-1-{[6-(trifluoromethyl)pyridin-3-yl]methyl}pyrrolidin-3-yl]-1-(tetrahydro-2H-pyran-4-yl)-1,5-dihydro-4H-pyrazolo[3,4-d]pyrimidin-4-one

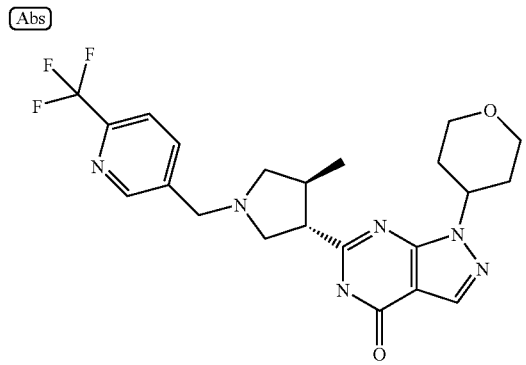

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-trifluoromethyl)nicotinaldehyde provided the title compound. 400 MHz $^1$H NMR (CDCl$_3$) δ 8.64 (d, J=1.7 Hz, 1H), 8.01 (s, 1H), 7.99 (d, J=1.7 Hz, 1H), 7.70 (d, J=8.3 Hz, 1H), 4.83-4.77 (m, 1H), 4.13-4.08 (m, 2H), 3.86-3.74 (m, 2H), 3.61-3.53 (m, 2H), 3.30 (t, J=8.7 Hz, 1H), 3.03 (d, J=9.9 Hz, 1H), 2.92-2.89 (m, 1H), 2.72-2.67 (m, 1H), 2.50-2.47 (m, 1H), 2.38-2.30 (m, 2H), 2.07-2.03 (m, 1H), 1.91-1.82 (m, 2H), 1.20 (d, J=7.1 Hz, 3H). MS: (M+H m/z 412.2).

Example 81

6-{(3S,4S)-4-methyl-1-[(1-methyl-1H-imidazo[4,5-c]pyridin-2-yl)methyl]pyrrolidin-3-yl}-1-(tetrahydro-2H-pyran-4-yl)-1,5-dihydro-4H-pyrazolo[3,4-d]pyrimidin-4-one

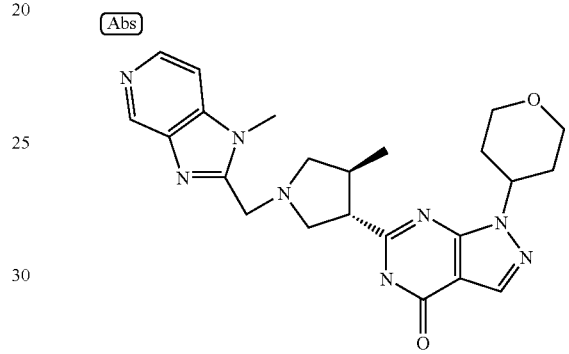

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 1-methyl-1H-imidazo[4,5-c]pyridine-2-carbaldehyde provided the title compound. 400 MHz $^1$H NMR (CDCl$_3$) δ 10.83 (brs 1H), 9.01 (s, 1H), 8.41 (d, J=15.8 Hz, 1H), 7.98 (s, 1H), 7.30 (d, J=4.98 Hz, 1H), 4.79-4.75 (m, 1H), 4.13-4.06 (m, 3H), 4.00-3.96 (s, 4H), 3.60-3.52 (m, 2H), 3.30 (t, J=8.7 Hz, 1H), 3.07 (d, J=9.9 Hz, 1H), 2.92-2.89 (m, 1H), 2.82-2.77 (m, 1H), 2.48-2.45 (m, 1H), 2.36-2.27 (m, 2H), 2.19-2.17 (m, 1H), 1.89-1.79 (m, 2H), 1.23 (d, J=6.6 Hz, 3H). MS: (M+H m/z 449.2).

Example 82

6-{(3S,4S)-1-[(1,3-dimethyl-1H-pyrazolo-5-yl)methyl]-4-methylpyrrolidin-3-yl}-1-(tetrahydro-2H-pyran-4-yl)-1,5-dihydro-4H-pyrazolo[3,4-d]pyrimidin-4-one

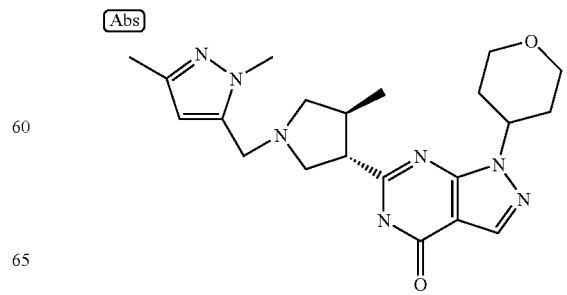

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 1,3-dimethyl-1H-pyrazole-5-carbaldehyde provided the title compound. 400 MHz $^1$H NMR (CDCl$_3$) δ 7.98 (s, 1H), 5.94 (s, 1H), 4.81-4.75 (m, 1H), 4.57 (s, 1H), 4.11-4.06 (m, 2H), 3.84 (s, 2H), 3.77 (s, 1H), 3.71-3.52 (m, 2H), 3.31 (t, J=8.3 Hz, 1H), 3.01 (d, J=9.9 Hz, 1H), 2.85-2.83 (m, 1H), 2.62-2.57 (m, 1H), 2.46-2.25 (m, 2H), 2.17-2.16 (m, 6H), 1.96-1.81 (m, 2H), 1.18 (d, J=6.6 Hz, 3H). MS: (M+H m/z 412.2).

Example 83

(a) 1-cyclobutyl-6-[(3,4-trans)-4-methylpyrrolidin-3yl]-1H-pyrazolo[3,4-d]pyrimidin-4(5H)-one

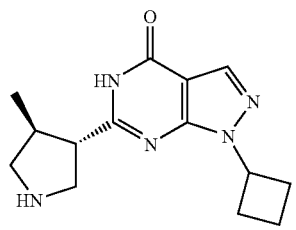

Following the procedure for the preparation of 6-[(3S,4S)-4-methylpyrrolidin-3-yl]-1-(tetrahydro-2H-pyran-4-yl)-1H-pyrazolo[3,4-d]pyrimidin-4(5H)-one but substituting 6-[(3,4-trans)-1-benzyl-4-methylpyrrolidin-3-yl]-1-cyclobutyl-1,5-dihydro-4H-pyrazolo[3,4-d]pyrimidin-4-one provided the title compound. 400 MHz $^1$H NMR (CD$_3$OD) δ 8.03 (s, 1H), 5.39 (m, 1H), 3.79-3.38 (m, 4H), 3.08-2.71 (m, 4H), 2.43 (m, 2H), 1.92 (m, 2H), 1.22 (m, 3H). MS: (M+H m/z 464.2).

(b) 1-cyclobutyl-6-{(3,4-trans)-4-methyl-1-[(2-methylpyrimidin-5-yl)methyl]pyrrolidin-3-yl}-1,5-dihydro-4H-pyrazolo[3,4-d]pyrimidin-4-one

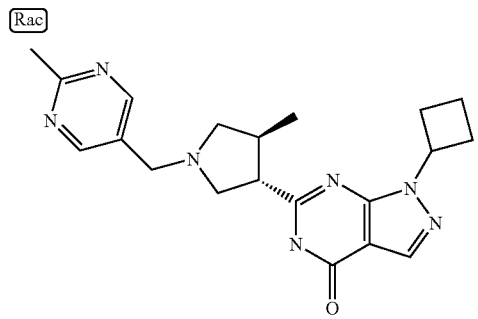

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 1-cyclobutyl-6-[(3,4-trans)-4-methylpyrrolidin-3-yl]-1H-pyrazolo[3,4-d]pyrimidin-4(5H)-one provided the title compound. 400 MHz $^1$H NMR (CDCl$_3$) δ 10.79 (brs, 1H), 8.63 (s, 2H), 8.04 (s, 1H), 5.28-5.22 (m, 1H), 3.68 (s, 2H), 3.24 (t, J=8.3 Hz, 1H), 3.04 (d, J=9.9 Hz, 1H), 2.89-2.87 (m, 1H), 2.80-2.67 (m, 5H), 2.51-2.38 (m, 3H), 2.03-1.81 (m, 4H), 1.18 (d, J=7.1 Hz, 3H). MS: (M+H m/z 480.2).

Example 84

6-[(3S,4S)-1-(2,1,3-benzothiadiazol-5-ylmethyl)-4-methylpyrrolidin-3-yl]-1-(tetrahydro-2H-pyran-4-yl)-1,5-dihydro-4H-pyrazolo[3,4-d]pyrimidin-4-one

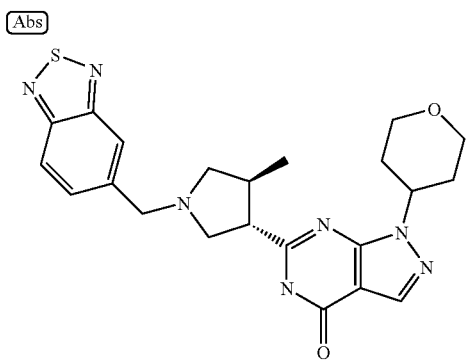

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting benzo[c][1,2,5]thiadiazole-5-carbaldehyde provided the title compound. 400 MHz $^1$H NMR (CDCl$_3$) δ 10.97 (brs, 1H), 8.02-8.00 (m, 2H), 7.86 (s, 1H), 7.77 (d, J=1.2 Hz, 1H), 4.81-4.75 (m, 1H), 4.12-4.06 (m, 2H), 3.96-3.92 (m, 1H), 3.81-3.78 (m, 1H), 3.60-3.52 (m, 2H), 3.38 (t, J=8.3 Hz, 1H), 3.03 (d, J=9.9 Hz, 1H), 2.88-2.85 (m, 1H), 2.68-2.63 (m, 1H), 2.47-2.45 (m, 1H), 2.37-2.28 (m, 2H), 2.04 (t, J=8.7 Hz, 1H), 1.90-1.80 (m, 2H), 1.21 (d, J=7.1 Hz, 3H). MS: (M+H m/z 452.1).

Example 85

6-[(3S,4S)-4-methyl-1-(quinoxalin-2-ylmethyl)pyrrolidin-3-yl]-1-tetrahydro-2H-pyran-4-yl)-1,5-dihydro-4H-pyrazolo[3,4-d]pyrimidin-4-one

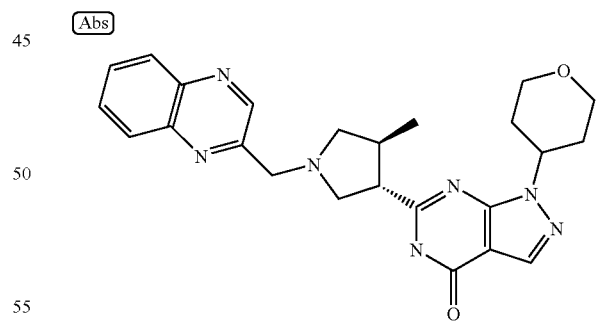

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting quinoxaline-2-carbaldehyde provided the title compound. 400 MHz $^1$H NMR (CDCl$_3$) δ 11.57 (brs, 1H), 8.89 (s, 1H), 8.26 (dd, J=8.3, 1.2 Hz, 1H), 8.08-8.05 (m, 2H), 7.78-7.70 (m, 2H), 4.82 (m, 1H), 4.32-4.28 (m, 1H), 4.13-4.08 (m, 2H), 4.00-3.96 (m, 1H), 3.63-3.55 (m, 2H), 3.44 (t, J=8.3 Hz, 1H), 3.26 (d, J=9.9 Hz, 1H), 2.93-2.91 (m, 1H), 2.70-2.69 (m, 1H), 2.39-2.31 (m, 2H), 2.25-2.23 (m, 1H), 2.04 (s, 1H), 1.92-1.84 (m, 2H), 1.23 (d, J=7.1 Hz, 3H). MS: (M+H m/z 446.2).

Example 86

6-[(3S,4S)-4-methyl-1-(quinolin-4-ylmethyl)pyrrolidin-3-yl]-1-(tetrahydro-2H-pyran-4-yl)-1,5-dihydro-4H-pyrazolo[3,4-d]pyrimidin-4-one

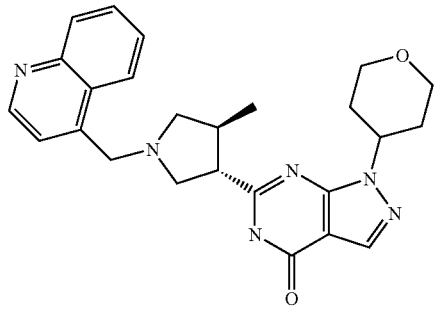

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting quinoline-4-carbaldehyde provided the title compound. 400 MHz $^1$H NMR (CDCl$_3$) δ 10.68 (brs, 1H), 8.83 (d, J=4.1 Hz, 1H), 8.25-8.22 (m, 1H), 8.12-8.08 (m, 1H), 7.98 (s, 1H), 7.75-7.72 (m, 1H), 7.54 (d, J=3.3 Hz, 1H), 7.36 (d, J=3.3 Hz, 1H), 5.21 (m, 1H), 4.77 (m, 1H), 4.13-4.06 (m, 3H), 3.59-3.52 (m, 2H), 3.32 (d, J=8.7 Hz, 1H), 3.03 (d, J=9.9 Hz, 1H), 2.88-2.86 (m, 1H), 2.72-2.69 (m, 1H), 2.36-2.28 (m, 3H), 2.04-2.00 (m, 1H), 1.89-1.84 (m, 2H), 1.20 (d, J=7.1 Hz, 3H). MS: (M+H m/z 445.1).

Example 87

6-[(3S,4S)-4-methyl-1-(pyridin-2-ylmethyl)pyrrolidin-3-yl]-1-(tetrahydro-2H-pyran-4-yl)-1,5-dihydro-4H-pyrazolo[3,4-d]pyrimidin-4-one

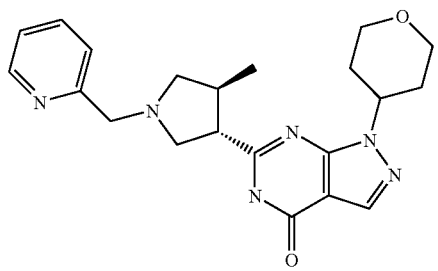

To a solution of 6-[(3S,4S)-4-methylpyrrolidin-3-yl]-1-(tetrahydro-2H-pyran-4-yl)-1H-pyrazolo[3,4-d]pyrimidin-4 (5H)-one hydrogen chloride (3.98 g) in dimethylformamide (60 mL) was added 2-pyridyl carbaldehyde (1.63 g) followed by acetic acid (1.34 mL) and sodium triacetoxy borohydride (4.99 g). The reaction mixture was stirred for 20 minutes at ambient temperature and quenched with 24 mL of 1 N NaOH solution. The reaction mixture was adjusted to pH 9 with saturated sodium bicarbonate solution, extracted 3× with ethyl acetate and dried with magnesium sulfate, filtered and concentrated to give 3.6 g of the title compound. The free base was dissolve in ethyl acetate and 25 mL of HCl/ethylacetate was added and stirred. The white solid was filtered and dried to provide 5.10 g of the title compound as a dihydrogen chloride salt. 400 MHz $^1$H NMR (CDCl$_3$) δ 8.64-8.63 (m, 1H), 8.03 (s, 1H), 7.72-7.67 (m, 1H), 7.43 (d, J=7.9 Hz, 1H), 7.21-7.18 (m, 1H), 4.85-4.75 (m, 1H), 4.14-4.05 (m, 3H), 3.80-3.76 (m, 1H), 3.63-3.54 (m, 2H), 3.47-3.42 (m, 1H), 3.10 (m, 1H), 2.87 (m, 1H), 2.66 (m, 1H), 2.46-2.28 (m, 3H), 2.14 (m, 1H), 1.93-1.84 (m, 2H), 1.20 (d, J=7.1 Hz, 3H). MS: (M+H m/z 495.2).

Example 88

(a) 5-amino-3-methyl-1-(tetrahydro-2H-pyran-4-yl)-1H-pyrazole-4-carbonitrile

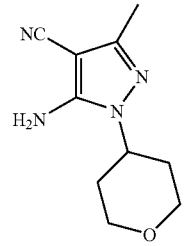

Following the procedure for the preparation of 5-amino-1-(2-methoxyphenyl)-1H-pyrazole-4-carbonitrile but substituting 1-(tetrahydro-2H-pyran-4-yl)hydrazine and 2-(1-methoxyethylidene)malononitrile provided the title compound. 400 MHz $^1$H NMR (CD$_3$OD) δ 4.20 (m, 1H), 4.05 (m, 2H), 3.50 (m, 2H), 2.18 (s, 3H), 2.09 (m, 2H), 1.77 (m, 2H). MS: (M+H m/z 207.0).

(b) 5-amino-3-methyl-1-(tetrahydro-2H-pyran-4-yl)-1H-pyrazole-4-carboxamide

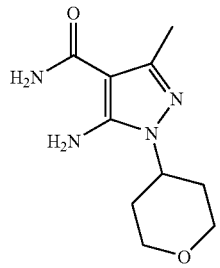

Following the procedure for the preparation of 5-amino-1-(2-methoxyphenyl)-1H-pyrazole-4-carboxamide but substituting 5-amino-3-methyl-1-(tetrahydro-2H-pyran-4-yl)-1H-pyrazole-4-carbonitrile provided the title compound. 400 MHz $^1$H NMR (CD$_3$OD) δ 4.20 (m, 1H), 4.05 (m, 2H), 3.50 (m, 2H), 2.18 (s, 3H), 2.09 (m, 2H), 1.77 (m, 2H). MS: (M+H m/z 225.0).

(c) 6-[(3S,4S)-1-benzyl-4-methylpyrrolidin-3-yl]-3-methyl-1-(tetrahydro-2H-pyran-4-yl)-1,5-dihydro-4H-pyrazolo[3,4-d]pyrimidin-4-one

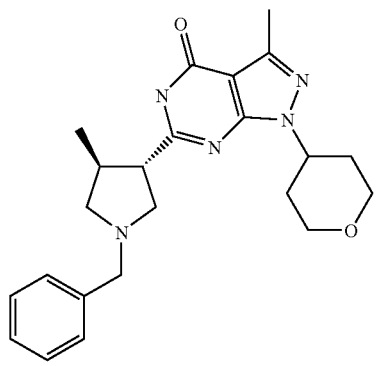

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-3-methyl-1-(tetrahydro-2H-pyran-4-yl)-1H-pyrazole-4-carboxamide and (3S,4S)-methyl-1-benzyl-4-methylpyrrolidine-3-carboxylate provided the title compound. 400 MHz $^1$H NMR (CDCl$_3$) δ 8.51-7.30 (m, 5H), 4.75-4.68 (m, 1H), 4.13-4.08 (m, 2H), 3.84-3.73 (m,1H), 3.63-3.48 (m, 2H), 3.40 (m,1 H), 3.10-2.78 (m, 2H), 2.55 (s, 3H), 2.50-2.24 (m, 3H), 1.87-1.80 (m, 2H), 0.61-1.41 (m, 3H), 1.19 (d, J=6.6 Hz, 3H). MS: (M$^+$H m/z=408.1).

Example 89

6-[(3S,4S)-1-(3-fluorobenzyl)-4-methylpyrrolidin-3-yl]-1-(tetrahydro-2H-pyran-4-yl)-1,5-dihydro-4H-pyrazolo[3,4-d]pyrimidin-4-one

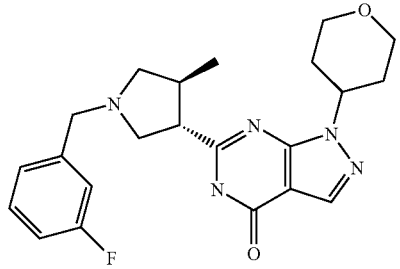

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 3-fluorobenzaldehyde provided the title compound. 400 MHz $^1$H NMR (CDCl$_3$) δ 8.02 (s,1H), 7.35-7.30 (m, 1H), 7.21-7.20 (m, 1H), 7.05 (d, J=9.5 Hz, 1H), 6.98-6.93 (m, 1H), 4.83-4.77 (m, 1H), 4.14-4.08 (m, 2H), 3.80-3.77 (m, 1H), 3.64-3.54 (m, 3H), 3.36 (t, J=8.8 Hz, 1H), 3.01 (d, J=9.9 Hz, 1H), 2.84-2.83 (m, 1H), 2.57 (m, 1H), 2.44-2.27 (m, 3H), 1.95-1.83 (m, 3H), 1.20 (d, J=7.1 Hz, 3H). MS: (M+H m/z 412.4).

Example 90

6-[(3S,4S)-1-(3,5-difluorobenzyl)-4-methylpyrrolidin-3-yl]-1-(tetrahydro-2H-pyran-4-yl)-1,5-dihydro-4H-pyrazolo[3,4-d]pyrimidin-4-one

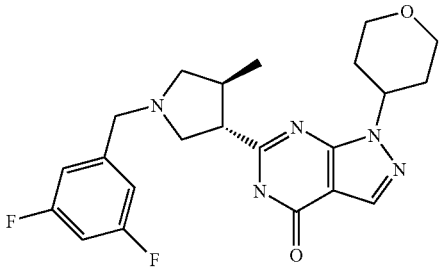

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 3,5-difluorobenzaldehyde provided the title compound. 400 MHz $^1$H NMR (CDCl$_3$) δ 8.03 (s, 1H), 6.93-6.90 (m, 2H), 6.73-6.69 (m, 1H), 4.81-4.80 (m, 1H), 4.14-4.10 (m, 2H), 3.79-3.67 (m, 2H), 3.62-3.55 (m, 2H), 3.30-3.26 (m, 1H), 3.10-3.07 (m, 1H), 2.95-2.92 (m, 1H), 2.83-2.79 (m, 1H), 2.26-2.53 (m, 1H), 2.38-2.32 (m, 2H), 2.18-2.14 (m, 1H), 1.91-1.85 (m, 2H), 1.18 (d, J=7.1 Hz, 3H). MS: (M+H m/z 430.4).

Example 91

6-{(3S,4S)-4-methyl-1-[4-(trifluoromethyl)benzyl]pyrrolidin-3-yl}-1-(tetrahydro-2H-pyran-4-yl)-1,5-dihydro-4H-pyrazolo[3,4-d]pyrimidin-4-one

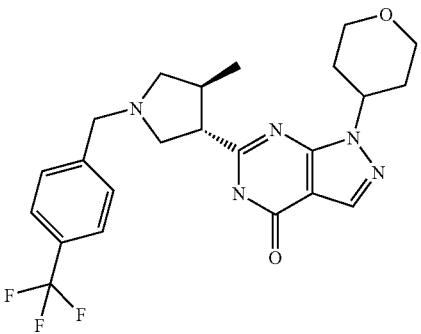

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 4-trifluoromethyl)benzaldehyde provided the title compound. 400 MHz $^1$H NMR (CDCl$_3$) δ 8.03 (s, 1H), 7.62-7.59 (m, 2H), 7.51-7.49

(m, 2H), 4.83-4.76 (m, 1H), 4.14-4.08 (m, 2H), 3.87-3.84 (m, 1H), 3.70-3.67 (m, 1H), 3.61-3.54 (m, 2H), 3.34 (t, J=8.3 Hz, 1H), 3.01 (d, J=9.9 Hz, 1H), 2.88-2.86 (m, 1H), 2.67-2.62 (m, 1H), 2.48-2.46 (m, 1H), 2.38-2.30 (m, 2H), 2.05-2.00 (m, 1H), 1.81-1.82 (m, 2H), 1.19 (d, J=7.1 Hz, 3H). MS: (M+H m/z 462.4).

Example 92

3-methyl-6-[(3S,4S)-4-methyl-1-(pyridin-3-ylmethyl)pyrrolidin-3-yl]-1-(tetrahydro-2H-pyran-4-yl)-1,5-dihydro-4H-pyrazolo[3,4-d]pyrimidin-4-one

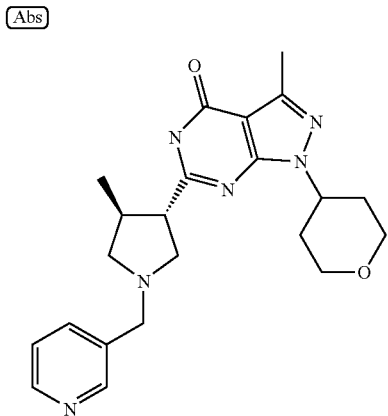

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 3-methyl-6-[(3S, 4S)-4-methylpyrrolidin-3-yl]-1-(tetrahydro-2H-pyran-4-yl)-1H-pyrazolo[3,4-d]pyrimidin-4(5H)-one and nicotinaldehyde provided the title compound. 400 MHz $^1$H NMR (CDCl$_3$) δ 8.53 (m, 2H), 7.83 (d, J=7.9 Hz, 1H), 7.36-7.33 (m, 1H), 4.74-4.68 (m, 1H), 4.12-4.07 (m, 2H), 3.79-3.76 (m, 1H), 3.68-3.65 (m, 1H), 3.59-3.52 (m, 2H), 3.47 (s, 1H), 3.34 (t, J=8.7 Hz, 1H), 2.99 (d, J=9.9 Hz, 1H), 2.82-2.80 (m, 1H), 2.61-2.57 (m, 1H), 2.54 (s, 3H), 2.42-2.28 (m, 2H), 1.95 (t, J=8.7 Hz, 1H), 1.87-1.78 (m, 2H), 1.19 (d, J=7.1 Hz, 3H). MS: (M+H m/z 409.2).

Example 93

(a) 3-methyl-6-[(3S,4S)-4-methylpyrrolidin-3-yl]-1-(tetrahydro-2H-pyran-4-yl)-1H-pyrazolo[3,4-d]pyrimidin-4(5H)-one

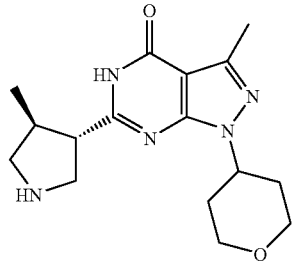

Following the procedure for the preparation of 6-[(3S,4S)-4-methylpyrrolidin-3-yl]-1-(tetrahydro-2H-pyran-4-yl)-1H-pyrazolo[3,4-d]pyrimidin-4(5H)-one but substituting 6-[(3S, 4S)-1-benzyl-4-methylpyrrolidin-3-yl]-3-methyl-1-(tetrahydro-2H-pyran-4-yl)-1,5-dihydro-4H-pyrazolo[3,4-d]pyrimidin-4-one provided the title compound. 400 MHz $^1$H NMR (CDCl$_3$) δ 4.85-4.81 (m, 1H), 4.08-4.04 (m, 2H), 3.61-3.55 (m, 2H), 3.31-3.28 (m, 3H), 2.84-2.82 (m, 1H), 2.60-2.53 (m, 2H), 2.49 (s, 3H), 2.29-2.25 (m, 2H), 1.85-1.81 (m, 2H), 1.12 (d, J=6.62 Hz, 3H). MS: (M$^+$H m/z=249.1).

(b) 3-methyl-6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one

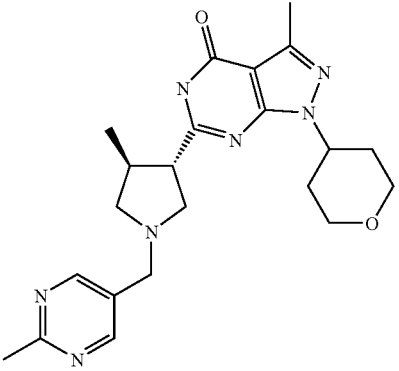

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 3-methyl-6-[(3S, 4S)-4-methylpyrrolidin-3-yl]-1-(tetrahydro-2H-pyran-4-yl)-1H-pyrazolo[3,4-d]pyrimidin-4(5H)-one provided the title compound. 400 MHz $^1$H NMR (CDCl$_3$) δ 8.63 (s, 2H), 4.74-4.68 (m, 1H), 4.11-4.08 (m, 2H), 3.74-3.63 (m, 2H), 3.60-3.52 (m, 2H), 3.28 (t, J=8.3 Hz, 1H), 3.03 (d, J=9.5 Hz, 1H), 2.85-2.83 (m, 1H), 2.71 (s, 3H), 2.65-2.61 (m, 1H), 2.53 (s, 3H), 2.48-2.29 (m, 2H), 1.98 (t, J=8.7 Hz, 1H), 1.87-1.80 (m, 3H), 1.19 (d, J=7.1 Hz, 3H). MS: (M+H m/z 424.2).

Example 94

6-{(3S,4S)-1-[(6-methoxypyridin-3yl)methyl]-4-methylpyrrolidin-3-yl}-3methyl-1-(tetrahyrdro-2H-pyran-4-yl)-1,5-dihydro-4H-pyrazolo[3,4-d]pyrimidin-4-one

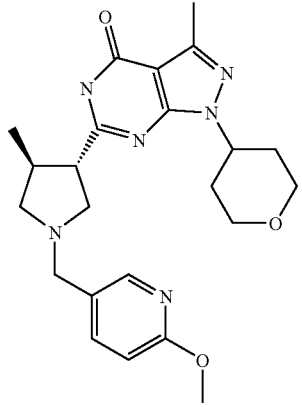

Following the procedure for the preparation of 6-{(3S,4S)-4-methyl-1-[(2-methylpyrimidin-5-yl)methyl]pyrrolidin-3- yl}-1-(tetrahydro-2H-pyran-4-yl)-1,5-dihydro-4H-pyrazolo[3,4-d]pyrimidin-4-one but substituting 3-methyl-6-[(3S,4S)-4-methylpyrrolidin-3-yl]-1-(tetrahydro-2H-pyran-4-yl)-1H-pyrazolo[3,4-d]pyrimidin-4(5H)-one and 6-methoxynicotinaldehyde provided the title compound. 400 MHz $^1$H NMR (CDCl$_3$) δ 8.03 (d, J=2.1 Hz, 1H), 7.69 (dd, J=8.7, 2.1 Hz, 1H), 6.78 (d, J=9.1 Hz, 1H), 4.74-4.68 (m, 1H), 4.13-4.07 (m, 2H), 3.89 (s, 3H), 3.70-3.67 (m, 1H), 3.59-3.51 (m, 2H), 3.32 (t, J=8.7 Hz, 1H), 2.97 (d, J=9.9 Hz, 1H), 2.79-2.77 (m, 1H), 2.54 (s, 3H), 2.53-2.50 (m, 1H), 2.41-2.29 (m, 2H), 1.92-1.78 (m, 3H), 1.30-1.18 (m, 2H), 10.86 (t, J=76.6 Hz, 3H). MS: (M+H m/z 439.2).

Example 95

6-{(3S,4S)-4-methyl-1-[(6-methylpyridin-2-yl)methyl]pyrrolidin-3-yl}-1-(tetrahydro-2H-pyran-4-yl)-1,5-dihydro-4H-pyrazolo[3,4-d]pyrimidin-4-one

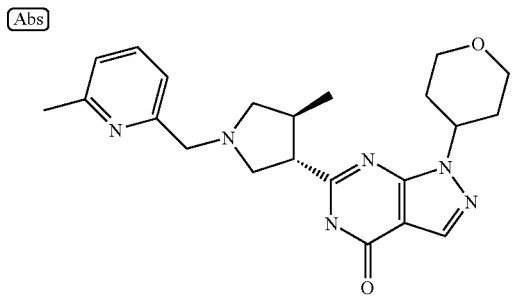

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 6-methylpicolinaldehyde provided the title compound. 400 MHz $^1$H NMR (CDCl$_3$) δ 8.02 (s, 1H), 7.57 (t, J=7.7 Hz, 1H), 7.20 (d, J=7.9 Hz, 1H), 7.03 (d, J=7.5 Hz, 1H), 4.83-4.77 (m, 1H), 4.13-4.08 (m, 2H), 3.99-3.95 (m, 1H), 3.72-3.69 (m, 1H), 3.62-3.54 (m, 2H), 3.42 (t, J=8.3 Hz, 1H), 3.06 (d, J=9.9 Hz, 1H), 2.85-2.83 (m, 1H), 2.64-2.57 (m, 1H), 2.55 (s, 3H), 2.44-2.29 (m, 3H), 2.08-2.03 (m, 1H), 1.91-1.82 (m, 2H), 1.20 (t, J=7.1 Hz, 3H). MS: (M+H m/z 409.1).

Example 96

6-[(3S,4S)-1-(4-fluorobenzyl)-4-methylpyrrolidin-3-yl]-1-(tetrahydro-2H-pyran-4-yl)-1,5-dihydro-4H-pyrazolo[3,4-d]pyrimidin-4-one

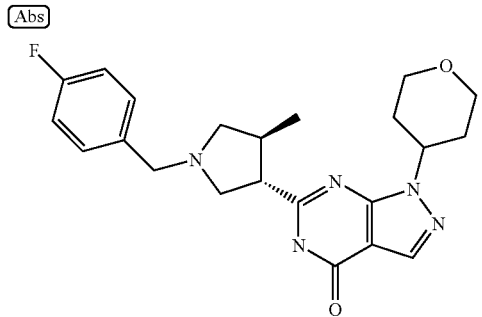

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 4-fluorobenzaldehyde provided the title compound. 400 MHz $^1$H NMR (CDCl$_3$) δ 8.02 (s, 1H), 7.36-7.33 (m, 2H), 7.05-7.01 (m, 2H), 4.82-4.77 (m, 1H), 4.14-4.09 (m, 2H), 3.79-3.76 (m, 1H), 3.62-3.54 (m, 3H), 3.34 (t, J=8.3 Hz, 1H), 2.99 (d, J=9.9 Hz, 1H), 2.85-2.83 (m, 1H), 2.60-2.55 (m, 1H), 2.45-2.30 (m, 3H), 1.99-1.82 (m, 3H), 1.20 (d, J=7.1 Hz, 3H). MS: (M+H m/z 412.1).

Example 97

(a) 6-[(3,4-trans)-1-benzyl-4-ethylpyrrolidin-3-yl]-1-(tetrahydro-2H-pyran-4-yl)-1,5-dihydro-4H-pyrazolo[3,4-d]pyrimidin-4-one Following the procedure for the preparation of 6-[(3,4-trans)-1-benzyl-4-methylpyrrolidin-3-yl]-1-(tetrahydro-2H-pyran-4-yl)-1,5-dihydro-4H-pyrazolo[3,4-d]pyrimidin-4-one but substituting (3,4-trans)-ethyl 1-benzyl-4-methylpyrrolidine-3-carboxylate provided the title compound. 400 MHz $^1$H NMR (CDCl$_3$) δ 8.02 (s, 1H), 7.40-7.26 (m, 5H), 4.78 (m, 1H), 4.12-4.09 (m, 2H), 3.82-3.804 (m, 1H), 3.65-3.54 (m, 3H), 3.35 (t, J=8.3 Hz, 1H), 2.98 (d, J=9.9 Hz, 1H), 2.89-2.86 (m, 1H), 2.48-2.32 (m, 3H), 2.20 (m, 1H), 1.95-1.87 (m, 2H), 1.63-1.58 (m, 2H), 1.50-1.49 (m, 1H), 0.93 (t, J=7.1 Hz, 3H). MS: (M+H m/z 408.1).

(b) 6-[(3S,4S)-1-benzyl-4-ethylpyrrolidin-3-yl]-1-(tetrahydro-2H-pyran-4-yl)-1,5-pyrazolo[3,4-d]pyrimidin-4-one

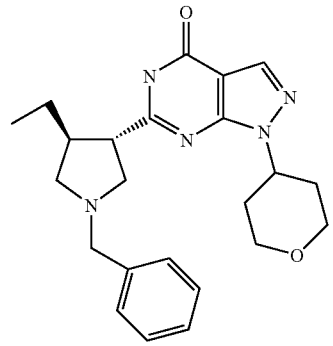

The 6-[(3,4-trans)-1-benzyl-4-ethylpyrrolidin-3-yl]-1-(tetrahydro-2H-pyran-4-yl)-1,5-dihydro-4H-pyrazolo[3,4-d]pyrimidin-4-one racemate was separated on Chiralcel OJ-H chiral HPLC column, Mobile Phase 80/20 CO$_2$/MeOH, T$_R$=3.27, to provide the enantiomer. Analytical: AD column, Mobile Phase 85/15 Heptane/EtOH, T$_R$=12.896. 400 MHz $^1$H NMR (CDCl$_3$) δ 8.02 (s, 1H), 7.40-7.26 (m, 5H), 4.78 (m, 1H), 4.12-4.09 (m, 2H), 3.82-3.804 (m, 1H), 3.65-3.54 (m, 3H), 3.35 (t, J=8.3 Hz, 1H), 2.98 (d, J=9.9 Hz, 1H), 2.89-2.86 (m, 1H), 2.48-2.32 (m, 3H), 2.20 (m, 1H), 1.95-1.87 (m, 2H), 1.63-1.58 (m, 2H), 1.50-1.49 (m, 1H), 0.93 (t, J=7.1 Hz, 3H). MS: (M+H m/z 408.1).

Example 98

6-[(3S,4S)-1-(2-fluorobenzyl)-4-methylpyrrolidin-3-yl]-1-(tetrahydro-2H-pyran-4-yl)-1,5-dihydro-4H-pyrazolo[3,4-d]pyrimidin-4-one

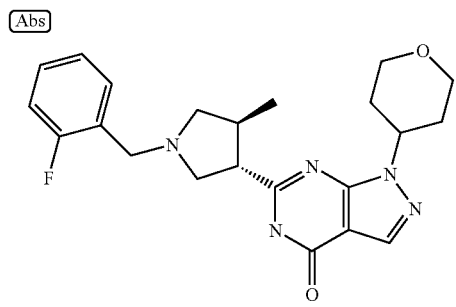

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 2-fluorobenzaldehyde provided the title compound. 400 MHz $^1$H NMR (CD$_3$OD) δ 7.98 (s, 1H), 7.47-7.42 (m, 1H), 7.33-7.26 (m, 2H), 7.18-7.07 (m, 1H), 4.08-4.04 (m, 2H), 3.85 (s, 2H), 3.69-3.56 (m, 3H), 3.20-2.93 (m, 4H), 2.69-2.62 (m, 1H), 2.40-2.19 (m, 3H), 1.88-1.85 (m, 2H), 1.14 (d, J=6.6 Hz, 3H). MS: (M+H m/z 412.1).

Example 99

6-{(3S,4S)-4-methyl-1-[2-(trifluoromethyl)benzyl]pyrrolidin-3-yl}-1-(tetrahydro-2H-pyran-4-yl)-1,5-dihydro-4H-pyrazolo[3,4-d]pyrimidin-4-one

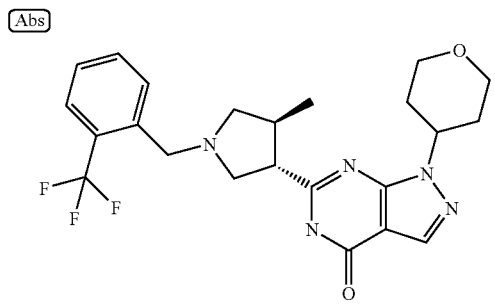

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 2-(trifluoromethyl)benzaldehyde provided the title compound. 400 MHz $^1$H NMR (CDCl$_3$) δ 10.58 (brs, 1H), 8.01 (s, 1H), 7.79-7.76 (m, 1H), 7.64-7.58 (m, 2H), 7.37-7.34 (m, 1H), 4.83-4.76 (m, 1H), 4.14-4.08 (m, 2H), 3.88 (m, 2H), 3.62-3.54 (m, 2H), 3.39 (t, J=8.3 Hz, 1H), 3.02-2.97 (m, 1H), 2.85 (m, 1H), 2.66 (m, 1H), 2.44-2.27 (m, 3H), 2.06-2.03 (m, 1H), 1.91-1.83(m,2H), 1.21 (d,J=7.1 Hz, 3H). MS: (M+H m/z 462.1).

Example 100

6-[(3S,4S)-1-(2,4-difluorobenzyl)-4-methylpyrrolidin-3-yl]-1-(tetrahydro-2H-pyran-4-yl)-1,5-dihydro-4H-pyrazolo[3,4-d]pyrimidin-4-one

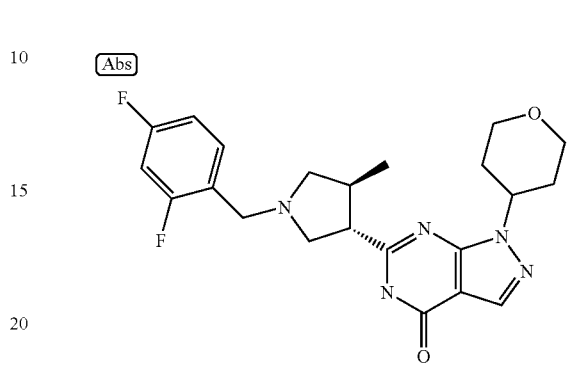

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 2,4-difluorobenzaldehyde provided the title compound. 400 MHz $^1$H NMR (CDCl$_3$) δ 8.01 (s, 1H), 7.40-7.38 (m, 2H), 6.90-6.79 (m, 2H), 4.81-4.77 (m, 2H), 4.14-4.08 (m, 2H), 3.88 (m, 2H), 3.62-3.54 (m, 2H), 3.32 (t, J=8.7 Hz, 1H), 3.02 (d, J=9.5 Hz, 1H), 2.86-2.83 (m, 1H), 2.65 (m, 1H), 2.43-2.20 (m, 3H), 2.00-1.83 (m, 2H), 1.21 (d, J=6.6 Hz, 3H). MS: (M+H m/z 430.2).

Example 101

6-[(3S,4S)-1-(4-methoxybenzyl)-4-methylpyrrolidin-3-yl]-1-(tetrahydro-2H-pyran-4-yl)-1,5-dihydro-4H-pyrazolo[3,4-d]pyrimidin-4-one

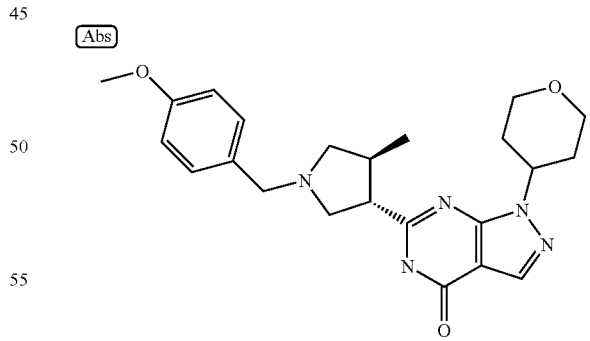

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 4-methoxybenzaldehyde provided the title compound. 400 MHz $^1$H NMR (CDCl$_3$) δ 8.01 (s, 1H), 7.29 (d, J=8.3 Hz, 2H), 6.87 (d, J=8.7 Hz, 2H), 4.82-4.08 (m, 1H), 4.13-4.08 (m, 2H), 3.84-3.75 (m, 4H), 3.61-3.51 (m, 3H), 3.35 (t, J=8.7 Hz, 1H), 2.97 (d, J=9.9 Hz, 1H), 2.82-2.80 (m, 1H), 2.53-2.49 (m, 1H), 2.42-2.30 (m, 3H), 1.95-1.82 (m, 3H), 1.18 (d, J=7.1 Hz, 3H).

Example 102

(a) 5-amino-1-(tetrahydro-2H-thiopyran-4-yl)-1H-pyrazole-4-carbonitrile

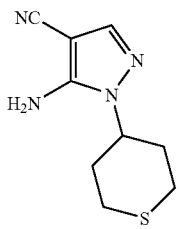

Following the procedure for the preparation of 5-amino-1-(2-methoxyphenyl)-1H-pyrazole-4-carbonitrile but substituting 1-(tetrahydro-2H-thiopyran-4-yl)hydrazine provided the title compound. 400 MHz $^1$H NMR (CDCl$_3$) δ 7.44 (s, 1H), 4.71 (s, 2H), 3.84-3.76 (m, 1H), 2.80-2.63 (m, 4H), 2.24-2.10 (m, 4H). MS: (M+H m/z 209.1).

(b) 5-amino-1-(tetrahydro-2H-thiopyran-4-yl)-1H-pyrazole-4-carboxamide

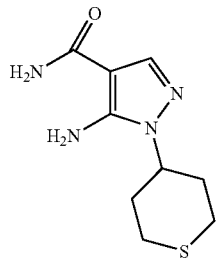

Following the procedure for the preparation of 5-amino-1-(2-methoxyphenyl)-1H-pyrazole-4-carboxamide but substituting 5-amino-1-(tetrahydro-2H-thiopyran-4-yl)-1H-pyrazole-4-carbonitrile provided the title compound. 400 MHz $^1$H NMR (CDCl$_3$) δ 7.67 (s, 1H), 4.09-3.97 (m, 1H), 2.89-2.82 (m, 2H), 2.72-2.68 (m, 2H), 2.15-2.10 (m, 4H). MS: (M+H m/z 227.1).

(c) 6-[(3S,4S)-1-benzyl-4-methylpyrrolidin-3-yl]-1-(tetrahydro-2H-thiopyran-4-yl)-1,5-dihydro-4H-pyrazolo[3,4-d]pyrimidin-4-one

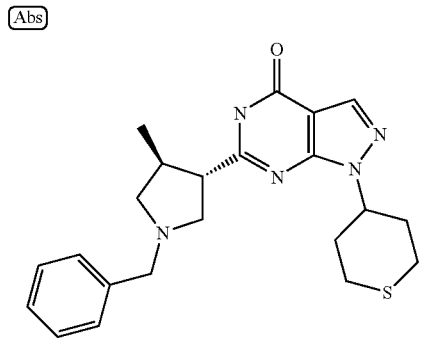

Following the procedure for the preparation of 6-[(3,4-trans)-1-benzyl-4-methylpyrrolidin-3-yl]-1-(2-methoxyphenyl)-1,5-dihydro-4H-pyrazolo[3,4-d]pyrimidin-4-one but substituting 5-amino-1-(tetrahydro-2H-thiopyran-4-yl)-1H-pyrazole-4-carboxamide and (3S,4S)-methyl-1-benzyl-4-methylpyrrolidine-3-carboxylate provided the title compound. 400 MHz $^1$H NMR (CDCl$_3$) δ 8.02 (s, 1H), 7.41-7.26 (m, 5H), 4.60-4.53 (m, 1H), 3.86-3.83 (m, 1H), 3.65 (m, 1H), 3.41-3.37 (m, 1H), 3.02 (m, 1H), 2.94-2.75 (m, 4H), 2.60-2.31 (m, 3H), 2.25-2.16 (m, 2H), 1.99-1.94 (m, 1H), 1.62 (m, 2H), 1.20 (t, J=7.1 Hz, 3H). MS: (M+H m/z 410.2).

Example 103

6-[(3S,4S)-1-(2-methoxybenzyl)-4-methylpyrrolidin-3-yl]-1-(tetrahydro-2H-pyran-4-yl)-1,5-dihydro-4H-pyrazolo[3,4-d]pyrimidin-4-one

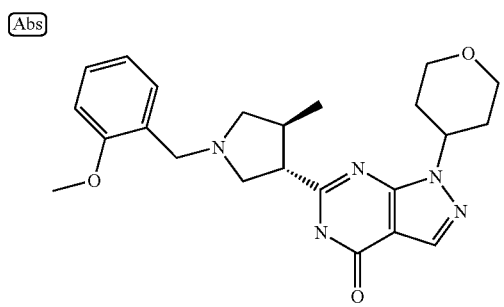

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyano borohydride and 2-methoxybenzaldehyde provided the title compound. 400 MHz $^1$H NMR (CDCl$_3$) δ 8.00 (s, 1H), 7.29-7.22 (m, 2H), 6.92-6.88 (m, 2H), 4.83-4.75 (m, 1H), 4.14-4.08 (m, 2H), 3.93 (s, 3H), 3.76-3.69 (m, 2H), 3.62-3.54 (m, 2H), 3.34 (t, J=8.7 Hz, 1H), 3.01 (d, J=9.5 Hz, 1H), 2.78 (m, 1H), 2.56 (m, 1H), 2.41-2.27 (m, 3H), 1.92-1.82 (m, 3H), 1.18 (d, J=7.1 Hz, 3H). MS: (M+H m/z 424.1).

Example 104

6-[(3S,4S)-1-(3-methoxybenzyl)-4-methylpyrrolidin-3-yl]-1-(tetrahydro-2H-pyran-4-yl)-1,5-dihydro-4H-pyrazolo[3,4-d]pyrimidin-4-one

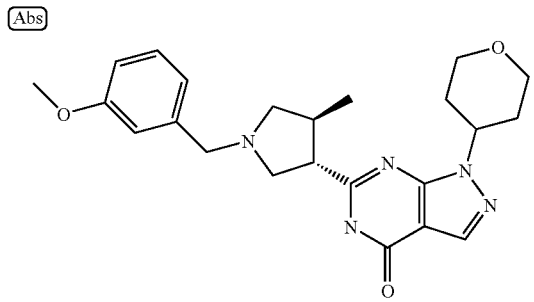

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo

[3,4-d]pyrimidin-4-one but substituting sodium cyanoborohydride and 3-methoxybenzaldehyde provided the title compound. 400 MHz $^1$H NMR (CDCl$_3$) δ 8.02 (s, 1H), 7.27-7.21 (m, 1H), 6.96-6.92 (m, 2H), 6.81 (d, J=7.1 Hz, 1H), 4.82-4.76 (m, 1H), 4.14-4.08 (m, 2H), 3.85 (s, 3H), 3.79 (s, 1H), 3.62-3.54 (m, 3H), 3.39 (t, J=8.7 Hz, 1H), 3.00 (d, J=10.3 Hz, 1H), 2.81 (m, 1H), 2.53 (m, 1H), 2.42-2.28 (m, 3H), 1.94-1.82 (m, 3H), 1.20 (d, J=7.1 Hz, 3H). MS: (M+H m/z 424.1).

Example 105

6-{(3S,4S)-4-methyl-1-[3-(trifluoromethyl)benzyl]pyrrolidin-3-yl}-1-(tetrahydro-2H-pyran-4-yl)-1,5-dihydro-4H-pyrazolo[3,4-d]pyrimidin-4-one

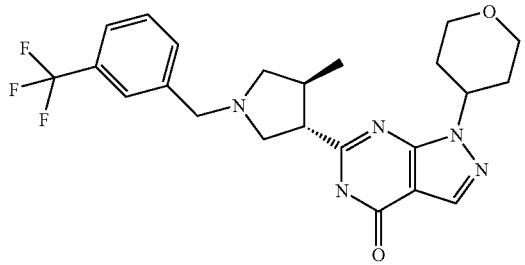

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 3-(trifluoromethyl)benzaldehyde provided the title compound. 400 MHz $^1$H NMR (CDCl$_3$) δ 8.02 (s, 1H), 7.68-7.63 (m, 1H), 7.55-7.51 (m, 3H), 4.84-4.76 (m, 1H), 4.14-4.08 (m, 2H), 3.87-3.84 (m, 1H), 3.71-3.69 (m, 1H), 3.62-3.54 (m, 2H), 3.36 (t, J=8.3 Hz, 1H), 3.01 (m, 1H), 2.86 (m, 1H), 2.63-2.60 (m, 1H), 2.50-2.27 (m, 3H), 1.98-1.83 (m, 3H), 1.21 (d, J=6.6 Hz, 3H). MS: (M+H m/z 462.1).

Example 106

6-[(3S,4S)-1-(26-difluorobenzyl)-4-methylpyrrolidin-3-yl]-1-(tetrahydro-2H-pyran-4-yl)-1,5-dihydro-4H-pyrazolo[3,4-d]pyrimidin-4-one

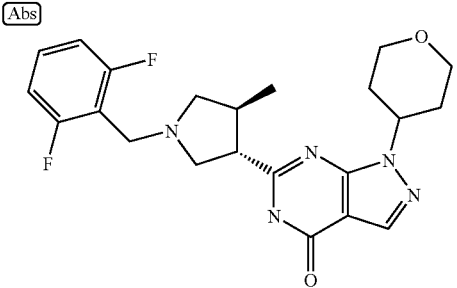

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting sodium cyanoborohydride and 2,6-difluorobenzaldehyde provided the title compound. 400 MHz $^1$H NMR (CDCl$_3$) δ 8.00 (s, 1H), 7.30-7.22 (m, 1H), 6.96-6.89 (m, 2H), 4.83-4.75 (m, 1H), 4.13-4.08 (m, 2H), 3.91 (s, 2H), 3.62-3.54 (m, 2H), 3.34 (t, J=8.3 Hz, 1H), 3.06 (d, J=9.5 Hz, 1H), 2.80 (m, 1H), 2.66 (m, 1H), 2.40-2.27 (m, 3H), 1.99 (m, 1H), 1.91-1.83 (m, 2H), 1.16 (d, J=7.1 Hz, 3H). MS: (M+H m/z 430.1).

Example 107

(a) 6-[(3S,4S)-4-ethylpyrrolidin-3-yl]-1-(tetrahydro-2H-pyran-4-yl)-1H-pyrazolo[3,4-d]pyrimidin-4(5H)-one

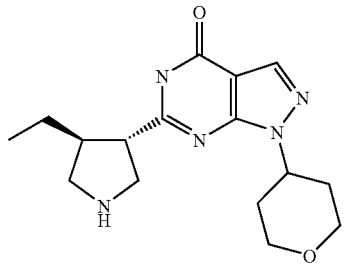

Following the procedure for the preparation of 6-[(3S,4S)-4-methylpyrrolidin-3-yl]-1-(tetrahydro-2H-pyran-4-yl)-1H-pyrazolo[3,4-d]pyrimidin-4(5H)-one but substituting 6-[(3S,4S)-1-benzyl-4-ethylpyrrolidin-3-yl]-1-(tetrahydro-2H-pyran-4-yl)-1,5-dihydro-4H-pyrazolo[3,4-d]pyrimidin-4-one provided the title compound. 400 MHz $^1$H NMR (CD$_3$OD) δ 8.02 (s, 1H), 4.97 (m, 1H), 4.09-4.06 (m, 2H), 3.78-3.58 (m, 4H), 3.34-3.34 (m, 1H), 3.16-3.11 (m, 1H), 2.68 (d, J=8.7 Hz, 1H), 2.63 (m, 1H), 2.32-2.27 (m, 2H), 1.90-1.87 (m, 2H), 1.69 (m, 1H), 1.57 (m, 1H), 0.97 (t, J=7.5 Hz, 3H). MS: (M+H m/z 318.2).

(b) 6-{(3S,4S)-4-ethyl-1-[(5-methylpyrazin-2-yl)methyl]pyrrolidin-3-yl}-1-(tetrahydro-2H-pyran-4-yl)-1,5-dihydro-4H-pyrazolo[3,4-d]pyrimidin-4-one

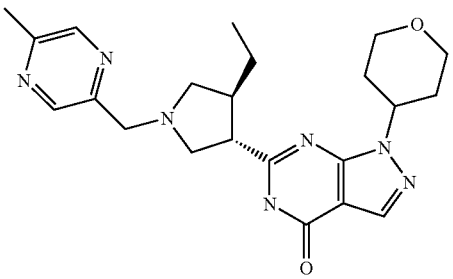

To a solution of 6-[(3S,4S)-4-ethylpyrrolidin-3-yl]-1-(tetrahydro-2H-pyran-4-yl)-1H-pyrazolo[3,4-d]pyrimidin-4(5H)-one (4.4 g) in dimethylformamide (62 mL) was added acetic acid (2.4 mL), 5-methylpyrazine-2-carbaldehyde (2 g) and sodium triacetoxyborohydride (5.27 g). The reaction mixture stirred for 2 h at ambient temperature and was carefully quenched with saturated sodium bicarbonate solution, extracted 3× with methylene chloride, dried with magnesium sulfate, filtered and concentrated. Purification via Biotage MPLC chromatography eluting with 1-4% methanolmethylene chloride/0.5% saturated ammonium hydroxide provided the title compound (3.9 g). 400 MHz $^1$H NMR (CDCl$_3$) δ 8.52-8.48 (m, 1H), 8.38 (s, 1H), 8.02 (s, 1H), 4.81-4.75 (m, 1H), 4.11-4.01 (m, 3H), 3.79-3.75 (m, 1H), 3.60-3.53 (m, 2H), 3.40-3.32 (m, 1H), 3.10-3.08 (m, 1H), 2.94 (m, 1H), 2.63-2.57 (m, 1H), 2.53 (d, J=7.5 Hz, 1H), 2.37-2.18 (m, 4H), 1.90-1.83 (m, 2H), 1.67-1.60 (m, 1H), 1.54-1.47 (m, 1H), 0.95-0.92 (m, 3H). MS: (M+H m/z 424.2).

Example 108

6-{(3S,4S)-4-ethyl-1-[(6-methoxypyridin-3-yl)methyl]pyrrolidin-3-yl}-1-(tetrahydro-2H-pyran-4-yl)-1,5-dihydro-4H-pyrazolo[3,4-d]pyrimidin-4-one

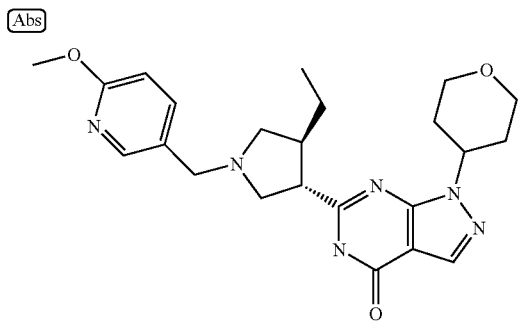

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-[(3S,4S)-4-ethylpyrrolidin-3-yl]-1-(tetrahydro-2H-pyran-4-yl)-1H-pyrazolo[3,4-d]pyrimidin-4(5H)-one hydrogen chloride, sodium cyanoborohydride and 6-methoxynicotinaldehyde provided the title compound. 400 MHz $^1$H NMR (CDCl$_3$) δ 8.04 (d, J=2.1 Hz, 1H), 8.02 (s, 1H), 7.73-7.71 (m, 1H), 6.78 (d, J=8.7 Hz, 1H), 4.80-4.75 (m, 1H), 4.12-4.10 (m, 2H), 3.92-3.90 (m, 3H), 3.72-3.70 (m, 1H), 3.61-3.54 (m, 3H), 3.32 (t, J=8.3 Hz, 1H), 2.99 (m, 1H), 2.91 (m, 1H), 2.41 (m, 1H), 2.40-2.28 (m, 2H), 2.21 (m, 1H), 1.95 (m, 1H), 1.91-1.83 (m, 2H), 1.65-1.45 (m, 2H), 0.92 (t, J=7.5 Hz, 3H). MS: (M+H m/z 439.2).

Example 109

6-[(3S,4S)-4-ethyl-1-(pyridin-2-ylmethyl)pyrrolidin-3-yl]-1-(tetrahydro-2H-pyran-4-yl)-1,5-dihydro-4H-pyrazolo[3,4-d]pyrimidin-4-one

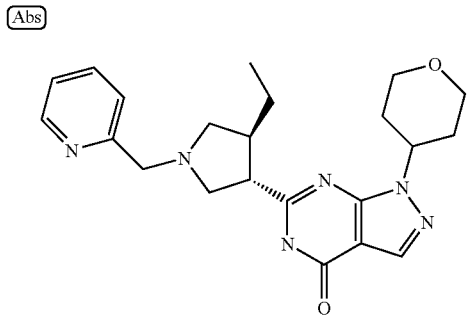

To a solution of 6-[(3S,4S)-4-ethylpyrrolidin-3-yl]-1-(tetrahydro-2H-pyran-4-yl)-1H-pyrazolo[3,4-d]pyrimidin-4(5H)-one hydrogen chloride (51 mg) in acetonitrile (1 mL) was added potassium carbonate (88 mg) and 2-(bromomethyl)pyridine hydrogen bromide (40 mg) and the reaction mixture was heated at reflux for 72 h in a sealed vial. The reaction mixture was concentrated onto silica and purified via CombiFlash flash chromatography to provide the title compound. 400 MHz $^1$H NMR (CDCl$_3$) δ 11.50 (brs, 1H), 8.63 (dd, J=1.7, 0.83, Hz, 1H), 8.02 (s, 1H), 7.70-7.67 (m, 1H), 7.40 (d, J=7.9 Hz, 1H), 7.20-7.16 (m, 1H), 4.79-4.77 (m, 1H), 4.12-4.02 (m, 3H), 3.75-3.72 (m, 1H), 3.61-3.53 (m, 2H), 3.39 (t, J=7.9 Hz, 1H), 3.07 (d, J=9.9 Hz, 1H), 2.92-2.90 (m, 1H), 2.37-2.12 (m, 4H), 1.91-1.83 (m, 2H), 1.65-1.60 (m, 1H), 1.54-1.49 (m, 1H), 0.94 (t, J=7.1 Hz, 3H). MS: (M+H m/z 409.1).

Example 110

6-[(3S,4S)-4-ethyl-1-(quinoxalin-2-ylcarbonyl)pyrrolidin-3-yl]-1-(tetrahydro-2H-pyran-4-yl)-1,5-dihydro-4H-pyrazolo[3,4-d]pyrimidin-4-one

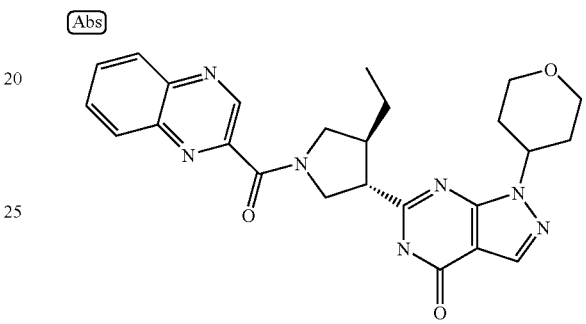

To a solution of 6-[(3S,4S)-4-ethylpyrrolidin-3-yl]-1-(tetrahydro-2H-pyran-4-yl)-1H-pyrazolo[3,4-d]pyrimidin-4 (5H)-one hydrogen chloride (73 mg) in dicloromethane (2 mL) was added triethylamine (62 mg) and 2-quinoxaloyl-chloride (40 mg) at 0° C. The reaction mixture was warmed to ambient temperature and stirred for 18 h. The reaction mixture was quenched with saturated sodium bicarbonate, extracted with methylene chloride, dried with magnesium sulfate, filtered and concentrated. Purification via CombiFlash flash chromatography eluting with 24% MeOH/methylene chloride provided the title compound. 400 MHz $^1$H NMR (CDCl$_3$) δ 12.78-12.62 (m, 1H), 9.41 (d, J=7.5, Hz, 1H), 8.18-8.00 (m, 3H), 7.87-7.73 (m, 2H), 4.84-4.81 (m, 1H), 4.55-3.86 (m, 6H), 3.61-3.53 (m, 2H), 3.38-3.31 (m, 1H), 2.75 (m, 1H), 2.39-2.34 (m, 2H), 1.93-1.89 (m, 2H), 1.58-1.56 (m, 1H), 1.63-1.50 (m, 1H), 1.01-0.88 (m, 3H). MS: (M+H m/z 474.2).

Example 111

6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one

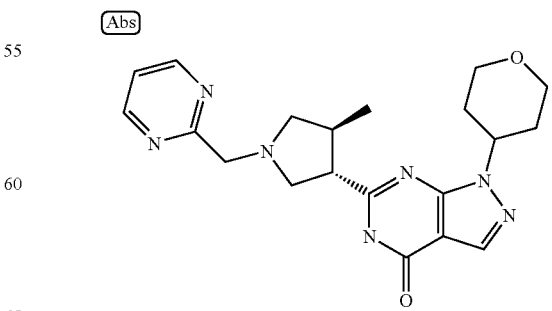

To a solution of 6-[(3S,4S)-4-methylpyrrolidin-3-yl]-1-(tetrahydro-2H-pyran-4-yl)-1H-pyrazolo[3,4-d]pyrimidin-4

(5H)-one hydrogen chloride (7.75 g) (see preparation in step (a) of Example 73) in dimethylformamide (115 mL) was added iron triflate (900 mg), 2-(chloromethyl)pyrimidine hydrogen chloride (4.5 g), and cesium carbonate (22.2 g) and the reaction mixture was heated at 60° C. for 24 h. The reaction mixture was concentrated onto silica gel and purified by flash chromatography eluting with 0-15% methanoylethyl acetate/1% saturated ammonium hydroxide to provide the title compound (6 g). 400 MHz $^1$H NMR (CDCl$_3$) δ 12.30 (brs, 1H), 8.63 (d, J=5.0, Hz, 2H), 8.03 (s, 1H). 7.20 (d, J=5.0, Hz, 1H), 4.84-4.79 (m, 1H), 4.30-4.27 (m, 1H), 4.14-4.08 (m, 2H), 3.87-3.82 (m, 1H), 3.63-3.55 (m, 2H), 3.47 (t, J=7.9 Hz, 1H), 3.29 (d, J=9.9 Hz, 1H), 2.88-2.86 (m, 1H), 2.60-2.56 (m, 1H), 2.46-2.24 (m, 4H), 1.93-1.84 (m, 2H), 1.24 (t, J=7.1 Hz, 3H). MS: (M+H m/z 396.2).

Example 112

2-({(3S,4S)-3-ethyl-4-[4-oxo-1-(tetrahydro-2H-pyran-4-yl)-45-dihydro-1H-pyrazolo[3,4-d]pyrimidin-6-yl]pyrrolidin-1-yl}methyl)benzonitrile

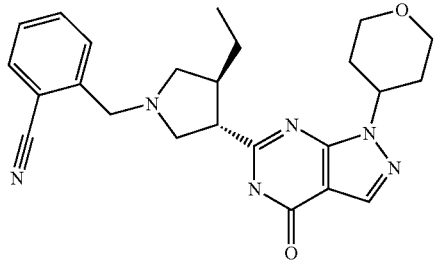

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-[(3S,4S)-4-ethylpyrrolidin-3-yl]-1-(tetrahydro-2H-pyran-4-yl)-1H-pyrazolo[3,4-d]pyrimidin-4(5H)-one hydrogen chloride, sodium cyanoborohydride and 2-formylbenzonitrile provided the title compound. 400 MHz $^1$H NMR (CDCl$_3$) δ 11.68 (brs, 1H), 8.01 (s, 1H), 7.68-7.58 (m, 3H), 7.40-7.36 (m, 1H), 4.91 (s, 1H), 4.82-4.76 (m, 1H), 4.12-4.10 (m, 2H), 3.94 (m, 1H), 3.61-6.55 (m, 2H), 3.37 (m, 1H), 3.03-2.94 (m, 2H), 2.66 (m, 1H), 2.41-2.23 (m, 3H), 2.09 (m, 1H), 1.91-1.84 (m, 2H), 1.66-1.49 (m, 2H), 0.93 (t, J=7.5 Hz, 3H). MS: (M+H m/z 433.2).

Example 113

3-({(3S,4S)-3-ethyl-4-[4-oxo-1-(tetrahydro-2H-pyran-4-yl)-4,5-dihydro-1H-pyrazolo[3,4-d]pyrimidin-6-yl]pyrrolidin-1-yl}methyl)benzonitrile

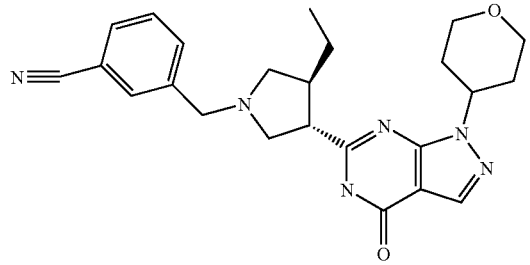

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-[(3S,4S)-4-ethylpyrrolidin-3-yl]-1-(tetrahydro-2H-pyran-4-yl)-1H-pyrazolo[3,4-d]pyrimidin-4(5H)-one hydrogen chloride, sodium cyanoborohydride and 3-formylbenzonitrile provided the title compound. 400 MHz $^1$H NMR (CDCl$_3$) δ 8.01 (s, 1H), 7.73-7.41 (m, 4H), 4.79 (m, 1H), 4.72 (s, 1H), 4.12-4.09 (m, 2H), 3.82-3.70 (m, 2H), 3.61-3.54 (m, 2H), 3.27 (t, J=8.3 Hz, 1H), 3.02-2.97 (m, 2H), 2.71-2.70 (m, 1H), 2.37-2.30 (m, 2H), 2.20-2.14 (m, 1H), 1.90-1.87 (m, 2H), 1.61-1.60 (m, 1H), 1.51-1.49 (m, 1H), 0.91 (t, J=7.5 Hz, 3H). MS: (M+H m/z 433.2).

Example 114

4-({(3S,4S)-3-ethyl-4-[4-oxo-1-(tetrahydro-2H-pyran-4-yl)-45-dihydro-1H-pyrazolo[3,4-d]pyrimidin-6-yl]pyrrolidin-1-yl}methyl)benzonitrile

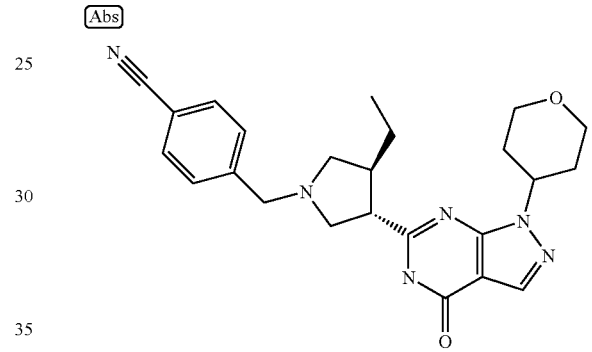

Following the procedure for the preparation of 6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one but substituting 6-[(3S,4S)-4-ethylpyrrolidin-3-yl]-1-(tetrahydro-2H-pyran-4-yl)-1H-pyrazolo[3,4-d]pyrimidin-4(5H)-one hydrogen chloride, sodium cyanoborohydride and 4-formylbenzonitrile provided the title compound. 400 MHz $^1$H NMR (CDCl$_3$) δ 11.82 (brs, 1H), 8.01 (s, 1H), 7.75 (t, J=7.9 Hz, 1H), 7.59-7.44 (m, 3H), 4.78-4.75 (m, 1H), 4.74 (s, 1H), 4.13-4.08 (m, 2H), 3.77 (m, 1H), 3.70 (m, 1H), 3.61-3.53 (m, 2H), 3.31-3.29 (m, 1H), 3.01-2.90 (m, 2H), 2.58 (m, 1H), 2.37-2.31 (m, 2H), 2.25 (m, 1H), 2.00 (m, 1H), 1.91-1.83 (m, 2H), 1.64-1.63 (m, 1H), 1.61-1.59 (m, 1H), 0.93 (t, J=7.5 Hz, 3H). MS: (M+H m/z 433.2).

BIOLOGICAL PROTOCOLS

The utility of the compounds of Formula (I), and the pharmaceutically acceptable salts thereof, in the treatment or prevention of diseases (such as are detailed herein) in mammals (e.g., humans) may be demonstrated by the activity thereof in conventional assays known to one of ordinary skill in the art, including the assay described below. Such assays also provide a means whereby the activities of the compounds of Formula (I) can be compared with the activities of other known compounds.

Phosphodiesterase 9 (PDE9) Inhibitory Activity

The PDE9 assay was performed using the Phosphodiesterase Scintillation Proximity (SPA) assay (GE Healthcare Life Sciences). The assay was carried out in 96 well clear bottom microtiter plates (Costar 3632, Corning Inc). The human recombinant PDE9 enzyme was generated in SF-9 cells, the cell pellets were sonicated in buffer (20 mM TRIS, 2 mM benzamidine, 1 mM EDTA, 250 mM sucrose, 100 μM PMSF, pH 7.5 with HCl), centrifuged at 40,000×g for 20 min at 4° C. The supernatants were stored at −80° C. [8-$^3$H] guanosine 3',5'-cyclic phosphate (TRK 392, GE Healthcare Life Sciences) was diluted in assay buffer (50 mM Tris-HCl, pH7.5, containing 1.3 mM $MgCl_2$) such that the final well concentration was 50 nM. Test compounds were dissolved in DMSO, diluted in DI $H_2O$ and serially diluted in 20% DMSO/80% $H_2O$, for a final concentration of 2% DMSO. For the assay the PDE9 was diluted with assay buffer such that 20% or less of the substrate was hydrolyzed to 5'GMP. Each assay well contained 10 μl of test compound or solvent, 40 μl of [$^3$H]CGMP and 50 μl of enzyme, background was determined by a high concentration of a PDE inhibitor. The assay was initiated with the addition of the enzyme and carried out at room temperature for 30 min. The assay was terminated with the addition of 10 μl of a PDE9 inhibitor that was sufficient to totally inhibit the enzyme activity, immediately followed by the addition of 50 μl per well of SPA beads. The plates were sealed, vortexed, allowed to set for >300 min, then counted in a Wallac TriLux MicroBeta LSC.

| Example No. | G5678A (U): IC50 |
|---|---|
| 3 | 9.46 nM |
| 4 | 624 nM |
| 5 | 558 nM |
| 6 | 57.1 nM |
| 7 | 11.6 nM |
| 8 | 11.2 nM |
| 9 | 2.84 nM |
| 10 | 4.98 nM |
| 11 | 18.9 nM |
| 12 | 7.23 nM |
| 13 | 6.61 nM |
| 14 | 26.0 nM |
| 17 | 16.2 nM |
| 18 | 8.26 nM |
| 19 | 2.68 nM |
| 20 | 7.06 nM |
| 21 | 34.5 nM |
| 22 | 43.6 nM |
| 23 | 1.32 nM |
| 24 | 119 nM |
| 25 | 9.07 nM |
| 26 | 11.4 nM |
| 27 | 7.45 nM |
| 28 | 6.86 nM |
| 29 | 2.17 nM |
| 31 | 23.2 nM |
| 32 | 5.19 nM |
| 33 | 6.29 nM |
| 34 | 4.33 nM |
| 35 | 53.8 nM |
| 36 | 5.08 nM |
| 37 | 3.23 nM |
| 38 | 5.75 nM |
| 39 | 58.1 nM |
| 40 | 44.5 nM |
| 41 | 63.8 nM |
| 42 | 268 nM |
| 43 | 36.4 nM |
| 44 | 10.9 nM |
| 45 | 38.7 nM |
| 46 | 8.53 nM |
| 47 | 5.53 nM |
| 48 | 40.7 nM |
| 49 | 4.55 nM |
| 50 | 125 nM |
| 51 | 8.19 nM |
| 52 | 26.0 nM |
| 53 | 7.30 nM |
| 54 | 14.7 nM |
| 55 | 6.55 nM |
| 56 | 4.81 nM |
| 57 | 122 nM |
| 58 | 334 nM |
| 59 | 7.37 nM |
| 60 | 44.8 nM |
| 61 | 7.35 nM |
| 62 | 520 nM |
| 63 | 123 nM |
| 64 | 873 nM |
| 65 | 17.1 nM |
| 66 | 18.1 nM |
| 67 | 9.74 nM |
| 68 | 36.7 nM |
| 69 | 30.7 nM |
| 70 | 10.2 nM |
| 71 | 16.1 nM |
| 72 | 40.1 nM |
| 73 | 6.01 nM |
| 74 | 6.14 nM |
| 75 | 5.46 nM |
| 76 | 3.50 nM |
| 77 | 1.24 nM |
| 78 | 4.35 nM |
| 79 | 3.72 nM |
| 80 | 3.72 nM |
| 81 | 2.92 nM |
| 82 | 5.18 nM |
| 83 | 24.5 nM |
| 84 | 1.87 nM |
| 85 | 0.903 nM |
| 86 | 1.44 nM |
| 87 | 5.72 nM |
| 88 | 17.9 nM |
| 89 | 1.70 nM |
| 90 | 1.41 nM |
| 91 | 6.69 nM |
| 92 | 23.3 nM |
| 93 | 24.3 nM |
| 94 | 14.2 nM |
| 95 | 3.92 nM |
| 96 | 7.13 nM |
| 97(a) | 7.20 nM |
| 97(b) | 5.56 nM |
| 98 | 7.93 nM |
| 99 | 12.8 nM |
| 100 | 22.7 nM |
| 101 | 7.94 nM |
| 102 | 19.7 nM |
| 103 | 15.2 nM |
| 104 | 3.98 nM |
| 105 | 3.29 nM |
| 106 | 8.06 nM |
| 107 | 4.33 nM |
| 108 | 3.11 nM |
| 109 | 4.21 nM |
| 110 | 2.59 nM |
| 111 | 12.5 nM |
| 112 | 1.37 nM |
| 113 | <1.00 nM |
| 114 | 2.31 nM |

The following additional compounds were made in accordance with the methods set forth above:

| Ex. No. | Structure | IUPACNAME | G5678A (U):IC50 | Exact Mass | Molec. Weight | Obs. m/z (M + 1) | Retention Time |
|---|---|---|---|---|---|---|---|
| 115 | Rac | 1-cyclopentyl-6-{(3,4-trans)-4-methyl-1-[3-(1H-pyrazol-1-yl)benzyl]pyrrolidin-3-yl}-1,5-dihydro-4H-pyrazolo[3,4-d]pyrimidin-4-one | 40.4 nM | 443.243 | 557.579 | 444.28 | 2.71 |
| 116 | Rac | 1-cyclopentyl-6-{(3,4-trans)-4-methyl-1-[(2-methylpyridin-4-yl)methyl]pyrrolidin-3-yl}-1,5-dihydro-4H-pyrazolo[3,4-d]pyrimidin-4-one | 34.0 nM | 392.233 | 620.556 | 393.32 | 2.04 |
| 117 | Rac | 6-[(3,4-trans)-1-(2-chloro-6-fluorobenzyl)-4-methylpyrrolidin-3-yl]-1-cyclopentyl-1,5-dihydro-4H-pyrazolo[3,4-d]pyrimidin-4-one | 126 nM | 429.173 | 543.951 | 430.23 | 2.7 |

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 118 | [Rac] | 1-cyclopentyl-6-[(3,4-trans)-1-(2,3-dimethylbenzyl)-4-methylpyrrolidin-3-yl]-1,5-dihydro-4H-pyrazolo[3,4-d]pyrimidin-4-one | 74. nM | 405.253 | 519.57 | 406.32 | 2.9 |
| 119 | [Rac] | 1-cyclopentyl-6-{(3,4-trans)-1-[2-(difluoromethoxy)benzyl]-4-methylpyrrolidin-3-yl}-1,5-dihydro-4H-pyrazolo[3,4-d]pyrimidin-4-one | 32.8 nM | 443.213 | 557.522 | 444.28 | 2.82 |
| 120 | [Rac] | 1-cyclopentyl-6-{(3,4-trans)-1-[(2-ethoxypyridin-3-yl)methyl]-4-methylpyrrolidin-3-yl}-1,5-dihydro-4H-pyrazolo[3,4-d]pyrimidin-4-one | 62.7 nM | 422.243 | 650.582 | 423.3 | 2.66 |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 121 | Rac | 1-cyclopentyl-6-[(3,4-trans)-4-methyl-1-(4,5,6,7-tetrahydropyrazolo[1,5-a]pyridin-3-ylmethyl)pyrrolidin-3-yl]-1,5-dihydro-4H-pyrazolo[3,4-d]pyrimidin-4-one | 83.9 nM | 421.259 | 535.573 | 422.33 | 2.43 |
| 122 | Rac | 1-cyclopentyl-6-[(3,4-trans)-1-(2-3-dihydro-1,4-benzodioxin-6-ylmethyl)-4-methylpyrrolidin-3-yl]-1,5-dihydro-4H-pyrazolo[3,4-d]pyrimidin-4-one | 56.4 nM | 435.227 | 549.552 | 436.28 | 2.68 |
| 123 | Rac | 1-cyclopentyl-6-{(3,4-trans)-1-[4-(1H-imidazol-1-yl)benzyl]-4-methylpyrrolidin-3-yl}-1,5-dihydro-4H-pyrazolo[3,4-d]pyrimidin-4-one | 39.3 nM | 443.243 | 557.579 | 444.29 | 2.11 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 124 | [Rac] | 1-cyclopentyl-6-[(3,4-trans)-1-(2,5-dichlorobenzyl)-4-methylpyrrolidin-3-yl]-1,5-dihydro-4H-pyrazolo[3,4-d]pyrimidin-4-one | 80.9 nM | 445.144 | 560.406 | 446.19 | 2.92 |
| 125 | [Rac] | 1-cyclopentyl-6-[(3,4-trans)-1-(4-methoxy-3-methylbenzyl)-4-methylpyrrolidin-3-yl]-1,5-dihydro-4H-pyrazolo[3,4-d]pyrimidin-4-one | 55.2 nM | 421.248 | 535.569 | 422.31 | 2.89 |
| 126 | [Rac] | 1-cyclopentyl-6-[(3,4-trans)-1-(2,3-dihydro-1-benzofuran-7-ylmethyl)-4-methylpyrrolidin-3-yl]-1,5-dihydro-4H-pyrazolo[3,4-d]pyrimidin-4-one | 88.7 nM | 419.232 | 533.553 | 420.31 | 2.75 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 127 | Rac | 1-cyclopentyl-6-[(3,4-trans)-1-(2,3-difluorobenzyl)-4-methylpyrrolidin-3-yl]-1,5-dihydro-4H-pyrazolo[3,4-d]pyrimidin-4-one | 61.7 nM | 413.203 | 527.496 | 414.28 | 2.73 |
| 128 | Rac | 1-cyclopentyl-6-[(3,4-trans)-1-(5-fluoro-2-methoxybenzyl)-4-methylpyrrolidin-3-yl]-1,5-dihydro-4H-pyrazolo[3,4-d]pyrimidin-4-one | 70.9 nM | 425.223 | 539.532 | 426.29 | 2.8 |
| 129 | Rac | 1-cyclopentyl-6-[(3,4-trans)-1-(2-fluoro-4-methoxybenzyl)-4-methylpyrrolidin-3-yl]-1,5-dihydro-4H-pyrazolo[3,4-d]pyrimidin-4-one | 71.8 nM | 425.223 | 539.532 | 426.29 | 2.75 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 130 | Rac | 1-cyclopentyl-6-[(3,4-trans)-1-(3-fluoro-4-methylbenzyl)-4-methylpyrrolidin-3-yl]-1,5-dihydro-4H-pyrazolo[3,4-d]pyrimidin-4-one | 60.0 nM | 409.228 | 523.533 | 410.28 | 2.87 |
| 131 | Rac | 1-cyclopentyl-6-{(3,4-trans)-4-methyl-1-[(2-methyl-1,3-thiazol-5-yl)methyl]pyrrolidin-3-yl}-1,5-dihydro-4H-pyrazolo[3,4-d]pyrimidin-4-one | 41.9 nM | 398.189 | 512.557 | 399.23 | 2.32 |
| 132 | Rac | 1-cyclopentyl-6-{(3,4-trans)-1-[(4-isopropyl-1,3-thiazol-2-yl)methyl]-4-methylpyrrolidin-3-yl}-1,5-dihydro-4H-pyrazolo[3,4-d]pyrimidin-4-one | 37.5 nM | 426.22 | 540.611 | 427.28 | 2.83 |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 133 | Rac | 1-cyclopentyl-6-{(3,4-trans)-1-[(1,3-dimethyl-1H-pyrazol-5-yl)methyl]-4-methylpyrrolidin-3-yl}-1,5-dihydro-4H-pyrazolo[3,4-d]pyrimidin-4-one | 33.7 nM | 395.243 | 509.535 | 396.31 | 2.35 |
| 134 | Rac | 1-cyclopentyl-6-[(3,4-trans)-1-(2,3-difluoro-4-methylbenzyl)-4-methylpyrrolidin-3-yl]-1,5-dihydro-4H-pyrazolo[3,4-d]pyrimidin-4-one | 93.5 nM | 427.218 | 541.523 | 428.29 | 2.89 |
| 135 | Rac | 1-cyclopentyl-6-[(3,4-trans)-4-methyl-1-{[6-(1H-pyrazol-1-yl)pyridin-2-yl]methyl}pyrrolidin-3-yl]-1,5-dihydro-4H-pyrazolo[3,4-d]pyrimidin-4-one | 91.6 nM | 444.239 | 675.592 | 445.3 | 2.59 |

-continued

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 136 | [Rac] | 1-cyclopentyl-6-[(3,4-trans)-4-methyl-1-(4-methylbenzyl)pyrrolidin-3-yl]-1,5-dihydro-4H-pyrazolo[3,4-d]pyrimidin-4-one | 132 nM | 391.237 | 505.543 | 392.31 | 2.81 |
| 137 | [Rac] | 1-cyclopentyl-6-[(3,4-trans)-4-methyl-1-(2-naphthylmethyl)pyrrolidin-3-yl]-1,5-dihydro-4H-pyrazolo[3,4-d]pyrimidin-4-one | 54.5 nM | 427.237 | 541.576 | 428.3 | 2.97 |
| 138 | [Rac] | 1-cyclopentyl-6-{(3,4-trans)-1-[(2-methoxypyridin-3-yl)methyl]-4-methylpyrrolidin-3-yl}-1,5-dihydro-4H-pyrazolo[3,4-d]pyrimidin-4-one | 47.7 nM | 408.227 | 636.555 | 409.26 | 2.5 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 139 | 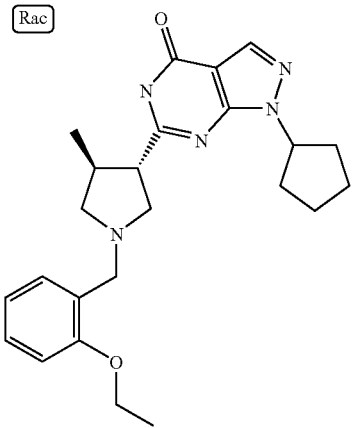 | 1-cyclopentyl-6-[(3,4-trans)-1-(2-ethoxybenzyl)-4-methylpyrrolidin-3-yl]-1,5-dihydro-4H-pyrazolo[3,4-d]pyrimidin-4-one | 97.5 nM | 421.248 | 535.569 | 422.33 | 2.88 |
| 140 | 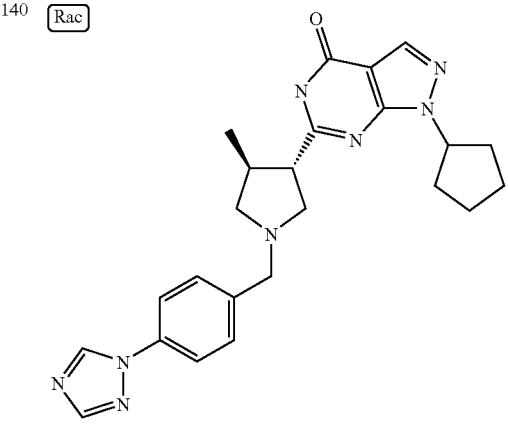 | 1-cyclopentyl-6-{(3,4-trans)-4-methyl-1-[4-(1H-1,2,4-triazol-1-yl)benzyl]pyrrolidin-3-yl}-1,5-dihydro-4H-pyrazolo[3,4-d]pyrimidin-4-one | 26.8 nM | 444.239 | 558.567 | 445.3 | 2.42 |
| 141 | 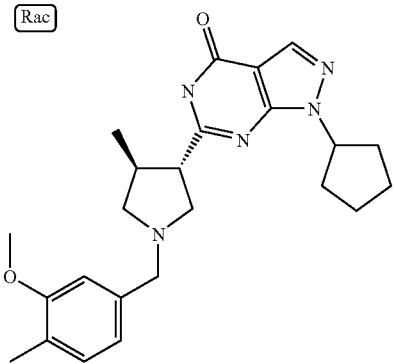 | 1-cyclopentyl-6-[(3,4-trans)-1-(3-methoxy-4-methylbenzyl)-4-methylpyrrolidin-3-yl]-1,5-dihydro-4H-pyrazolo[3,4-d]pyrimidin-4-one | 53.1 nM | 421.248 | 535.569 | 422.3 | 2.94 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 142 | Rac | 1-cyclopentyl-6-[(3,4-trans)-4-methyl-1-(1-naphthylmethyl)pyrrolidin-3-yl]-1,5-dihydro-4H-pyrazolo[3,4-d]pyrimidin-4-one | 47.5 nM | 427.237 | 541.576 | 428.3 | 2.93 |
| 143 | Rac | 1-cyclopentyl-6-[(3,4-trans)-1-(3-fluoro-4-methylbenzyl)-4-methylpyrrolidin-3-yl]-1,5-dihydro-4H-pyrazolo[3,4-d]pyrimidin-4-one | 35.1 nM | 425.223 | 539.532 | 426.29 | 2.73 |
| 144 | Rac | 1-cyclopentyl-6-[(3,4-trans)-1-(2,5-dimethoxybenzyl)-4-methylpyrrolidin-3-yl]-1,5-dihydro-4H-pyrazolo[3,4-d]pyrimidin-4-one | 99.6 nM | 437.243 | 551.568 | 438.29 | 2.79 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 145 | Rac | 1-cyclopentyl-6-{(3,4-trans)-4-methyl-1-[(5-methylisoxazol-3-yl)methyl]pyrrolidin-3-yl}-1,5-dihydro-4H-pyrazolo[3,4-d]pyrimidin-4-one | 77.4 nM | 382.212 | 496.492 | 383.27 | 2.5 |
| 146 | Rac | 1-cyclopentyl-6-[(3,4-trans)-1-(2-fluoro-6-methoxybenzyl)-4-methylpyrrolidin-3-yl]-1,5-dihydro-4H-pyrazolo[3,4-d]pyrimidin-4-one | 165 nM | 425.223 | 539.532 | 426.29 | 2.76 |
| 147 | Rac | 1-cyclopentyl-6-[(3,4-trans)-1-(2,4-difluorobenzyl)-4-methylpyrrolidin-3-yl]-1,5-dihydro-4H-pyrazolo[3,4-d]pyrimidin-4-one | 79.8 nM | 413.203 | 527.496 | 414.28 | 2.72 |
| 148 | Rac | 1-cyclopentyl-6-[(3,4-trans)-1-(4-fluoro-3-methoxybenzyl)-4-methylpyrrolidin-3-yl]-1,5-dihydro-4H-pyrazolo[3,4-d]pyrimidin-4-one | 36.0 nM | 425.223 | 539.532 | 426.29 | 2.79 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 149 | Rac | 1-cyclopentyl-6-[(3,4-trans)-1-(2,3-dihydro-1,4-benzodioxin-5-ylmethyl)-4-methylpyrrolidin-3-yl]-1,5-dihydro-4H-pyrazolo[3,4-d]pyrimidin-4-one | 47.1 nM | 435.227 | 549.552 | 436.28 | 2.73 |
| 150 | Rac | 6-[(3,4-trans)-1-(2-chloro 4-fluorobenzyl)-4-methylpyrrolidin-3-yl]-1-cyclopentyl-1,5-dihydro-4H-pyrazolo[3,4-]pyrimidin-4-one | 93.5 nM | 429.173 | 543.951 | 430.23 | 2.82 |
| 151 | Rac | 1-cyclopentyl-6-[(3,4-trans)-1-(2,4-dimethylbenzyl)-4-methylpyrrolidin-3-yl]-1,5-dihydro-4H-pyrazolo[3,4-d]pyrimidin-4-one | 117 nM | 405.253 | 519.57 | 406.32 | 2.92 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 152 | Rac | 1-cyclopentyl-6-[(3,4-trans)-1-(3,5-dimethoxybenzyl)-4-methylpyrrolidin-3-yl]-1,5-dihydro-4H-pyrazolo[3,4-d]pyrimidin-4-one | 42.2 nM | 437.243 | 551.568 | 438.29 | 2.8 |
| 153 | Rac | 1-cyclopentyl-6-[(3,4-trans)-1-(3-ethoxybenzyl)-4-methylpyrrolidin-3-yl]-1,5-dihydro-4H-pyrazolo[3,4-d]pyrimidin-4-one | 54.4 nM | 421.248 | 535.569 | 422.28 | 2.88 |
| 154 | Rac | 6-[(3,4-trans)-1-(4-chloro-2-fluorobenzyl)-4-methylpyrrolidin-3-yl]-1-cyclopentyl-1,5-dihydro-4H-pyrazolo[3,4-d]pyrimidin-4-one | 175 nM | 429.173 | 543.951 | 430.23 | 2.88 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 155 | [Rac] | 3-{[(3,4-trans)-3-(1-cyclopentyl-4-oxo-4,5-dihydro-1H-pyrazolo[3,4-d]pyrimidin-6-yl)-4-methylpyrrolidin-1-yl]methyl}benzonitrile | 27.9 nM | 402.217 | 516.526 | 403.25 | 2.61 |
| 156 | [Rac] | 1-cyclopentyl-6-[(3,4-trans)-1-(2,5-difluorobenzyl)-4-methylpyrrolidin-3-yl]-1,5-dihydro-4H-pyrazolo[3,4-d]pyrimidin-4-one | 40.8 nM | 413.203 | 527.496 | 414.27 | 2.69 |
| 157 | [Rac] | 2-{[(3,4-trans)-3-(1-cyclopentyl-4-oxo-4,5-dihydro-1H-pyrazolo[3,4-d]pyrimidin-6-yl)-4-methylpyrrolidin-1-yl]methyl}benzonitrile | 56.4 nM | 402.217 | 516.528 | 403.26 | 2.6 |

-continued

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 158 | Rac | 6-[(3,4-trans)-1-(3-chloro-4-fluorobenzyl)-4-methylpyrrolidin-3-yl]-1-cyclopentyl-1,5-dihydro-4H-pyrazolo[3,4-d]pyrimidin-4-one | 50.9 nM | 429.173 | 543.951 | 430.21 | 2.91 |
| 159 | Rac | 1-cyclopentyl-6-{(3,4-trans)-1-[4-(difluoromethoxy)benzyl]-4-methylpyrrolidin-3-yl}-1,5-dihydro-4H-pyrazolo[3,4-d]pyrimidin-4-one | 59.9 nM | 443.213 | 557.522 | 444.26 | 2.88 |
| 160 | Rac | 1-cyclopentyl-6-[(3,4-trans)-4-methyl-1-(3-methylbenzyl)pyrrolidin-3-yl]-1,5-dihydro-4H-pyrazolo[3,4-d]pyrimidin-4-one | 43.4 nM | 391.237 | 505.543 | 392.29 | 2.8 |

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 161 | [Rac] | 1-cyclopentyl-6-[(3,4-trans)-1-(3,4-difluorobenzyl)-4-methylpyrrolidin-3-yl]-1,5-dihydro-4H-pyrazolo[3,4-d]pyrimidin-4-one | 40.4 nM | 413.203 | 527.496 | 414.26 | 2.8 |
| 162 | [Rac] | 1-cyclopentyl-6-[(3,4-trans)-1-(2,5-dimethylbenzyl)-4-methylpyrrolidin-3-yl]-1,5-dihydro-4H-pyrazolo[3,4-d]pyrimidin-4-one | 60.1 nM | 405.253 | 519.57 | 406.32 | 2.92 |
| 163 | [Rac] | 6-[(3,4-trans)-1-(3-chloro-2-fluorobenzyl)-4-methylpyrrolidin-3-yl]-1-cyclopentyl-1,5-dihydro-4H-pyrazolo[3,4-d]pyrimidin-4-one | 53.4 nM | 429.173 | 543.951 | 430.22 | 2.85 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 164 | [Rac] | 1-cyclopentyl-6-[(3,4-trans)-1-(2,3-dichlorobenzyl)-4-methylpyrrolidin-3-yl]-1,5-dihydro-4H-pyrazolo[3,4-d]pyrimidin-4-one | 78.9 nM | 445.144 | 560.406 | 446.15 | 2.94 |
| 165 | [Rac] | 1-cyclopentyl-6-[(3,4-trans)-4-methyl-1-(1,3-thiazol-2-ylmethyl)pyrrolidin-3-yl]-1,5-dihydro-4H-pyrazolo[3,4-d]pyrimidin-4-one | 54.2 nM | 384.173 | 498.53 | 385.22 | 2.35 |
| 166 | [Rac] | 1-cyclopentyl-6-[(3,4-trans)-1-(3-fluoro-2-methylbenzyl)-4-methylpyrrolidin-3-yl]-1,5-dihydro-4H-pyrazolo[3,4-d]pyrimidin-4-one | 68.3 nM | 409.228 | 523.533 | 410.26 | 2.83 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 167 | [Rac] | 1-cyclopentyl-6-{(3,4-trans)-4-methyl-1-[(2-methylpyrimidin-5-yl)methyl]pyrrolidin-3-yl}-1,5-dihydro-4H-pyrazolo[3,4-d]pyrimidin-4-one | 40.7 nM | 393.228 | 507.519 | 394.3 | 2.21 |
| 168 | [Rac] | 1-cyclopentyl-6-{(3,4-trans)-1-[(2-ethylpyrimidin-5-yl)methyl]-4-methylpyrrolidin-3-yl}-1,5-dihydro-4H-pyrazolo[3,4-d]pyrimidin-4-one | 30.7 nM | 407.243 | 521.546 | 408.31 | 2.36 |
| 169 | [Rac] | 1-cyclopentyl-6-[(3,4-trans)-1-(4-isopropylbenzyl)-4-methylpyrrolidin-3-yl]-1,5-dihydro-4H-pyrazolo[3,4-d]pyrimidin-4-one | 117 nM | 419.269 | 533.597 | 420.34 | 3.1 |
| 170 | [Rac] | 1-cyclopentyl-6-{(3,4-trans)-1-[(1-ethyl-1H-pyrazol-4-yl)methyl]-4-methylpyrrolidin-3-yl}-1,5-dihydro-4H-pyrazolo[3,4-d]pyrimidin-4-one | 74.6 nM | 395.243 | 509.535 | 396.31 | 2.37 |

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 171 | Rac | 1-cyclopentyl-6-{(3,4-trans)-1-[(4-methoxypyridin-3-yl)methyl]-4-methylpyrrolidin-3-yl}-1,5-dihydro-4H-pyrazolo[3,4-d]pyrimidin-4-one | 51.3 nM | 408.227 | 636.555 | 409.29 | 2.05 |
| 172 | Rac | 1-cyclopentyl-6-[(3,4-trans)-1-(isoxazol-5-ylmethyl)-4-methylpyrrolidin-3-yl]-1,5-dihydro-4H-pyrazolo[3,4-d]pyrimidin-4-one | 67.0 nM | 368.196 | 482.465 | 369.25 | 2.29 |
| 173 | Rac | 1-cyclopentyl-6-[(3,4-trans)-1-(4-ethoxybenzyl)-4-methylpyrimidin-3-yl]-1,5-dihydro-4H-pyrazolo[3,4-d]pyrimidin-4-one | 64.0 nM | 421.248 | 535.569 | 422.29 | 2.85 |
| 174 | Rac | 1-cyclopentyl-6-[(3,4-trans)-1-{[6-(1-hydroxy-1-methylethyl)pyridin-3-yl]methyl}-4-methylpyrrolidin-3-yl]-1,5-dihydro-4H-pyrazolo[3,4-d]pyrimidin-4-one | 42.0 nM | 436.259 | 664.609 | 437.32 | 2.14 |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 175 | Rac | 1-cyclopentyl-6-{(3,4-trans)-1-[(2,2-dimethyl-2,3-dihydro-1-benzofuran-5-yl)methyl]-4-methylpyrrolidin-3-yl}-1,5-dihydro-4H-pyrazolo[3,4-d]pyrimidin-4-one | 74.8 nM | 447.264 | 561.607 | 448.3 | 2.96 |
| 176 | Rac | 1-cyclopentyl-6-[(3,4-trans)-1-(3,4-dimethoxybenzyl)-4-methylpyrrolidin-3-yl]-1,5-dihydro-4H-pyrazolo[3,4-d]pyrimidin-4-one | 27.1 nM | 437.243 | 551.568 | 438.29 | 2.59 |
| 177 | Rac | 1-cyclopentyl-6-{(3,4-trans)-4-methyl-1-[(5-methylpyrazin-2-yl)methyl]pyrrolidin-3-yl}-1,5-dihydro-4H-pyrazolo[3,4-d]pyrimidin-4-one | 42.2 nM | 393.228 | 507.519 | 394.3 | 2.32 |
| 178 | Rac | 1-cyclopentyl-6-[(3,4-trans)-1-(imidazo[1,2-a]pyridin-2-ylmethyl)-4-methylpyrrolidin-3-yl]-1,5-dihydro-4H-pyrazolo[3,4-d]pyrimidin-4-one | 44.7 nM | 417.228 | 531.541 | 418.27 | 2.14 |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 179 | Rac 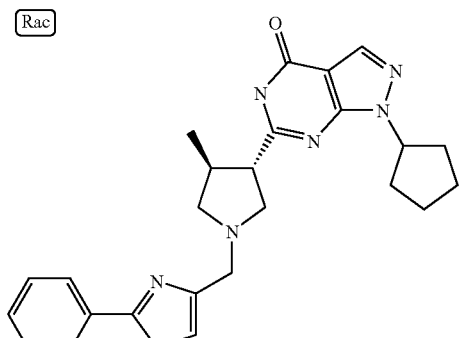 | 1-cyclopentyl-6-{(3,4-trans)-4-methyl-1-[(2-phenyl-1,3-oxazol-4-yl)methyl]pyrrolidin-3-yl}-1,5-dihydro-4H-pyrazolo[3,4-d]pyrimidin-4-one | 47.2 nM | 444.227 | 558.563 | 445.27 | 2.88 |
| 180 | 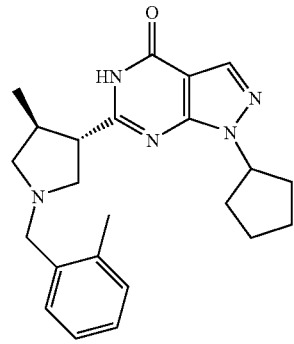 | 1-cyclopentyl-6-[(3,4-trans)-4-methyl-1-(2-methylbenzyl)pyrrolidin-3-yl]-1,5-dihydro-4H-pyrazolo[3,4-d]pyrimidin-4-one | 83.8 nM | 391.237 | 505.543 | 392.3 | 2.77 |
| 181 | Rac 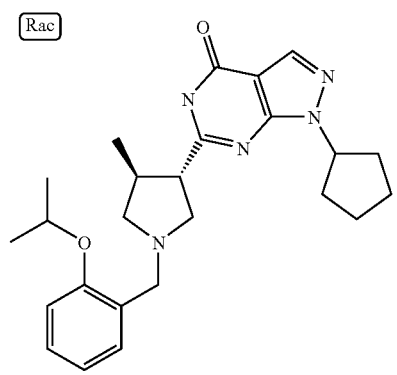 | 1-cyclopentyl-6-[(3,4-trans)-1-(2-isopropoxybenzyl)-4-methylpyrrolidin-3-yl]-1,5-dihydro-4H-pyrazolo[3,4-d]pyrimidin-4-one | 134 nM | 435.264 | 549.596 | 436.33 | 3 |
| 182 | Rac 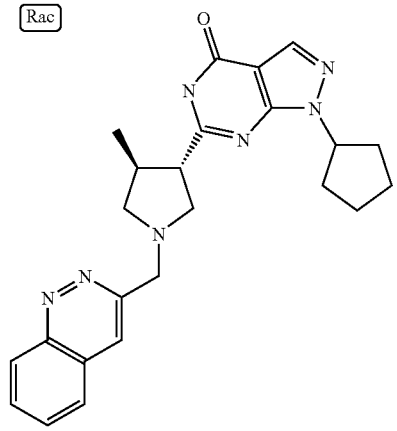 | 6-[(3,4-trans)-1-(cinnolin-3-ylmethyl)-4-methylpyrrolidin-3-yl]-1-cyclopentyl-1,5-dihydro-4H-pyrazolo[3,4-d]pyrimidin-4-one | 22.5 nM | 429.228 | 543.552 | 430.26 | 2.53 |

-continued

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 183 | Rac | 1-cyclopentyl-6-{(3,4-trans)-1-[3-(difluoromethoxy)benzyl]-4-methylpyrrolidin-3-yl}-1,5-dihydro-4H-pyrazolo[3,4-d]pyrimidin-4-one | 29.8 nM | 443.213 | 557.522 | 444.26 | 2.87 |
| 184 | Rac | 1-cyclopentyl-6-[(3,4-trans)-1-(4-fluoro-3-methylbenzyl)-4-methylpyrrolidin-3-yl]-1,5-dihydro-4H-pyrazolo[3,4-d]pyrimidin-4-one | 90.0 nM | 409.228 | 523.533 | 410.26 | 2.87 |
| 185 | Rac | 1-cyclopentyl-6-{(3,4-trans)-4-methyl-1-[4-(1H-pyrazol-1-yl)benzyl]pyrrolidin-3-yl}-1,5-dihydro-4H-pyrazolo[3,4-d]pyrimidin-4-one | 33.5 nM | 443.243 | 557.579 | 444.27 | 2.69 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 186 | Rac | 1-cyclopentyl-6-{(3,4-trans)-1-[(2,7-dimethylimidazo[1,2-a]pyridin-3-yl)methyl]-4-methylpyrrolidin-3-yl}-1,5-dihydro-4H-pyrazolo[3,4-d]pyrimidin-4-one | 155 nM | 445.259 | 559.595 | 446.27 | 2.19 |
| 187 | Rac | 1-cyclopentyl-6-[(3,4-trans)-1-(3,5-dichlorobenzyl)-4-methylpyrrolidin-3-yl]-1,5-dihydro-4H-pyrazolo[3,4-d]pyrimidin-4-one | 70.9 nM | 445.144 | 560.406 | 446.16 | 3.04 |
| 188 | Rac | 1-cyclopentyl-6-[(3,4-trans)-1-(4-isopropoxybenzyl)-4-methylpyrrolidin-3-yl]-1,5-dihydro-4H-pyrazolo[3,4-d]pyrimidin-4-one | 72.7 nM | 435.264 | 549.546 | 436.3 | 2.98 |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 189 | Rac | 1-cyclopentyl-6-[(3,4-trans)-1-{[2-(1-hydroxy-1-methylethyl)pyridin-4-yl]methyl}-4-methylpyrrolidin-3-yl]-1,5-dihydro-4H-pyrazolo[3,4-d]pyrimidin-4-one | 23.7 nM | 436.259 | 664.609 | 437.21 | 2.13 |
| 190 | Rac | 1-cyclopentyl-6-[(3,4-trans)-4-methyl-1-(4,5,6,7-tetrahydro-1,3-benzothiazol-2-ylmethyl)pyrrolidin-3-yl]-1,5-dihydro-4H-pyrazolo(3,4-d]pyrimidin-4-one | 55.4 nM | 438.22 | 552.622 | 439.27 | 2.81 |
| 191 | Rac | 1-cyclopentyl-6-[(3,4-trans)-1-(mesitylmethyl)-4-methylpyrrolidin-3-yl]-1,5-dihydro-4H-pyrazolo[3,4-d]pyrimidin-4-one | 198 nM | 419.269 | 533.597 | 420.34 | 3 |
| 192 | Rac | 1-cyclopentyl-6-[(3,4-trans)-1-(2,6-dichlorobenzyl)-4-methylpyrrolidin-3-yl]-1,5-dihydro-4H-pyrazolo[3,4-d]pyrimidin-4-one | 236 nM | 445.144 | 560.406 | 446.14 | 2.75 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 193 | 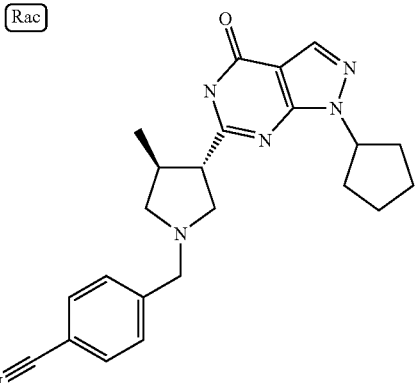 | 4-{[(3,4-trans)-3-(1-cyclopentyl-4-oxo-4,5-dihydro-1H-pyrazolo[3,4-d]pyrimidin-6-yl)-4-methylpyrrolidin-1-yl]methyl}benzonitrile | 57.7 nM | 402.217 | 516.526 | 403.25 | 2.61 |
| 194 | 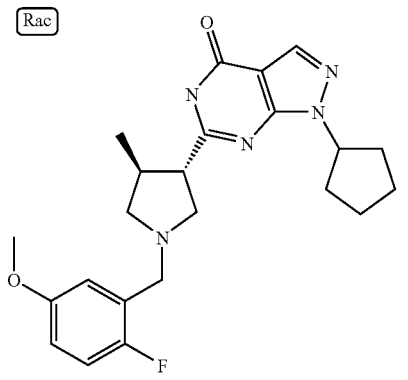 | 1-cyclopentyl-6-[(3,4-trans)-1-(2-fluoro-5-methoxybenzyl)-4-methylpyrrolidin-3-yl]-1,5-dihydro-4H-pyrazolo[3,4-d]pyrimidin-4-one | 54.7 nM | 425.223 | 539.532 | 426.29 | 2.75 |
| 195 | 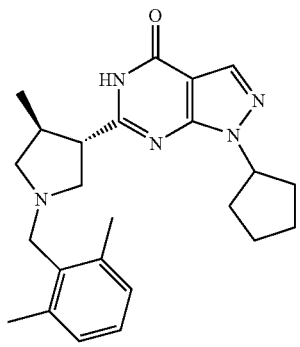 | 1-cyclopentyl-6-[(3,4-trans)-1-(2,6-dimethylbenzyl)-4-methylpyrrolidin-3-yl]-1,5-dihydro-4H-pyrazolo[3,4-d]pyrimidin-4-one | 198 nM | 405.253 | 519.57 | 406.31 | 2.83 |
| 196 | 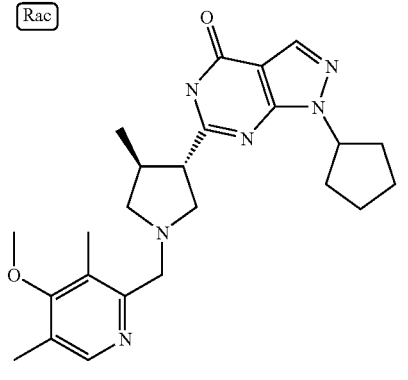 | 1-cyclopentyl-6-{(3,4-trans)-1-[(4-methoxy-3,5-dimethylpyridin-2-yl)methyl]-4-methylpyrrolidin-3-yl}-1,5-dihydro-4H-pyrazolo[3,4-d]pyrimidin-4-one | 187 nM | 436.259 | 664.609 | 437.32 | 2.76 |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 197 | Rac 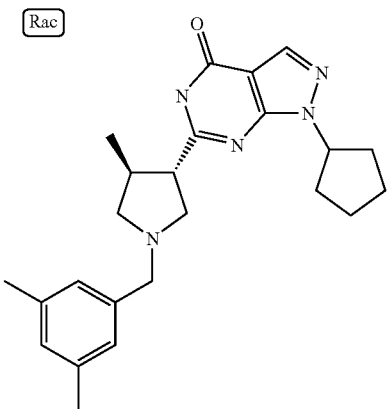 | 1-cyclopentyl-6-[(3,4-trans)-1-(3,5-dimethylbenzyl)-4-methylpyrrolidin-3-yl]-1,5-dihydro-4H-pyrazolo[3,4-d]pyrimidin-4-one | 53.5 nM | 405.253 | 519.57 | 406.33 | 2.96 |
| 198 | Rac 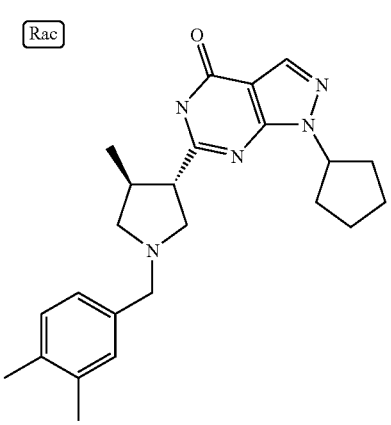 | 1-cyclopentyl-6-[(3,4-trans)-1-(3,4-dimethylbenzyl)-4-methylpyrrolidin-3-yl]-1,5-dihydro-4H-pyrazolo[3,4-d]pyrimidin-4-one | 93.6 nM | 405.253 | 519.57 | 406.31 | 2.94 |
| 199 | Rac 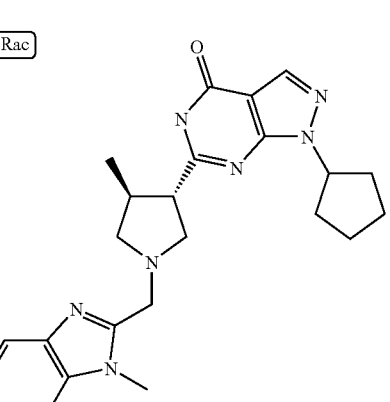 | 1-cyclopentyl-6-{(3,4-trans)-4-methyl-1-[(1-methyl-1H-benzimidazol-2-yl)methyl]pyrrolidin-3-yl}-1,5-dihydro-4H-pyrazolo[3,4-d]pyrimidin-4-one | 35.3 nM | 431.243 | 545.568 | 432.29 | 2.64 |
| 200 | Rac 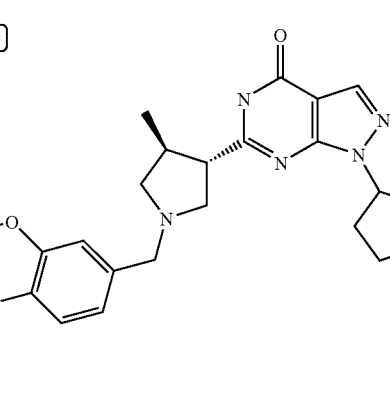 | 1-cyclopentyl-6-{(3,4-trans)-4-methyl-1-[(4-methyl-3,4-dihydro-2H-1,4-benzoxazin-7-yl)methyl]pyrrolidin-3-yl}-1,5-dihydro-4H-pyrazolo[3,4-d]pyrimidin-4-one | 176 nM | 448.259 | 676.62 | {449.3} | {2.78} |

-continued

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 201 | Rac | 1-cyclopentyl-6-[(3,4-trans)-4-methyl-1-(3-phenylpropyl)pyrrolidin-3-yl]-1,5-dihydro-4H-pyrazolo[3,4-d]pyrimidin-4-one | 146 nM | 405.253 | 519.57 | {406.3} | {2.93} |
| 202 | Rac | 1-cyclopentyl-6-{(3,4-trans)-4-methyl-1-[2-(trifluoromethyl)benzyl]pyrrolidin-3-yl}-1,5-dihydro-4H-pyrazolo[3,4-d]pyrimidin-4-one | 104 nM | 445.209 | 559.513 | {446.2} | {2.9} |
| 203 | Rac | 1-cyclopentyl-6-{(3,4-trans)-4-methyl-1-(4,4,4-trifluorobutyl)pyrrolidin-3-yl]-1,5-dihydro-4H-pyrazolo[3,4-d]pyrimidin-4-one | 83.7 nM | 397.209 | 511.469 | {398.2} | {2.69} |
| 204 | Rac | 1-cyclopentyl-6-[(3,4-trans)-1-(3-methoxybenzyl)-4-methylpyrrolidin-3-yl]-1,5-dihydro-4H-pyrazolo[3,4-d]pyrimidin-4-one | 9.56 nM | 407.232 | 521.542 | {408.3} | {2.74} |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 205 | [Rac] | 1-cyclopentyl-6-[(3,4-trans)-1-(cyclopentylmethyl)-4-methylpyrrolidin-3-yl]-1,5-dihydro-4H-pyrazolo[3,4-d]pyrimidin-4-one | 286 nM | 369.253 | 485.537 | {370.2} | {2.72} |
| 206 | [Rac] | 1-cyclopentyl-6-[(3,4-trans)-1-(2,4-dimethoxybenzyl)-4-methylpyrrolidin-3-yl]-1,5-dihydro-4H-pyrazolo[3,4-d]pyrimidin-4-one | 68.4 nM | 437.243 | 551.568 | {438.2} | {2.82} |
| 207 | [Rac] | 1-cyclopentyl-6-{(3,4-trans)-4-methyl-1-[4-(morpholin-4-ylmethyl)benzyl]pyrrolidin-3-yl}-1,5-dihydro-4H-pyrazolo[3,4-d]pyrimidin-4-one | 46.2 nM | 476.29 | 590.649 | {477.3; 477.3} | {1.94; 2.17} |
| 208 | [Rac] | 6-[(3,4-trans)-1-(2,1,3-benzothiadiazol-5-ylmethyl)-4-methylpyrrolidin-3-yl]-1-cyclopentyl-1,5-dihydro-4H-pyrazolo[3,4-d]pyrimidin-4-one | 7.13 nM | 435.184 | 549.578 | {436.2} | {2.66} |

-continued

| Ex. No. | Structure | IUPAC NAME | G5678A (U):IC50 | Exact Mass | Molec. Weight | Obs. m/z (M + 1) | Retention Time |
|---|---|---|---|---|---|---|---|
| 209 | [Rac] | 6-{(3,4-trans)-1-[2-(benzyloxy)ethyl]-4-methylpyrrolidin-3-yl}-1-cyclopentyl-1,5-dihydro-4H-pyrazolo[3,4-d]pyrimidin-4-one | 52.9 nM | 421.248 | 535.569 | {422.2} | {2.85} |
| 210 | [Rac] | 1-cyclopentyl-6-[(3,4-trans)-1-(2,6-diflurobenzyl)-4-methylpyrrolidin-3-yl]-1,5-dihydro-4H-pyrazolo[3,4-d]pyrimidin-4-one | 16.2 nM | 413.203 | 527.496 | {414.2} | {2.62} |
| 211 | [Rac] | 1-cyclopentyl-6-[(3,4-trans)-1-(2-methoxybenzyl)-4-methylpyrrolidin-3-yl]-1,5-dihydro-4H-pyrazolo[3,4-d]pyrimidin-4-one | 39.8 nM | 407.232 | 521.542 | {408.2} | {2.76} |
| 212 | [Rac] | 1-cyclopentyl-6-{(3,4-trans)-4-methyl-1-[(3,5,6-trimethylpyrazin-2-yl)methyl]pyrrolidin-3-yl}-1,5-dihydro-4H-pyrazolo[3,4-d]pyrimidin-4-one | 9.98 nM | 421.259 | 535.573 | {422.3} | {2.51} |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 213 | 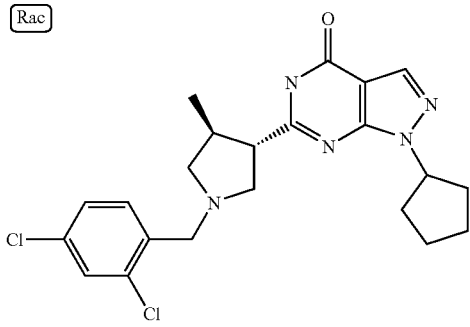 | 1-cyclopentyl-6-[(3,4-trans)-1-(2,4-dichlorobenzyl)-4-methylpyrrolidin-3-yl]-1,5-dihydro-4H-pyrazolo[3,4-d]pyrimidin-4-one | 124 nM | 445.144 | 560.406 | {446.1} | {2.98} |
| 214 | 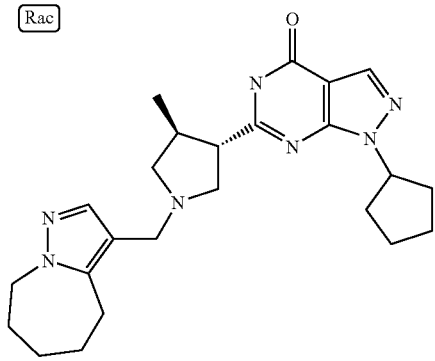 | 1-cyclopentyl-6-[(3,4-trans)-4-methyl-1-(5,6,7,8-tetrahydro-4H-pyrazolo[1,5-a]azepin-3-ylmethyl)pyrrolidin-3-yl]-1,5-dihydro-4H-pyrazolo[3,4-d]pyrimidin-4-one | 15.7 nM | 435.275 | 549.6 | {436.3} | {2.59} |
| 215 | 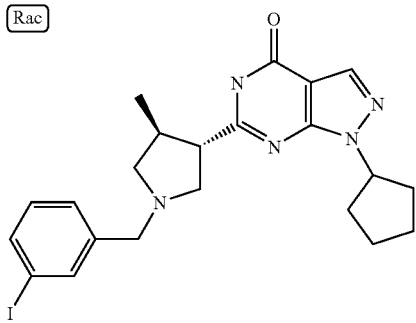 | 1-cyclopentyl-6-[(3,4-trans)-1-(3-fluorobenzyl)-4-methylpyrrolidin-3-yl]-1,5-dihydro-4H-pyrazolo[3,4-d]pyrimidin-4-one | 11.5 nM | 395.212 | 509.506 | {396.2} | {2.73} |
| 216 | 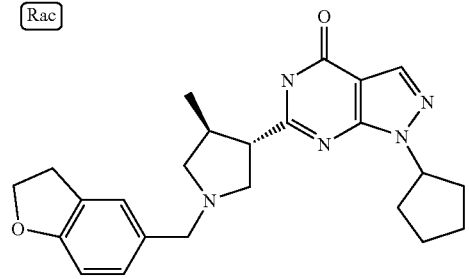 | 1-cyclopentyl-6-[(3,4-trans)-1-(2,3-dihydro-1-benzofuran-5-ylmethyl)-4-methylpyrrolidin-3-yl]-1,5-dihydro-4H-pyrazolo[3,4-d]pyrimidin-4-one | 17.4 nM | 419.232 | 533.553 | {420.2} | {2.71} |

| Ex. No. | Structure | IUPACNAME | G5678A (U):IC50 | Exact Mass | Molec. Weight | Obs. m/z (M + 1) | Retention Time |
|---|---|---|---|---|---|---|---|
| 217 | Rac | 1-cyclopentyl-6-[(3,4-trans)-1-(2-methoxy-5-methylbenzyl)-4-methylpyrrolidin-3-yl]-1,5-dihydro-4H-pyrazolo[3,4-d]pyrimidin-4-one | 25.0 nM | 421.248 | 535.569 | {422.3} | {2.91} |
| 218 | Rac | 1-cyclopentyl-6-[(3,4-trans)-1-(2-fluorobenzyl)-4-methylpyrrolidin-3-yl]-1,5-dihydro-4H-pyrazolo[3,4-d]pyrimidin-4-one | 15.6 nM | 395.212 | 509.506 | {396.2} | {2.67} |
| 219 | Rac | 6-[(3,4-trans)-1-(2-chlorobenzyl)-4-methylpyrrolidin-3-yl]-1-cyclopentyl-1,5-dihydro-4H-pyrazolo[3,4-d]pyrimidin-4-one | 48.4 nM | 411.183 | 525.961 | {412.2} | {2.78} |
| 220 | Rac | 1-cyclopentyl-6-[(3,4-trans)-1-(3,4-dichlorobenzyl)-4-methylpyrrolidin-3-yl]-1,5-dihydro-4H-pyrazolo[3,4-d]pyrimidin-4-one | 28.0 nM | 445.144 | 560.406 | {446.1} | {3.04} |
| 221 | Rac | 6-[(3,4-trans)-1-(2,1,3-benzothiadiazol-4-ylmethyl)-4-methylpyrrolidin-3-yl]-1-cyclopentyl-1,5-dihydro-4H-pyrazolo[3,4-d]pyrimidin-4-one | 12.7 nM | 435.184 | 549.578 | {436.2} | {2.67} |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 222 | Rac | 1-cyclopentyl-6-{(3,4-trans)-4-methyl-1-[(2-propylpyrimidin-5-yl)methyl]pyrrolidin-3-yl}-1,5-dihydro-4H-pyrazolo[3,4-d]pyrimidin-4-one | 6.03 nM | 421.259 | 535.573 | {422.3} | {2.52} |
| 223 | Rac | 1-cyclopentyl-6-{(3,4-trans)-1-[(1-ethyl-1H-pyrazol-5-yl)methyl]-4-methylpyrrolidin-3-yl}-1,5-dihydro-4H-pyrazolo[3,4-d]pyrimidin-4-one | 14.4 nM | 395.243 | 509.535 | {396.3} | {2.39} |
| 224 | Rac | 1-cyclopentyl-6-{(3,4-trans)-4-methyl-1-[2-(trifluoromethoxy)benzyl]pyrrolidin-3-yl}-1,5-dihydro-4H-pyrazolo[3,4-d]pyrimidin-4-one | 116 nM | 461.204 | 575.512 | {462.2} | {2.96} |
| 225 | Rac | 1-cyclopentyl-6-{(3,4-trans)-4-methyl-1-[4-(trifluoromethoxy)benzyl]pyrrolidin-3-yl}-1,5-dihydro-4H-pyrazolo[3,4-d]pyrimidin-4-one | 34.9 nM | 445.209 | 559.513 | {446.2} | {3.01} |

-continued

| Ex. No. | Structure | IUPACNAME | G5678A (U):IC50 | Exact Mass | Molec. Weight | Obs. m/z (M + 1) | Retention Time |
|---|---|---|---|---|---|---|---|
| 226 | [Rac] | 1-cyclopentyl-6-{(3,4-trans)-4-methyl-1-[(1-methyl-1H-imidazo[4,5-c]pyridin-2-yl)methyl]pyrrolidin-3-yl}-1,5-dihydro-4H-pyrazolo[3,4-d]pyrimidin-4-one | 3.78 nM | 432.239 | 660.581 | {433.2} | {2.03} |
| 227 | [Rac] | 1-cyclopentyl-6-[(3,4-trans)-1-(3,5-difluorobenzyl)-4-methylpyrrolidin-3-yl]-1,5-dihydro-4H-pyrazolo[3,4-d]pyrimidin-4-one | 7.42 nM | 413.203 | 527.496 | {414.2} | {2.79} |
| 228 | [Rac] | 1-cyclopentyl-6-[(3,4-trans)-1-(5,6-dihydro-4H-pyrrolo[1,2-b]pyrazol-3-ylmethyl)-4-methylpyrrolidin-3-yl]-1,5-dihydro-4H-pyrazolo[3,4-d]pyrimidin-4-one | 49.1 nM | 407.243 | 521.546 | {408.3} | {2.37} |

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A compound of Formula (I),

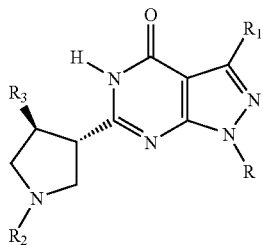

(I)

or a pharmaceutically acceptable salt thereof, wherein:
R is selected from the group consisting of $(C_1-C_6)$alkyl, $(C_2-C_6)$alkenyl, $(C_2-C_6)$alkynyl, $(C_3-C_8)$cycloalkyl, heterocycloalkyl, aryl, and heteroaryl, each of which optionally may be substituted with one to three substituents, the substituents being independently selected from the group consisting of $(C_1-C_4)$alkyl, $(C_1-C_4)$alkoxy, halo, and $(C_1-C_4)$haloalkyl, $R_1$ is selected from the group consisting of hydrogen, $(C_1-C_4)$alkyl, $(C_2-C_4)$alkenyl, $(C_2-C_4)$alkynyl, $(C_1-C_4)$haloalkyl, and cyclopropyl;

$R_2$ is selected from the group consisting of $(C_1-C_6)$alkyl, $(C_2-C_6)$alkenyl, $(C_2-C_6)$alkynyl, $(C_1-C_6)$haloalkyl, heteroaryl selected from the group consisting of pyridinyl, pyridazinyl, pyrimidinyl, and pyrazinyl, and $ER_5$, wherein the heteroaryl optionally may be substituted with one to three substituents independently selected from the group consisting of $(C_1-C_4)$alkyl and $(C_1-C_4)$haloalkyl;

$R_3$ is selected from the group consisting of hydrogen, $(C_1-C_4)$alkyl, $(C_2-C_4)$alkenyl, $(C_2-C_4)$alkynyl, $(C_3-C_6)$cycloalkyl, and $(C_1-C_4)$haloalkyl;

E is selected from the group consisting of —$CH_2$—, —$CH_2CH_2$—, —$CH_2CH_2CH_2$—, and —C(O)—;

$R_5$ is selected from the group consisting of $(C_3-C_8)$cycloalkyl, heterocycloalkyl, aryl, aryloxy, and heteroaryl, any of which optionally may be substituted with one to three substituents, such substituents being independently selected from the group consisting of $(C_1-C_4)$ alkyl, $(C_2-C_4)$alkenyl, $(C_2-C_4)$alkynyl, $(C_1-C_4)$hydroxyalkyl, $(C_1-C_4)$haloalkyl, $(C_1-C_4)$alkoxy, $(C_1-C_4)$haloalkoxy, $(C_3-C_8)$cycloalkyl, halo, cyano, phenyl, morpholinyl, $(C_1-C_4)$alkylamino, pyrazolyl, triazolyl, and imidazolyl.

2. The compound of claim 1, or a pharmaceutically acceptable salt thereof, wherein:
R is selected from the group consisting of ethyl, isopropyl, trifluoroethyl, cyclobutyl, cyclopentyl, difluorocyclohexyl, methoxyphenyl, tetrahydro-2H-thiopyran-4-yl, and tetrahydro-2H-pyran-4-yl;
$R_1$ is hydrogen or methyl;
$R_2$ is methyl, trifluoroethyl, trifluorobutyl, pyrimidinyl, trifluoromethylpyrimidinyl, or $ER_5$;
$R_3$ is methyl, ethyl, isopropyl, trifluoromethyl, trifluoroethyl, or cyclopropyl;
E is —$CH_2$— or —C(O)—;
$R_5$ is selected from the group consisting of substituted or unsubstituted cyclopentyl, morpholinyl, phenyl, naphthyl, benzyloxy, pyrimidinyl, pyridinyl, quinolinyl, quinoxalinyl, pyrazinyl, pyrazolyl, benzimidazolyl, cinnolinyl, naphthydrinyl, pyrido[2,3-b]pyrazinyl, imidazo[4,5-c]pyridinyl, benzothiadiazolyl, tetrahydropyrazolo[1,5-a]pyridinyl, dihydrobenzodioxinyl, imidazolyl, dihydrobenzofuranyl, triazolyl, oxazolyl, isoxazolyl, benzodioxinyl, thiazolyl, imidazo[1,2-a]pyridinyl, tetrahydrobenzothiazolyl, dihydrobenzoxazinyl, tetrahydropyranyl, tetrahydropyrazolo[1,5-a]azepinyl, and dihydropyrrolo[1,2-b]pyrazolyl.

3. The compound of claim 2, or a pharmaceutically acceptable salt thereof, wherein:
R is selected from the group consisting of isopropyl, cyclobutyl, cyclopentyl, and tetrahydro-2H-pyranyl;
$R_1$ is hydrogen;
$R_2$ is $ER_5$;
$R_3$ is methyl or ethyl;
E is —$CH_2$—; and
$R_5$ is selected from the group consisting of phenyl, pyrimidin-2-yl, pyridin-2-yl, pyrazin-2-yl, and 5-methylpyrazin-2-yl.

4. The compound of claim 3, wherein R is tetrahydro-2H-pyranyl.

5. The compound selected from the group consisting of:
6-[(3S,4S)-1-benzyl-4-methylpyrrolidin-3-yl]-1-cyclopentyl-1,5-dihydro-4H-pyrazolo [3,4-d]pyrimidin-4-one;
1-cyclopentyl-6-[(3S,4S)-4-methyl-1-(quinoxalin-6-ylmethyl)pyrrolidin-3-yl]-1,5-dihydro-4H-pyrazolo[3,4-d]pyrimidin-4-one;
1-cyclopentyl-6-{(3S,4S)-4-methyl-1-[(5-methylpyrazin-2-yl)methyl]pyrrolidin-3-yl}-1,5-dihydro-4H-pyrazolo[3,4-d]pyrimidin-4-one;
1-cyclopentyl-6-{(3S,4S)-1-[(1,3-dimethyl-1H-pyrazolo-5-yl)methyl]-4-methylpyrrolidin-3-yl}-1,5-dihydro-4H-pyrazolo[3,4-d]pyrimidin-4-one;
1-cyclopentyl-6-[(3S,4S)-4-methyl-1-(4,5,6,7-tetrahydropyrazolo[1,5-a]pyridin-3-ylmethyl)pyrrolidin-3-yl]-1,5-dihydro-4H-pyrazolo[3,4-d]pyrimidin-4-one;
1-cyclopentyl-6-{(3S,4S)-4-methyl-1-[(1-methyl-1H-benzimidazol-2-yl)methyl]pyrrolidin-3-yl}-1,5-dihydro-4H-pyrazolo[3,4-d]pyrimidin-4-one;
6-[(3S,4S)-1-(cinnolin-3-ylmethyl)-4-methylpyrrolidin-3-yl]-1-cyclopentyl-1,5-dihydro-4H-pyrazolo[3,4-d]pyrimidin-4-one;
1-cyclopentyl-6-{(3S,4S)-4-methyl-1-[(2-methylpyrimidin-4-yl)methyl]pyrrolidin-3-yl}-1,5-dihydro-4H-pyrazolo[3,4-d]pyrimidin-4-one; and
1-cyclopentyl-6-[(3S,4S)-1-{[2-(dimethylamino)pyrimidin-4-yl]methyl-}4-methylpyrrolidin-3-yl]-1,5-dihydro-4H-pyrazolo[3,4-d]pyrimidin-4-one;
or a pharmaceutically acceptable salt thereof.

6. The compound of claim 1, selected from the group consisting of:
6-[(3S,4S)-1-benzyl-4-ethylpyrrolidin-3-yl]-1-isopropyl-1,5-dihydro-4H-pyrazolo[3,4-d]pyrimidin-4-one;
6-[(3S,4S)-1-benzyl-4-methylpyrrolidin-3-yl]-1-isopropyl-1,5-dihydro-4H-pyrazolo[3,4-d]pyrimidin-4-one;
1-isopropyl-6-[(3S,4S)-4-methyl-1-(quinoxalin-6-ylmethyl)pyrrolidin-3-yl]-1,5-dihydro-4H-pyrazolo[3,4-d]pyrimidin-4-one:
1-isopropyl-6-[(3S,4S)-4-methyl-1-(quinolin-3-ylmethyl)pyrrolidin-3-yl]-1,5-dihydro-4H-pyrazolo [3,4-d]pyrimidin-4-one;
1-isopropyl-6-{(3S,4S)-4-methyl-1-[(2-methylpyrimidin-5-yl)methyl]pyrrolidin-3-yl}-1,5-dihydro-4H-pyrazolo[3,4-d]pyrimidin-4-one;
1-isopropyl-6-{(3S,4S)-1-[(6-methoxypyridin-3-yl)methyl]-4-methylpyrrolidin-3-yl}-1,5-dihydro-4H-pyrazolo[3,4-d]pyrimidin-4-one;
1-isopropyl-6-{(3S,4S)-4-methyl-1-[(5-methylpyrazin-2-yl)methyl]pyrrolidin-3-yl}-1,5-dihydro-4H-pyrazolo[3,4-d]pyrimidin-4-one;
1-isopropyl-6-[(3S,4S)-4-methyl-1-(1,5-naphthyridin-4-ylmethyl)pyrrolidin-3-yl]-1,5-dihydro-4H-pyrazolo[3,4-d]pyrimidin-4-one;
1-isopropyl-6-[(3S,4S)-4-methyl-1-(1,8-naphthyridin-4-ylmethyl)pyrrolidin-3-yl]-1,5-dihydro-4H-pyrazolo[3,4-d]pyrimidin-4-one;
1-isopropyl-6-[3S,4S)-4-methyl-1-(quinolin-4-ylmethyl)pyrrolidin-3-yl]-1,5-dihydro-4H-pyrazolo[3,4-d]pyrimidin-4-one; and
1-isopropyl-6-[(3S,4S)-4-methyl-1-(pyrido[2,3-b]pyrazin-8-ylmethyl)pyrrolidin-3-yl]-1,5-dihydro-4H-pyrazolo[3,4-d]pyrimidin-4-one;
or a pharmaceutically acceptable salt thereof.

7. The compound of claim 1, selected from the group consisting of:
6-[(3S,4S)-1-benzyl-4-methylpyrrolidin-3-yl]-1-(tetrahydro-2H-pyran-4-yl)-1,5-dihydro-4H-pyrazolo[3,4-d]pyrimidin-4-one;
6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one;
6-{(3S,4S)-4-methyl-1-[(5-methylpyrazin-2-yl)methyl]pyrrolidin-3-yl}-1-(tetrahydro-2H-pyran-4-yl)-1,5-dihydro-4H-pyrazolo[3,4-d]pyrimidin-4-one;
6-{(3S,4S)-1-[(6-methoxypyridin-3-yl)methyl]-4-methylpyrrolidin-3-yl}-1-(tetrahydro-2H-pyran-4-yl)-1,5-dihydro-4H-pyrazolo[3,4-d]pyrimidin-4-one;
6-[(3S,4S)-4-methyl-1-(quinolin-3-ylmethyl)pyrrolidin-3-yl]-1-(tetrahydro-2H-pyran-4-yl)-1,5-dihydro-4H-pyrazolo[3,4-d]pyrimidin-4-one;
6-{(3S,4S)-4-methyl-1-[(2-methylpyrimidin-4-yl)methyl]pyrrolidin-3-yl}-1-(tetrahydro-2H-pyran-4-yl)-1,5-dihydro-4H-pyrazolo[3,4-d]pyrimidin-4-one;
6-{(3S,4S)-4-methyl-1-[(6-methylpyridin-3-yl)methyl]pyrrolidin-3-yl}-1-(tetrahydro-2H-pyran-4-yl-1,5-dihydro-4H-pyrazolo[3,4-d]pyrimidin-4-one;
6-[(3S,4S)-4-methyl-1-{[6-(trifluoromethyl)pyridin-3-yl]methyl}pyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[(1-methyl-1H-imidazo[4,5-c]pyridin-2-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-1-[(1,3-dimethyl-1H-pyrazolo-5-yl)methyl]-4-methylpyrrolidin-3-yl}-1-(tetrahydro-2H-pyran-4-yl)-1,5-dihydro-4H-pyrazolo[3,4-d]pyrimidin-4-one;

6-[(3S,4S)-1-(2,1,3-benzothiadiazol-5-ylmethyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-4-methyl-1-(quinoxalin-2-ylmethyl)pyrrolidin-3-yl]-1-(tetrahydro-2H-pyran-4-yl)-1,5-dihydro-4H-pyrazolo[3,4-d]pyrimidin-4-one;

6-[(3S,4S)-4-methyl-1-(quinolin-4-ylmethyl)pyrrolidin-3-yl]-1-tetrahydro-2H-pyran-4-yl)-1,5-dihydro-4H-pyrazolo[3,4-d]pyrimidin-4-one;

6-[(3S,4S)-4-methyl-1-(pyridin-2-ylmethyl)pyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-methylpyrrolidin-3-yl]-3-methyl-1-(tetrahydro-2H-pyran-4-yl)-1,5-dihydro-4H-pyrazolo[3,4-d]pyrimidin-4-one;

6-[(3S,4S)-1-(3-fluorobenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(3,5-difluorobenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[4-(trifluoromethyl)benzyl]pyrrolidin-3-yl}-1-(tetrahydro-2H-pyran-4-yl)-1,5-dihydro-4H-pyrazolo[3,4-d]pyrimidin-4-one;

3-methyl-6-[(3S,4S)-4-methyl-1-(pyridin-3-ylmethyl)pyrrolidin-3-yl]-1-(tetrahydro-2H-pyran-4-yl)-1,5-dihydro-4H-pyrazolo[3,4-d]pyrimidin-4-one;

3-methyl-6-{(3S,4S)-4-methyl-1-[(2-methylpyrimidin-5-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-1-[(6-methoxypyridin-3-yl)methyl]-4-methylpyrrolidin-3-yl}-3-methyl-1-(tetrahydro-2H-pyran-4-yl)-1,5-dihydro-4H-pyrazolo[3,4-d]pyrimidin-4-one;

6-{(3S,4S)-4-methyl-1-[(6-methylpyridin-2-yl)methyl]pyrrolidin-3-yl}-1-(tetrahydro-2H-pyran-4-yl)-1,5-dihydro-4H-pyrazolo[3,4-d]pyrimidin-4-one;

6-[(3S,4S)-1-(4-fluorobenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-ethylpyrrolidin-3-yl]-1-(tetrahydro-2H-pyran-4-yl)-1,5-dihydro-4H-pyrazolo[3,4-d]pyrimidin-4-one;

6-[(3S,4S)-1-(2-fluorobenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[2-(trifluoromethyl)benzyl]pyrrolidin-3-yl}-1-(tetrahydro-2H-pyran-4-yl)-1,5-dihydro-4H-pyrazolo[3,4-d]pyrimidin-4-one;

6-[(3S,4S)-1-(2,4-difluorobenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(4-methoxybenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-benzyl-4-methylpyrrolidin-3-yl]-1-(tetrahydro-2H-thiopyran-4-yl)-1,5-dihydro-4H-pyrazolo[3,4-d]pyrimidin-4-one;

6-[(3S,4S)-1-(2-methoxybenzyl)-4-methylpyrrolidin-3-yl]-1-(tetrahydro-2H-pyran-4-yl)-1,5-dihydro-4H-pyrazolo[3,4-d]pyrimidin-4-one;

6-[(3S,4S)-1-(3-methoxybenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-methyl-1-[3-(trifluoromethyl)benzyl]pyrrolidin-3-yl}-1-(tetrahydro-2H-pyran-4-yl)-1,5-dihydro-4H-pyrazolo[3,4-d]pyrimidin-4-one;

6-[(3S,4S)-1-(2,6-difluorobenzyl)-4-methylpyrrolidin-3-yl]-1-(tetrahydro-2H-pyran-4-yl)-1,5-dihydro-4H-pyrazolo[3,4-d]pyrimidin-4-one;

6-{(3S,4S)-4-ethyl-1-[(5-methylpyrazin-2-yl)methyl]pyrrolidin-3-yl}-1-(tetrahydro-2H-pyran-4-yl)-1,5-dihydro-4H-pyrazolo[3,4-d]pyrimidin-4-one;

6-{(3S,4S)-4-ethyl-1-[(6-methoxypyridin-3-yl)methyl]pyrrolidin-3-yl}-1-(tetrahydro-2H-pyran-4-yl)-1,5-dihydro-4H-pyrazolo[3,4-d]pyrimidin-4-one;

6-[(3S,4S)-4-ethyl-1-(pyridin-2-ylmethyl)pyrrolidin-3-yl]-1-(tetrahydro-2H-pyran-4-yl)-1,5-dihydro-4H-pyrazolo[3,4-d]pyrimidin-4-one;

6-[(3S,4S)-4-ethyl-1-(quinoxalin-2-ylcarbonyl)pyrrolidin-3-yl]-1-(tetrahydro-2H-pyran-4-yl)-1,5-dihydro-4H-pyrazolo[3,4-d]pyrimidin-4-one;

6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one;

2-({(3S,4S)-3-ethyl-4-[4-oxo-1-(tetrahydro-2H-pyran-4-yl)-4,5-dihydro-1H-pyrazolo[3,4-d]pyrimidin-6-yl]pyrrolidin-1-yl}methyl)benzonitrile;

3-({(3S,4S)-3-ethyl-4-[4-oxo-1-(tetrahydro-2H-pyran-4-yl)-4,5-dihydro-1H-pyrazolo[3,4-d]pyrimidin-6-yl]pyrrolidin-1-yl}methyl)benzonitrile; and 4-({(3S,4S)-3-ethyl-4-[4-oxo-1-(tetrahydro-2H-pyran-4-yl)-4,5-dihydro-1H-pyrazolo[3,4-d]pyrimidin-6-yl]pyrrolidin-1-yl}methyl)benzonitrile;

or a pharmaceutically acceptable salt thereof.

8. A pharmaceutical composition comprising a compound of claim 1, or a pharmaceutically acceptable salt thereof, and a pharmaceutically acceptable vehicle, carrier or diluent.

9. The composition of claim 8, further comprising a second pharmaceutical agent.

10. The composition of claim 9, wherein the second pharmaceutical agent is selected from the group consisting of donepezil, galantamine, memantine, rivastigmine, and tacrine.

11. A pharmaceutical composition comprising a compound of claim 5, or a pharmaceutically acceptable salt thereof, and a pharmaceutically acceptable vehicle, carrier or diluent.

12. A pharmaceutical composition comprising a compound of claim 6, or a pharmaceutically acceptable salt thereof, and a pharmaceutically acceptable vehicle, carrier or diluent.

13. A pharmaceutical composition comprising a compound of claim 7, or a pharmaceutically acceptable salt thereof, and a pharmaceutically acceptable vehicle, carrier or diluent.

* * * * *